US012195804B2

(12) United States Patent
Johnson et al.

(10) Patent No.: US 12,195,804 B2
(45) Date of Patent: Jan. 14, 2025

(54) TREATMENT OF SQUAMOUS CELL CARCINOMA

(71) Applicant: Board of Regents, The University of Texas System, Austin, TX (US)

(72) Inventors: Faye Johnson, The Woodlands, TX (US); Mitchell Jay Frederick, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1086 days.

(21) Appl. No.: 16/790,471

(22) Filed: Feb. 13, 2020

(65) Prior Publication Data

US 2020/0248273 A1   Aug. 6, 2020

Related U.S. Application Data

(63) Continuation-in-part of application No. PCT/EP2019/071251, filed on Aug. 7, 2019.

(60) Provisional application No. 62/715,634, filed on Aug. 7, 2018.

(51) Int. Cl.
| | | |
|---|---|---|
| *C12Q 1/6886* | (2018.01) | |
| *A61K 31/53* | (2006.01) | |
| *A61K 31/5377* | (2006.01) | |
| *A61K 45/06* | (2006.01) | |
| *C12Q 1/6869* | (2018.01) | |

(52) U.S. Cl.
CPC ........ *C12Q 1/6886* (2013.01); *A61K 31/5377* (2013.01); *C12Q 1/6869* (2013.01); *A61K 45/06* (2013.01)

(58) Field of Classification Search
CPC ................ C12Q 1/6886; C12Q 1/6869; C12Q 2600/106; C12Q 2600/156; A61K 31/5377; A61K 31/53; A61K 45/06
See application file for complete search history.

(56) References Cited

U.S. PATENT DOCUMENTS

2021/0299133 A1   9/2021   Rolli et al.

FOREIGN PATENT DOCUMENTS

| WO | WO 2013/029116 | 3/2013 |
| WO | WO 2014/141038 | 9/2014 |
| WO | WO 2014/144121 | 9/2014 |

OTHER PUBLICATIONS

Verlingue et al., European Journal of Cancer, 2018, 92, 1-10.*
Abad et al., "Notch Inhibition Enhances Cardiac Reprogramming by Increasing MEF2C Transcriptional Activity," *Stem Cell Reports*, 8:548-560, 2017.
Agrawal et al., "Comparative genomic analysis of esophageal adenocarcinoma and squamous cell carcinoma," Cancer Discovery, 2:899-905, 2012.
Agrawal et al., "Exome sequencing of head and neck squamous cell carcinoma reveals inactivating mutations in NOTCH1," *Science*, 333:1154-1157, 2011.
Akbani et al., "A pan-cancer proteomic perspective on The Cancer Genome Atlas," *Nat. Comm.*, 5:3887, 2014.
Beaufils et al., "5-(4,6-Dimorpholino-1,3,5-triazin-2-yl)-4-(trifluoromethyl)pyridin-2-Amine (PQR309), a Potent, Brain-Penetrant, Orally Bioavailable, Pan-Class I PI3K/mTOR Inhibitor as Clinical Candidate in Oncology," *Journal of Medicinal Chemistry*, 60:7524-7538, 2017.
Bendell et al., "A phase 1 study of the sachet formulation of the oral dual PI3K/mTOR inhibitor BEZ235 given twice daily (BID) in patients with advanced solid tumors," Invest. New Drugs, 33:463-471, 2015.
Bendell et al., "Phase I, dose-escalation study of BKM120, an oral pan-Class I PI3K inhibitor, in patients with advanced solid tumors," J. Clin. Oncol., 30:282-90, 2012.
Bohnacker et al., "Deconvolution of Buparlisib's mechanism of action defines specific PI3K and tubulin inhibitors for therapeutic intervention," Nat Comm., 8:14683, 2017.
Bornkamp et al., "Response-adaptive dose-finding under model uncertainty," Ann. Appl. Stat., 5:1611-1631, 2011.
Byers et al., "An Epithelial-Mesenchymal Transition Gene Signature Predicts Resistance to EGFR and PI3K Inhibitors and Identifies Axl as a Therapeutic Target for Overcoming EGFR Inhibitor Resistance," Clin. Cancer Res., 19:279-290, 2013.
Byers et al., "Proteomic profiling identifies dysregulated pathways in small cell lung cancer and novel therapeutic targets including PARP1," Cancer Discov., 2:798-811, 2012.
Cai et al., "Dysregulations in the PI3K pathway and targeted therapies for head and neck squamous cell carcinoma," Oncotarget, 8:22203-22217, 2017.

(Continued)

*Primary Examiner* — Sun Jae Yoo
(74) *Attorney, Agent, or Firm* — Parker Highlander PLLC

(57) ABSTRACT

The present invention relates to a method of predicting the vulnerability of a squamous cell carcinoma (SCC) to inhibition by a PI3K inhibitor, preferably by a PI3K/mTOR inhibitor, including the selection of the patient predicted to benefit from therapeutic administration with the PI3K inhibitor, preferably of the PI3K/mTOR inhibitor. Moreover, the present invention relates to a method of treating a squamous cell carcinoma (SCC) of a mammal, preferably a human patient, comprising administering a therapeutically effective amount of a PI3K inhibitor, preferably a therapeutically effective amount of a PI3K/mTOR inhibitor to said mammal, preferably said human patient. Furthermore, the present invention relates to pharmaceutical compositions and kits associated with the inventive methods.

19 Claims, 41 Drawing Sheets
(36 of 41 Drawing Sheet(s) Filed in Color)
Specification includes a Sequence Listing.

(56) References Cited

OTHER PUBLICATIONS

Cancer Genome Atlas, "Comprehensive genomic characterization of head and neck squamous cell carcinomas," Nature, 517:576-582, 2015.
Castel et al., "PDK1-SGK1 Signaling Sustains AKT-Independent mTORC1 Activation and Confers Resistance to PI3Kalpha Inhibition," Cancer Cell, 30:229-242, 2016.
Cerami et al., "The cBio Cancer Genomics Portal: An Open Platform for Exploring Multidimensional Cancer Genomics Data," Cancer Discovery, 2:401-404, 2012.
Chandarlapaty et al., "AKT inhibition relieves feedback suppression of receptor tyrosine kinase expression and activity," Cancer Cell, 19:58-71, 2011.
Chiang MY, Radojcic V, Maillard I. Oncogenic Notch signaling in T-cell and B-cell lymphoproliferative disorders. Current opinion in hematology 2016; 23: 362-370.
Courtney et al., "The PI3K pathway as drug target in human cancer," J. Clin. Oncol., 28:1075-1083, 2010.
De Buck et al., "Population pharmacokinetics and pharmacodynamics of BYL719, a phosphoinositide 3-kinase antagonist, in adult patients with advanced solid malignancies," Br. J. Clin. Pharmacol., 78:543-555, 2014.
Di Nicolantonio et al., "Deregulation of the PI3K and KRAS signaling pathways in human cancer cells determines their response to everolimus," J. Clin. Invest., 120:2858-2866, 2010.
Di-Poi et al., "Antiapoptotic role of PPARbeta in keratinocytes via transcriptional control of the Akt1 signaling pathway," Mol. Cell, 10:721-733, 2002.
D'Souza et al., "The many facets of Notch ligands," Oncogene, 27:5148-5167, 2008.
Elkabets et al., "AXL mediates resistance to PI3Kalpha inhibition by activating the EGFR/PKC/mTOR axis in head and neck and esophageal squamous cell carcinomas," Cancer Cell, 27:533-546, 2015.
Ferlay et al., "Cancer incidence and mortality worldwide: Sources, methods and major patterns in GLOBOCAN 2012," International Journal of Cancer, 136:E359-E386, 2015.
Ferrando, "The role of NOTCH1 signaling in T-ALL," Hematology Am. Soc. Hematol. Educ. Program, 2009:353-361, 2009.
Ferrarotto et al., "Accuracy: phase (P) 2 trial of AL101, a pan-Notch inhibitor, in patients (pts) with recurrent/metastatic (R/M) adenoid cystic carcinoma (ACC) with Notch activating mutations (Notchact mut)," *Journal of Clinical Oncology*, 37: TPS6098-TPS6098, 2019.
Ferrarotto et al., "Activating NOTCH1 mutations define a distinct subgroup of adenoid cystic carcinoma patients with poor prognosis, propensity to bone and liver metastasis, and potential responsiveness to Notch1 inhibitors," J. Clin. Oncol., 35:352-360, 2017.
Ferrarotto et al., "Epithelial-Mesenchymal Transition Predicts Polo-Like Kinase 1 Inhibitor-Mediated Apoptosis in Non-Small Cell Lung Cancer," Clin. Cancer Res., 22:1674-1686, 2016.
Fruman & Rommel, "PI3K and cancer: lessons, challenges and opportunities," Nat. Rev. Drug Discov., 13:140-156, 2014.
Fruman et al., "The PI3K Pathway in Human Disease," Cell, 170:605-635, 2017.
Habets et al., "Safe targeting of T cell acute lymphoblastic leukemia by pathology-specific NOTCH inhibition," *Science Translational Medicine*, 11: eaau6246, 2019.
Hales et al., "New insights into Notch1 regulation of the PI3K-AKT-mTOR1 signaling axis: targeted therapy of gamma-secretase inhibitor resistant T-cell acute lymphoblastic leukemia," *Cell Signal*, 26:149-161, 2014.
Herzog et al., "PI3K/mTOR inhibitor PF-04691502 antitumor activity is enhanced with induction of wild-type TP53 in human xenograft and murine knockout models of head and neck cancer," Clin. Cancer Res., 19:3808-3819, 2013.
Ho et al., "The Mutational Landscape of Adenoid Cystic Carcinoma," Nature Genetics, 45:791-798, 2013.

Iglesias-Bartolome et al., "Exploiting the Head and Neck Cancer Oncogenome: Widespread PI3K-mTOR Pathway Alterations and Novel Molecular Targets," Cancer Discov., 3:722-725, 2013.
Janku et al., "PI3K/AKT/mTOR inhibitors in patients with breast and gynecologic malignancies harboring PIK3CA mutations," J. Clin. Oncol., 30:777-782, 2012.
Janku et al., "PIK3CA Mutations in Patients with Advanced Cancers Treated with PI3K/AKT/mTOR Axis Inhibitors," Molecular Cancer Therapeutics, 10:558-565., 2011.
Jimeno et al., "A randomized, phase 2 trial of docetaxel with or without PX-866, an irreversible oral phosphatidylinositol 3-kinase inhibitor, in patients with relapsed or metastatic head and neck squamous cell cancer," Oral Oncol., 51:383-388, 2015.
Johnson et al., "NOTCH1 inactivating mutation mediates sensitivity to PI3K/mTOR inhibitors in head and neck squamous cell carcinoma," Abstract 393, Proceedings of the $107^{th}$ Annual meeting of the American Association for Cancer Research, Cancer Res., 76(14 Supplement):393, 2016.
Juric et al., "Convergent loss of PTEN leads to clinical resistance to a PI(3)Kalpha inhibitor," Nature, 518:240-244, 2015.
Kalu et al., "Comprehensive pharmacogenomic profiling of human papillomavirus-positive and -negative squamous cell carcinoma identifies sensitivity to aurora kinase inhibition in KMT2D mutants," Cancer Lett., 431:64-72, 2018.
Kalu et al., "Genomic characterization of human papillomavirus-positive and -negative human squamous cell cancer cell lines," Oncotarget, 8:86369-86383, 2017.
Kelly et al., "Notch-induced T cell development requires phosphoinositide-dependent kinase 1," EMBO J., 26:3441-3450, 2007.
Keysar et al., "A patient tumor transplant model of squamous cell cancer identifies PI3K inhibitors as candidate therapeutics in defined molecular bins," Mol. Oncol., 7:776-790, 2013.
Kluk et al., "Gauging NOTCH1 Activation in Cancer Using Immunohistochemistry," PLoS One, 8(6):e67306, 2013.
Lee et al., "Vital roles of mTOR complex 2 in Notch-driven thymocyte differentiation and leukemia," J. Exp. Med., 209:713-728, 2012.
Li et al., "Genomic analysis of head and neck squamous cell carcinoma cell lines and human tumors: a rational approach to preclinical model selection," Mol. Cancer Res., 12:571-582, 2014.
Liu et al., "BAY 80-6946 is a highly selective intravenous PI3K inhibitor with potent p110alpha and p110delta activities in tumor cell lines and xenograft models," Mol. Cancer Ther., 12:2319-2330, 2013.
Liu et al., "LGR5 promotes epithelial ovarian cancer proliferation, metastasis, and epithelial-mesenchymal transition through the Notch1 signaling pathway," Cancer Med., 7:3132-3142, 2018.
Lui et al., "Frequent mutation of the PI3K pathway in head and neck cancer defines predictive biomarkers," Cancer Discov., 3:761-769, 2013.
Maira, "PI3K inhibitors for cancer treatment: five years of preclinical and clinical research after BEZ235," Mol. Cancer Ther., 10:2016, 2011.
Mao, "NOTCH Mutations: Multiple Faces in Human Malignancies," Cancer Prevention Research, 8:259-261, 2015.
Maxwell et al., "Practical guide for the comparison of two next-generation sequencing systems for solid tumour analysis in a universal healthcare system," J Clin. Pathol., 72:225-231, 2019.
Mazumdar et al., "A Comprehensive Evaluation of Biomarkers Predictive of Response to PI3K Inhibitors and of Resistance Mechanisms in Head and Neck Squamous Cell Carcinoma," Mol. Cancer Ther., 13:2738-2750, 2014.
Mohan et al., "MEK Inhibitor PD-0325901 Overcomes Resistance to PI3K/mTOR Inhibitor PF-5212384 and Potentiates Antitumor Effects in Human Head and Neck Squamous Cell Carcinoma," Clin. Cancer Res., 21:3946-3956, 2015.
Muellner et al., "A chemical genetic screen reveals a resistance mechanism to PI3K inhibitors in cancer," *Nature Chemical Biology*, 7(11):787-793, 2011.
Munster et al., "First-in-Human Phase I Study of GSK2126458, an Oral Pan-Class I Phosphatidylinositol-3-Kinase Inhibitor, in Patients with Advanced Solid Tumor Malignancies," Clin. Cancer Res., 22:1932-1939, 2016.

(56) References Cited

OTHER PUBLICATIONS

Myers et al., "An orthotopic nude mouse model of oral tongue squamous cell carcinoma," Clin. Cancer Res., 8:293-298, 2002.
Nowell & Radtke, "Notch as a tumour suppressor," Nat. Rev. Cancer., 17:145-159, 2017.
PCT International Search Report and Written Opinion issued in International Application No. PCT/EP2019/071251, mailed Nov. 14, 2019.
Pickering et al., "Integrative genomic characterization of oral squamous cell carcinoma identifies frequent somatic drivers," Cancer Discov., 3:770-781, 2013.
Pickering et al., "Mutational landscape of aggressive cutaneous squamous cell carcinoma," Clin. Cancer Research, 20:6582-6592, 2014.
Pounds & Morris, "Estimating the occurrence of false positives and false negatives in microarray studies by approximating and partitioning the empirical distribution of p-values," Bioinformatics, 19:1236-1242, 2003.
Rettig et al., "Cleaved NOTCH1 expression pattern in head and neck squamous cell carcinoma is associated with NOTCH1 mutation, HPV status and high-risk features," Cancer Prevention Research, 8:287-295, 2015.
Ritz & Streibig, "Bioassay Analysis Using R," Journal of Statistical Software; 12:5, 2005.
Rodon & Tabernero, "Improving the Armamentarium of PI3K Inhibitors with Isoform-Selective Agents: A New Light in the Darkness," Cancer Discov., 7:666-669, 2017.
Rodon et al., "Development of PI3K inhibitors: lessons learned from early clinical trials," Nat. Rev. Clin. Oncol., 10:143-153, 2013.
Salphati et al., "Preclinical assessment of the absorption and disposition of the phosphatidylinositol 3-kinase/mammalian target of rapamycin inhibitor GDC-0980 and prediction of its pharmacokinetics and efficacy in human," Drug Metab. Dispos., 40:1785-1796, 2012.
Sambandam et al., "Abstract 2992: Identification of NOTCH1 inactivating mutation as a therapeutic vulnerability to PI3K/mTOR pathway inhibition in head and neck squamous cell carcinoma (HNSCC)," Cancer Research, 77(13 Supplement):2992, 2017.
Sambandam et al., "PDK1 Mediates NOTCH1-Mutated Head and Neck Squamous Carcinoma Vulnerability to Therapeutic PI3K/mTOR Inhibition," *Clinical Cancer Research*, 25(11):3329-3340, 2019.
Shah et al., "NOTCH1 signaling in head and neck squamous cell carcinoma," *Cells*, 9:2677, 2020.
Song et al., "Notch1 deficiency decreases hepatic lipid accumulation by induction of fatty acid oxidation," Scientific Reports, 6:19377, 2016.
Soria et al., "Osimertinib in Untreated EGFR-Mutated Advanced Non-Small-Cell Lung Cancer," N. Engl. J. Med., 378:113-125, 2018.
Stransky et al., "The mutational landscape of head and neck squamous cell carcinoma," Science, 333:1157-1160, 2011.
Tutt et al., "Oral poly(ADP-ribose) polymerase inhibitor olaparib in patients with BRCA1 or BRCA2 mutations and advanced breast cancer: a proof-of-concept trial," Lancet, 376:235-244, 2010.
Venkatesh et al., "Targeting Notch signalling pathway of cancer stem cells," Stem Cell Investig., 5:5, 2018.
Wang et al., "mTOR co-targeting in cetuximab resistance in head and neck cancers harboring PIK3CA and RAS mutations," J. Natl. Cancer Inst., 106(9):dju215, 2014.
Wang et al., "mTOR co-targeting strategies for head and neck cancer therapy," Cancer Metastasis Rev., 36:491-502, 2017.
Wicki et al., "First-in human, phase1, dose-escalation pharmacokinetic and pharmacodynamic study of the oral dual PI3K and mTORC1/2 inhibitor PQR309 in patients with advanced solid tumors (SAKK 67/13)," European Journal of Cancer, 96:6-16, 2018.
Wu et al., "COL11A1 confers chemoresistance on ovarian cancer cells through the activation of Akt/c/EBPbeta pathway and PDK1 stabilization," Oncotarget, 6:23748-23763, 2015.
Yamaguchi et al., "A synthetic-lethality RNAi screen reveals an ERK-mTOR co-targeting pro-apoptotic switch in PIK3CA(+) oral cancers," Oncotarget, 7:10696-10709, 2016.
Zhang et al., "Does Notch play a tumor suppressor role across diverse squamous cell carcinomas?" Cancer Med., 5:2048-2060, 2016.
Zhang et al., "Mutations of the LIM protein AJUBA mediate sensitivity of head and neck squamous cell carcinoma to treatment with cell-cycle inhibitors," Cancer Lett., 392:71-82, 2017.
Zhao et al., "Assembly and initial characterization of a panel of 85 genomically validated cell lines from diverse head and neck tumor sites," Clin. Cancer Res., 17:7248-7264, 2011.
Zumsteg et al., "Taselisib (GDC-0032), a Potent beta-Sparing Small Molecule Inhibitor of PI3K, Radiosensitizes Head and Neck Squamous Carcinomas Containing Activating PIK3CA Alterations," Clin. Cancer Res., 22:2009-2019, 2016.

* cited by examiner

| Cell Line | NOTCH1 genotype | PIK3CA genotype |
|---|---|---|
| MDA686LN | WT | p.I112F[a] |
| MDA686TU | WT | p.I112F[a] |
| UMSCC3 | WT | p.C378Y[a] |
| SCC61 | WT | p.E542K |
| Detroit562 | WT | p.H1047R |
| UMSCC17A | WT | p.E726K |
| UMSCC14B | WT | p.F977Y |
| UMSCC19 | WT | p.H1047R |
| UMSCC17B | WT | p.E726K |
| TR146 | p.A1524V[b] | p.E545K |
| JHU029 | p.414_419del | p.H1047L |
| UMSCC85 | p.E694* | p.H1047R |
| PCI15A | p.Q1957* | WT |
| PCI15B | p.Q1957* | WT |
| HN30 | p.C478F | WT |
| MDA1686 | p.H2018fs | WT |
| HN31 | p.C478F | WT |
| HN4 | p.C344fs | WT |
| UMSCC22A | p.E1679* | WT |
| UMSCC25 | p.V489fs | WT |
| SCC45 | p.G72R | WT |
| UMSCC22B | p.E1679* | WT |
| 1483 | p.F357del | WT |
| UMSCC47 | p.G192* | WT |
| MSK922 | p.C1536Y[b] | WT |
| PCI13 | p.G1753W[b] | WT |

| Cell line | NOTCH1 genotype | PIK3CA genotype |
|---|---|---|
| MDA686LN | WT | p.I112F ¥ |
| MDA686TU | WT | p.I112F ¥ |
| UMSCC3 | WT | p.C378Y ¥ |
| SCC61 | WT | p.E542K |
| DETROIT562 | WT | p.H1047R |
| UMSCC17A | WT | p.E726K |
| UMSCC14B | WT | p.F977Y |
| UMSCC19 | WT | p.H1047R |
| UMSCC17B | WT | p.E726K |
| TR146 | p.A1524V † | p.E545K |
| JHU029 | p.414_419del | p.H1047L |
| UMSCC85 | p.E694* | p.H1047R |
| PCI15A | p.Q1957* | WT |
| PCI15B | p.Q1957* | WT |
| UMSCC22A | p.E1679* | WT |
| UMSCC22B | p.E1679* | WT |
| UMSCC47 | p.G192* | WT |
| UTSCC45 | p.G72R | WT |
| HN31 | p.C478F | WT |
| HN30 | p.C478F | WT |
| MDA1686 | p.H2018fs | WT |
| HN4 | p.C344fs | WT |
| UMSCC25 | p.V489fs | WT |
| 1483 | p.F357del | WT |

FIG. 6E

PI3K/mTOR pathway inhibitors

| Drug | Target | Cmax (µM) | Lowest IC$_{70}$ (µM) | Number of sensitive lines | Number of resistant lines | Reference |
|---|---|---|---|---|---|---|
| GSK2126458 (Omipalisib) | Dual PI3K/mTOR | 0.09 | 0.01 | 33 | 26 | (22) |
| BEZ235 (Dactolisib) | Dual PI3K/mTOR | 3.8 | 0.04 | 40 | 19 | (23) |
| BAY806946 (Copanlisib) | Pan class I PI3K | 2.6 | 0.06 | 45 | 14 | (24) |
| BKM120 (Buparlisib) | Pan class I PI3K | 2.7 | 0.32 | 51 | 8 | (25) |
| BYL719 (Alpelisib) | PI3K-α | 3.1 | 0.60 | 9 | 50 | (26) |
| GDC0980 (Apitolisib) | Dual PI3K/mTOR | 0.43 | 0.13 | 11 | 48 | (27) |
| PQR309 (Bimiralisib) | Dual PI3K/mTOR | 2.7 | 0.57 | 30 | 29 | (28,29) |

SEQUENCE LISTING

<160> NUMBER OF SEQ ID NOS: 3

<210> SEQ ID NO 1
<211> LENGTH: 7668
<212> TYPE: DNA
<213> ORGANISM: Homo sapiens

<400> SEQUENCE: 1

| | | | | | |
|---|---|---|---|---|---|
| atgccgccgc | tcctggcgcc | cctgctctgc | ctggcgctgc | tgcccgcgct | cgccgcacga | 60 |
| ggcccgcgat | gctcccagcc | cggtgagacc | tgcctgaatg | cgggaagtg | tgaagcggcc | 120 |
| aatggcacgg | aggcctgcgt | ctgtggcggg | gccttcgtgg | gcccgcgatg | ccaggacccc | 180 |
| aacccgtgcc | tcagcacccc | ctgcaagaac | gccgggacat | gccacgtggt | ggaccgcaga | 240 |
| ggcgtggcag | actatgcctg | cagctgtgcc | ctgggcttct | ctgggcccct | ctgcctgaca | 300 |
| cccctggaca | tgcctgcct | caccaacccc | tgccgcaacg | ggcacctg | cgacctgctc | 360 |
| acgctgacgg | agtacaagtg | ccgctgcccg | cccggctggt | cagggaaatc | gtgccagcag | 420 |
| gctgacccgt | gcgcctccaa | cccctgcgcc | aacggtggcc | agtgcctgcc | cttcgaggcc | 480 |
| tcctacatct | gccactgccc | acccagcttc | catggcccca | cctgccggca | ggatgtcaac | 540 |
| gagtgtggcc | agaagcccgg | gctttgccgc | cacggaggca | cctgccacaa | cgaggtcggc | 600 |
| tcctaccgct | gcgtctgccg | cgccacccac | actggcccca | actgcgagcg | ccctacgtg | 660 |
| ccctgcagcc | cctcgccctg | ccagaacggg | ggcacctgcc | gcccacgggg | cgacgtcacc | 720 |
| cacgagtgtg | cctgcctgcc | aggcttcacc | ggccagaact | gtgaggaaaa | tatcgacgat | 780 |
| tgtccaggaa | acaactgcaa | gaacggggt | gcctgtgtgg | acggcgtgaa | cacctacaac | 840 |
| tgccgctgcc | cgccagagtg | gacaggtcag | tactgtaccg | aggatgtgga | cgagtgccag | 900 |
| ctgatgccaa | atgcctgcca | gaacggcggg | acctgccaca | cacccacgg | tggctacaac | 960 |
| tgcgtgtgtg | tcaacggctg | gactggtgag | gactgcagcg | agaacattga | tgactgtgcc | 1020 |
| agcgccgcct | gcttccacgg | cgccacctgc | catgaccgtg | tggcctcctt | ctactgcgag | 1080 |
| tgtcccatg | gccgcacagg | tctgctgtgc | cacctcaacg | acgcatgcat | cagcaacccc | 1140 |
| tgtaacgagg | gctccaactg | cgacaccaac | cctgtcaatg | gcaaggccat | ctgcacctgc | 1200 |
| ccctcggggt | acacgggccc | ggcctgcagc | caggacgtgg | atgagtgctc | gctgggtgcc | 1260 |
| aaccctgcg | agcatgcggg | caagtgcatc | aacacgctgg | gctccttcga | gtgccagtgt | 1320 |
| ctgcagggct | acacgggccc | ccgatgcgag | atcgacgtca | acgagtgcgt | ctcgaacccg | 1380 |
| tgccagaacg | acgccacctg | cctggaccag | attggggagt | ccagtgcat | ctgcatgccc | 1440 |
| ggctacgagg | gtgtgcactg | cgaggtcaac | acagacgagt | gtgccagcag | ccctgcctg | 1500 |
| cacaatggcc | gctgcctgga | caagatcaat | gagttccagt | gcgagtgccc | cacgggcttc | 1560 |
| actgggcatc | tgtgccagta | cgatgtggac | gagtgtgcca | gcaccccctg | caagaatggt | 1620 |
| gccaagtgcc | tggacggacc | caacacttac | acctgtgtgt | gcacggaagg | gtacacgggg | 1680 |
| acgcactgcg | aggtggacat | cgatgagtgc | gaccccgacc | cctgccacta | cggctcctgc | 1740 |
| aaggacggcg | tcgccacctt | cacctgcctc | tgccgcccag | gctacacggg | ccaccactgc | 1800 |
| gagaccaaca | tcaacgagtg | ctccagccag | ccctgccgcc | acggggcac | ctgccaggac | 1860 |
| cgcgacaacg | cctacctctg | cttctgcctg | aagggacca | caggacccaa | ctgcgagatc | 1920 |
| aacctggatg | actgtgccag | cagccctgc | gactcgggca | cctgtctgga | caagatcgat | 1980 |
| ggctacgagt | gtgcctgtga | gccgggctac | acgggagca | tgtgtaacat | caacatcgat | 2040 |
| gagtgtgcgg | gcaaccccctg | ccacaacggg | ggcacctgcg | aggacggcat | caatggcttc | 2100 |

```
acctgccgct gccccgaggg ctaccacgac cccacctgcc tgtctgaggt caatgagtgc    2160
aacagcaacc cctgcgtcca cggggcctgc cgggacagcc tcaacgggta caagtgcgac    2220
tgtgaccctg ggtggagtgg gaccaactgt gacatcaaca acaatgagtg tgaatccaac    2280
ccttgtgtca acggcggcac ctgcaaagac atgaccagtg gctacgtgtg cacctgccgg    2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg ccccagccc ctgcagaaac    2520 ggcggggagt gcaggcaatc cgaggactat gagagcttct cctgtgtctg ccccacgggc    2580
tggcaagggc agacctgtga ggtcgacatc aacgagtgcg ttctgagccc gtgccggcac    2640
ggcgcatcct gccagaacac ccacggcggc taccgctgcc actgccaggc cggctacagt    2700
gggcgcaact gcgagaccga catcgacgac tgccggccca cccgtgtca acgggggc     2760 tcctgcacag acggcatcaa cacggccttc tgcgactgcc tgcccggctt ccggggcact    2820
ttctgtgagg aggacatcaa cgagtgtgcc agtgaccct gccgcaacgg gccaactgc    2880 acggactgcg tggacagcta cacgtgcacc tgccccgcag gcttcagcgg gatccactgt    2940
gagaacaaca cgcctgactg cacagagagc tcctgcttca cggtggcac ctgcgtggac    3000 ggcatcaact cgttcacctg cctgtgtcca cccggcttca cgggcagcta ctgccagcac    3060
gatgtcaatg agtgcgactc acagccctgc ctgcatggcg gcacctgtca ggacggctgc    3120
ggctcctaca ggtgcacctg cccccagggc tacactggcc ccaactgcca gaaccttgtg    3180
cactggtgtg actcctcgcc ctgcaagaac ggcggcaaat gctggcagac ccacacccag    3240
taccgctgcg agtgccccag cggctggacc ggcctttact gcgacgtgcc cagcgtgtcc    3300
tgtgaggtgg ctgcgcagcg acaaggtgtt gacgttgccc gcctgtgcca gcatggaggg    3360
ctctgtgtgg acgcgggcaa cacgcaccac tgccgctgcc aggcgggcta cacaggcagc    3420
tactgtgagg acctggtgga cgagtgctca cccagcccct gccagaacgg ggccacctgc    3480
acggactacc tgggcggcta ctcctgcaag tgcgtggccg gctaccacgg ggtgaactgc    3540
tctgaggaga tcgacgagtg cctctcccac ccctgccaga cgggggcac ctgcctcgac    3600 ctccccaaca cctacaagtg ctcctgccca cggggcactc agggtgtgca ctgtgagatc    3660
aacgtggacg actgcaatcc ccccgttgac cccgtgtccc ggagcccaa gtgctttaac    3720 aacggcacct gcgtggacca ggtgggcggc tacagctgca cctgcccgcc gggcttcgtg    3780
ggtgagcgct gtgaggggga tgtcaacgag tgcctgtcca atccctgcga cgcccgtggc    3840
acccagaact gcgtgcagcg cgtcaatgac ttccactgcg agtgccgtgc tggtcacacc    3900
gggcgccgct gcgagtccgt catcaatggc tgcaaaggca gccctgcaa gaatggggc    3960 acctgcgccg tggcctccaa caccgcccgc gggttcatct gcaagtgccc tgcgggcttc    4020
gagggcgcca cgtgtgagaa tgacgctcgt acctgcggca gcctgcgctg cctcaacggc    4080
ggcacatgca tctccggccc gcgcagcccc acctgcctgt gcctgggccc cttcacgggc    4140
cccgaatgcc agttcccggc cagcagcccc tgcctgggcg caacccctg ctacaaccag    4200 gggacctgtg agcccacatc cgagagcccc ttctaccgtt gcctgtgccc cgccaaattc    4260
aacgggctct tgtgccacat cctggactac agcttcgggg gtggggccgg cgcgacatc    4320 cccccgccgc tgatcgagga ggcgtgcgag ctgcccgagt gccaggagga cgcgggcaac    4380
aaggtctgca gcctgcagtg caacaaccac gcgtgcggct gggacggcgg tgactgctcc    4440
```

```
ctcaacttca atgacccctg gaagaactgc acgcagtctc tgcagtgctg gaagtacttc    4500
agtgacggcc actgtgacag ccagtgcaac tcagccggct gcctcttcga cggctttgac    4560
tgccagcgtg cggaaggcca gtgcaacccc ctgtacgacc agtactgcaa ggaccacttc    4620
agcgacgggc actgcgacca gggctgcaac agcgcggagt gcgagtggga cgggctggac    4680
tgtgcggagc atgtacccga gaggctggcg gccggcacgc tggtggtggt ggtgctgatg    4740
ccgccggagc agctgcgcaa cagctccttc cacttcctgc gggagctcag ccgcgtgctg    4800
cacaccaacg tggtcttcaa gcgtgacgca cacggccagc agatgatctt ccctactac     4860 ggccgcgagg aggagctgcg caagcacccc atcaagcgtg ccgccgaggg ctgggccgca    4920
cctgacgccc tgctgggcca ggtgaaggcc tcgctgctcc ctggtggcag cgagggtggg    4980
cggcggcgga gggagctgga ccccatggac gtccgcggct ccatcgtcta cctggagatt    5040
gacaaccggc agtgtgtgca ggcctcctcg cagtgcttcc agagtgccac cgacgtggcc    5100
gcattcctgg agcgctcgc ctcgctgggc agcctcaaca tcccctacaa gatcgaggcc     5160
gtgcagagtg agaccgtgga gccgcccccg ccggcgcagc tgcacttcat gtacgtggcg    5220
gcggccgcct ttgtgcttct gttcttcgtg gctgcggggg tgctgctgtc ccgcaagcgc    5280
cggcggcagc atgccagct ctggttccct gagggcttca agtgtctga ggccagcaag       5340 aagaagcggc gggagcccct cggcgaggac tccgtgggcc tcaagcccct gaagaacgct    5400
tcagacggtg ccctcatgga cgacaaccag aatgagtggg gggacgagga cctggagacc    5460
aagaagttcc ggttcgagga gcccgtggtt ctgcctgacc tggacgacca gacagaccac    5520
cggcagtgga ctcagcagca cctggatgcc gctgacctgc gcatgtctgc catggccccc    5580
acaccgcccc agggtgaggt tgacgccgac tgcatggacg tcaatgtccg cgggcctgat    5640
ggcttcaccc cgctcatgat cgcctcctgc agcgggggcg gcctggagac gggcaacagc    5700
gaggaagagg aggacgcgcc ggccgtcatc tccgacttca tctaccaggg cgccagcctg    5760
cacaaccaga cagaccgcac gggcgagacc gccttgcacc tggccgcccg ctactcacgc    5820
tctgatgccg ccaagcgcct gctggaggcc agcgcagatg ccaacatcca ggacaacatg    5880
ggccgcaccc cgctgcatgc ggctgtgtct ccgacgcac aaggtgtctt ccagatcctg     5940
atccggaacc gagccacaga cctggatgcc cgcatgcatg atggcacgac gccactgatc    6000
ctggctgccc gcctggccgt ggagggcatg ctggaggacc tcatcaactc acacgccgac    6060
gtcaacgccg tagatgacct gggcaagtcc gccctgcact gggccgccgc cgtgaacaat    6120
gtggatgccg cagttgtgct cctgaagaac ggggctaaca agatatgca gaacaacagg      6180 gaggagacac ccctgttct ggccgcccgg gagggcagct acgagaccgc caaggtgctg       6240
ctggaccact tgccaaccg ggacatcacg gatcatatgg accgcctgcc gcgcgacatc      6300
gcacaggagc gcatgcatca cgacatcgtg aggctgctgg acgagtacaa cctggtgcgc    6360
agcccgcagc tgcacggagc cccgctgggg ggcacgccca cctgtcgcc ccgctctgc      6420 tcgcccaacg gctacctggg cagcctcaag cccggcgtgc agggcaagaa ggtccgcaag    6480
cccagcagca aaggcctggc ctgtggaagc aaggaggcca aggacctcaa ggcacggagg    6540
aagaagtccc aggacggcaa gggctgcctg ctggacagct ccggcatgct ctcgcccgtg    6600
gactccctgg agtcacccca tggctacctg tcagacgtgg cctcgccgcc actgctgccc    6660
tccccgttcc agcagtctcc gtccgtgccc ctcaaccacc tgcctgggat gcccgacacc    6720
cacctgggca tcgggcacct gaacgtggcg gccaagccg agatggcggc gctgggtggg    6780
ggcggccggc tggcctttga gactggccca cctcgtctct cccacctgcc tgtggcctct    6840
```

-continued

```
ggcaccagca ccgtcctggg ctccagcagc ggaggggccc tgaatttcac tgtgggcggg   6900
tccaccagtt tgaatggtca atgcgagtgg ctgtcccggc tgcagagcgg catggtgccg   6960
aaccaataca accctctgcg ggggagtgtg gcaccaggcc ccctgagcac acaggccccc   7020
tccctgcagc atggcatggt aggcccgctg cacagtagcc ttgctgccag cgccctgtcc   7080
cagatgatga gctaccaggg cctgcccagc acccggctgg ccacccagcc tcacctggtg   7140
cagacccagc aggtgcagcc acaaaactta cagatgcagc agcagaacct gcagccagca   7200
aacatccagc agcagcaaag cctgcagccg ccaccaccac caccacagcc gcaccttggc   7260
gtgagctcag cagccagcgg ccacctgggc cggagcttcc tgagtggaga gccgagccag   7320
gcagacgtgc agccactggg ccccagcagc ctggcggtgc acactattct gccccaggag   7380
agccccgccc tgcccacgtc gctgccatcc tcgctggtcc cacccgtgac cgcagcccag   7440
ttcctgacgc cccctcgca gcacagctac tcctcgcctg tggacaacac ccccagccac   7500
cagctacagg tgcctgagca ccccttcctc accccgtccc ctgagtcccc tgaccagtgg   7560
tccagctcgt ccccgcattc caacgtctcc gactggtccg agggcgtctc cagccctccc   7620
accagcatgc agtcccagat cgcccgcatt ccggaggcct tcaagtaa   7668
```

<210> SEQ ID NO 2
<211> LENGTH: 2555
<212> TYPE: PRT
<213> ORGANISM: Homo sapiens

<400> SEQUENCE: 2

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220
```

-continued

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
            245                 250                 255

Asn Ile Asp Asp Cys Pro Gly Asn Asn Cys Lys Asn Gly Gly Ala Cys
        260                 265                 270

Val Asp Gly Val Asn Thr Tyr Asn Cys Arg Cys Pro Pro Glu Trp Thr
    275                 280                 285

Gly Gln Tyr Cys Thr Glu Asp Val Asp Glu Cys Gln Leu Met Pro Asn
290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
            325                 330                 335

Asp Asp Cys Ala Ser Ala Ala Cys Phe His Gly Ala Thr Cys His Asp
        340                 345                 350

Arg Val Ala Ser Phe Tyr Cys Glu Cys Pro His Gly Arg Thr Gly Leu
    355                 360                 365

Leu Cys His Leu Asn Asp Ala Cys Ile Ser Asn Pro Cys Asn Glu Gly
370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
            405                 410                 415

Ser Leu Gly Ala Asn Pro Cys Glu His Ala Gly Lys Cys Ile Asn Thr
        420                 425                 430

Leu Gly Ser Phe Glu Cys Gln Cys Leu Gln Gly Tyr Thr Gly Pro Arg
    435                 440                 445

Cys Glu Ile Asp Val Asn Glu Cys Val Ser Asn Pro Cys Gln Asn Asp
450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
            485                 490                 495

Ser Pro Cys Leu His Asn Gly Arg Cys Leu Asp Lys Ile Asn Glu Phe
        500                 505                 510

Gln Cys Glu Cys Pro Thr Gly Phe Thr Gly His Leu Cys Gln Tyr Asp
    515                 520                 525

Val Asp Glu Cys Ala Ser Thr Pro Cys Lys Asn Gly Ala Lys Cys Leu
530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Arg
        580                 585                 590

Pro Gly Tyr Thr Gly His His Cys Glu Thr Asn Ile Asn Glu Cys Ser
    595                 600                 605

Ser Gln Pro Cys Arg His Gly Gly Thr Cys Gln Asp Arg Asp Asn Ala
610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu

-continued

```
                645                 650                 655
Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
                755                 760                 765

Lys Asp Met Thr Ser Gly Tyr Val Cys Thr Cys Arg Glu Gly Phe Ser
        770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Gly Gln
        850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
        930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
        980                 985                 990

Phe Asn Gly Gly Thr Cys Val Asp Gly Ile Asn Ser Phe Thr Cys Leu
        995                 1000                1005

Cys Pro Pro Gly Phe Thr Gly Ser Tyr Cys Gln His Asp Val Asn
        1010                1015                1020

Glu Cys Asp Ser Gln Pro Cys Leu His Gly Gly Thr Cys Gln Asp
        1025                1030                1035

Gly Cys Gly Ser Tyr Arg Cys Thr Cys Pro Gln Gly Tyr Thr Gly
        1040                1045                1050

Pro Asn Cys Gln Asn Leu Val His Trp Cys Asp Ser Ser Pro Cys
        1055                1060                1065
```

```
Lys Asn Gly Gly Lys Cys Trp Gln Thr His Thr Gln Tyr Arg Cys
1070            1075               1080

Glu Cys Pro Ser Gly Trp Thr Gly Leu Tyr Cys Asp Val Pro Ser
1085            1090               1095

Val Ser Cys Glu Val Ala Ala Gln Arg Gln Gly Val Asp Val Ala
1100            1105               1110

Arg Leu Cys Gln His Gly Gly Leu Cys Val Asp Ala Gly Asn Thr
1115            1120               1125

His His Cys Arg Cys Gln Ala Gly Tyr Thr Gly Ser Tyr Cys Glu
1130            1135               1140

Asp Leu Val Asp Glu Cys Ser Pro Ser Pro Cys Gln Asn Gly Ala
1145            1150               1155

Thr Cys Thr Asp Tyr Leu Gly Gly Tyr Ser Cys Lys Cys Val Ala
1160            1165               1170

Gly Tyr His Gly Val Asn Cys Ser Glu Glu Ile Asp Glu Cys Leu
1175            1180               1185

Ser His Pro Cys Gln Asn Gly Gly Thr Cys Leu Asp Leu Pro Asn
1190            1195               1200

Thr Tyr Lys Cys Ser Cys Pro Arg Gly Thr Gln Gly Val His Cys
1205            1210               1215

Glu Ile Asn Val Asp Asp Cys Asn Pro Pro Val Asp Pro Val Ser
1220            1225               1230

Arg Ser Pro Lys Cys Phe Asn Asn Gly Thr Cys Val Asp Gln Val
1235            1240               1245

Gly Gly Tyr Ser Cys Thr Cys Pro Pro Gly Phe Val Gly Glu Arg
1250            1255               1260

Cys Glu Gly Asp Val Asn Glu Cys Leu Ser Asn Pro Cys Asp Ala
1265            1270               1275

Arg Gly Thr Gln Asn Cys Val Gln Arg Val Asn Asp Phe His Cys
1280            1285               1290

Glu Cys Arg Ala Gly His Thr Gly Arg Arg Cys Glu Ser Val Ile
1295            1300               1305

Asn Gly Cys Lys Gly Lys Pro Cys Lys Asn Gly Gly Thr Cys Ala
1310            1315               1320

Val Ala Ser Asn Thr Ala Arg Gly Phe Ile Cys Lys Cys Pro Ala
1325            1330               1335

Gly Phe Glu Gly Ala Thr Cys Glu Asn Asp Ala Arg Thr Cys Gly
1340            1345               1350

Ser Leu Arg Cys Leu Asn Gly Gly Thr Cys Ile Ser Gly Pro Arg
1355            1360               1365

Ser Pro Thr Cys Leu Cys Leu Gly Pro Phe Thr Gly Pro Glu Cys
1370            1375               1380

Gln Phe Pro Ala Ser Ser Pro Cys Leu Gly Gly Asn Pro Cys Tyr
1385            1390               1395

Asn Gln Gly Thr Cys Glu Pro Thr Ser Glu Ser Pro Phe Tyr Arg
1400            1405               1410

Cys Leu Cys Pro Ala Lys Phe Asn Gly Leu Leu Cys His Ile Leu
1415            1420               1425

Asp Tyr Ser Phe Gly Gly Gly Ala Gly Arg Asp Ile Pro Pro Pro
1430            1435               1440

Leu Ile Glu Glu Ala Cys Glu Leu Pro Glu Cys Gln Glu Asp Ala
1445            1450               1455
```

```
Gly Asn Lys Val Cys Ser Leu Gln Cys Asn Asn His Ala Cys Gly
1460             1465                 1470

Trp Asp Gly Gly Asp Cys Ser Leu Asn Phe Asn Asp Pro Trp Lys
1475             1480                 1485

Asn Cys Thr Gln Ser Leu Gln Cys Trp Lys Tyr Phe Ser Asp Gly
1490             1495                 1500

His Cys Asp Ser Gln Cys Asn Ser Ala Gly Cys Leu Phe Asp Gly
1505             1510                 1515

Phe Asp Cys Gln Arg Ala Glu Gly Gln Cys Asn Pro Leu Tyr Asp
1520             1525                 1530

Gln Tyr Cys Lys Asp His Phe Ser Asp Gly His Cys Asp Gln Gly
1535             1540                 1545

Cys Asn Ser Ala Glu Cys Glu Trp Asp Gly Leu Asp Cys Ala Glu
1550             1555                 1560

His Val Pro Glu Arg Leu Ala Ala Gly Thr Leu Val Val Val Val
1565             1570                 1575

Leu Met Pro Pro Glu Gln Leu Arg Asn Ser Ser Phe His Phe Leu
1580             1585                 1590

Arg Glu Leu Ser Arg Val Leu His Thr Asn Val Val Phe Lys Arg
1595             1600                 1605

Asp Ala His Gly Gln Gln Met Ile Phe Pro Tyr Tyr Gly Arg Glu
1610             1615                 1620

Glu Glu Leu Arg Lys His Pro Ile Lys Arg Ala Ala Glu Gly Trp
1625             1630                 1635

Ala Ala Pro Asp Ala Leu Leu Gly Gln Val Lys Ala Ser Leu Leu
1640             1645                 1650

Pro Gly Gly Ser Glu Gly Gly Arg Arg Arg Arg Glu Leu Asp Pro
1655             1660                 1665

Met Asp Val Arg Gly Ser Ile Val Tyr Leu Glu Ile Asp Asn Arg
1670             1675                 1680

Gln Cys Val Gln Ala Ser Ser Gln Cys Phe Gln Ser Ala Thr Asp
1685             1690                 1695

Val Ala Ala Phe Leu Gly Ala Leu Ala Ser Leu Gly Ser Leu Asn
1700             1705                 1710

Ile Pro Tyr Lys Ile Glu Ala Val Gln Ser Glu Thr Val Glu Pro
1715             1720                 1725

Pro Pro Pro Ala Gln Leu His Phe Met Tyr Val Ala Ala Ala Ala
1730             1735                 1740

Phe Val Leu Leu Phe Phe Val Gly Cys Gly Val Leu Leu Ser Arg
1745             1750                 1755

Lys Arg Arg Arg Gln His Gly Gln Leu Trp Phe Pro Glu Gly Phe
1760             1765                 1770

Lys Val Ser Glu Ala Ser Lys Lys Lys Arg Arg Glu Pro Leu Gly
1775             1780                 1785

Glu Asp Ser Val Gly Leu Lys Pro Leu Lys Asn Ala Ser Asp Gly
1790             1795                 1800

Ala Leu Met Asp Asp Asn Gln Asn Glu Trp Gly Asp Glu Asp Leu
1805             1810                 1815

Glu Thr Lys Lys Phe Arg Phe Glu Glu Pro Val Val Leu Pro Asp
1820             1825                 1830

Leu Asp Asp Gln Thr Asp His Arg Gln Trp Thr Gln Gln His Leu
1835             1840                 1845

Asp Ala Ala Asp Leu Arg Met Ser Ala Met Ala Pro Thr Pro Pro
```

```
            1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
    2015                2020                2025

Lys Ser Ala Leu His Trp Ala Ala Val Asn Val Asp Ala
    2030                2035                2040

Ala Val Val Leu Leu Lys Asn Gly Ala Asn Lys Asp Met Gln Asn
    2045                2050                2055

Asn Arg Glu Glu Thr Pro Leu Phe Leu Ala Ala Arg Glu Gly Ser
    2060                2065                2070

Tyr Glu Thr Ala Lys Val Leu Leu Asp His Phe Ala Asn Arg Asp
    2075                2080                2085

Ile Thr Asp His Met Asp Arg Leu Pro Arg Asp Ile Ala Gln Glu
    2090                2095                2100

Arg Met His His Asp Ile Val Arg Leu Leu Asp Glu Tyr Asn Leu
    2105                2110                2115

Val Arg Ser Pro Gln Leu His Gly Ala Pro Leu Gly Gly Thr Pro
    2120                2125                2130

Thr Leu Ser Pro Pro Leu Cys Ser Pro Asn Gly Tyr Leu Gly Ser
    2135                2140                2145

Leu Lys Pro Gly Val Gln Gly Lys Lys Val Arg Lys Pro Ser Ser
    2150                2155                2160

Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235

Asp Thr His Leu Gly Ile Gly His Leu Asn Val Ala Ala Lys Pro
    2240                2245                2250
```

```
Glu Met Ala Ala Leu Gly Gly Gly Arg Leu Ala Phe Glu Thr
    2255            2260                2265

Gly Pro Pro Arg Leu Ser His Leu Pro Val Ala Ser Gly Thr Ser
    2270            2275                2280

Thr Val Leu Gly Ser Ser Gly Gly Ala Leu Asn Phe Thr Val
    2285            2290                2295

Gly Gly Ser Thr Ser Leu Asn Gly Gln Cys Glu Trp Leu Ser Arg
    2300            2305                2310

Leu Gln Ser Gly Met Val Pro Asn Gln Tyr Asn Pro Leu Arg Gly
    2315            2320                2325

Ser Val Ala Pro Gly Pro Leu Ser Thr Gln Ala Pro Ser Leu Gln
    2330            2335                2340

His Gly Met Val Gly Pro Leu His Ser Ser Leu Ala Ala Ser Ala
    2345            2350                2355

Leu Ser Gln Met Met Ser Tyr Gln Gly Leu Pro Ser Thr Arg Leu
    2360            2365                2370

Ala Thr Gln Pro His Leu Val Gln Thr Gln Gln Val Gln Pro Gln
    2375            2380                2385

Asn Leu Gln Met Gln Gln Gln Asn Leu Gln Pro Ala Asn Ile Gln
    2390            2395                2400

Gln Gln Gln Ser Leu Gln Pro Pro Pro Pro Pro Gln Pro His
    2405            2410                2415

Leu Gly Val Ser Ser Ala Ala Ser Gly His Leu Gly Arg Ser Phe
    2420            2425                2430

Leu Ser Gly Glu Pro Ser Gln Ala Asp Val Gln Pro Leu Gly Pro
    2435            2440                2445

Ser Ser Leu Ala Val His Thr Ile Leu Pro Gln Glu Ser Pro Ala
    2450            2455                2460

Leu Pro Thr Ser Leu Pro Ser Ser Leu Val Pro Val Thr Ala
    2465            2470                2475

Ala Gln Phe Leu Thr Pro Pro Ser Gln His Ser Tyr Ser Ser Pro
    2480            2485                2490

Val Asp Asn Thr Pro Ser His Gln Leu Gln Val Pro Glu His Pro
    2495            2500                2505

Phe Leu Thr Pro Ser Pro Glu Ser Pro Asp Gln Trp Ser Ser Ser
    2510            2515                2520

Ser Pro His Ser Asn Val Ser Asp Trp Ser Glu Gly Val Ser Ser
    2525            2530                2535

Pro Pro Thr Ser Met Gln Ser Gln Ile Ala Arg Ile Pro Glu Ala
    2540            2545                2550

Phe Lys
    2555

<210> SEQ ID NO 3
<211> LENGTH: 802
<212> TYPE: PRT
<213> ORGANISM: Homo sapiens

<400> SEQUENCE: 3

Val Leu Leu Ser Arg Lys Arg Arg Gln His Gly Gln Leu Trp Phe
  1               5                  10                  15

Pro Glu Gly Phe Lys Val Ser Glu Ala Ser Lys Lys Arg Arg Glu
                 20                  25                  30

Pro Leu Gly Glu Asp Ser Val Gly Leu Lys Pro Leu Lys Asn Ala Ser
```

```
                35                  40                  45
Asp Gly Ala Leu Met Asp Asn Gln Asn Glu Trp Gly Asp Glu Asp
            50                  55                  60
Leu Glu Thr Lys Lys Phe Arg Phe Glu Glu Pro Val Val Leu Pro Asp
65                      70                  75                  80
Leu Asp Asp Gln Thr Asp His Arg Gln Trp Thr Gln Gln His Leu Asp
                    85                  90                  95
Ala Ala Asp Leu Arg Met Ser Ala Met Ala Pro Thr Pro Pro Gln Gly
                100                 105                 110
Glu Val Asp Ala Asp Cys Met Asp Val Asn Val Arg Gly Pro Asp Gly
                115                 120                 125
Phe Thr Pro Leu Met Ile Ala Ser Cys Ser Gly Gly Gly Leu Glu Thr
            130                 135                 140
Gly Asn Ser Glu Glu Glu Glu Asp Ala Pro Ala Val Ile Ser Asp Phe
145                 150                 155                 160
Ile Tyr Gln Gly Ala Ser Leu His Asn Gln Thr Asp Arg Thr Gly Glu
                165                 170                 175
Thr Ala Leu His Leu Ala Ala Arg Tyr Ser Arg Ser Asp Ala Ala Lys
                180                 185                 190
Arg Leu Leu Glu Ala Ser Ala Asp Ala Asn Ile Gln Asp Asn Met Gly
            195                 200                 205
Arg Thr Pro Leu His Ala Ala Val Ser Ala Asp Ala Gln Gly Val Phe
210                 215                 220
Gln Ile Leu Ile Arg Asn Arg Ala Thr Asp Leu Asp Ala Arg Met His
225                 230                 235                 240
Asp Gly Thr Thr Pro Leu Ile Leu Ala Ala Arg Leu Ala Val Glu Gly
                    245                 250                 255
Met Leu Glu Asp Leu Ile Asn Ser His Ala Asp Val Asn Ala Val Asp
                260                 265                 270
Asp Leu Gly Lys Ser Ala Leu His Trp Ala Ala Ala Val Asn Asn Val
            275                 280                 285
Asp Ala Ala Val Val Leu Leu Lys Asn Gly Ala Asn Lys Asp Met Gln
290                 295                 300
Asn Asn Arg Glu Glu Thr Pro Leu Phe Leu Ala Ala Arg Glu Gly Ser
305                 310                 315                 320
Tyr Glu Thr Ala Lys Val Leu Leu Asp His Phe Ala Asn Arg Asp Ile
                    325                 330                 335
Thr Asp His Met Asp Arg Leu Pro Arg Asp Ile Ala Gln Glu Arg Met
                340                 345                 350
His His Asp Ile Val Arg Leu Leu Asp Glu Tyr Asn Leu Val Arg Ser
            355                 360                 365
Pro Gln Leu His Gly Ala Pro Leu Gly Gly Thr Pro Thr Leu Ser Pro
        370                 375                 380
Pro Leu Cys Ser Pro Asn Gly Tyr Leu Gly Ser Leu Lys Pro Gly Val
385                 390                 395                 400
Gln Gly Lys Lys Val Arg Lys Pro Ser Ser Lys Gly Leu Ala Cys Gly
                    405                 410                 415
Ser Lys Glu Ala Lys Asp Leu Lys Ala Arg Arg Lys Lys Ser Gln Asp
                420                 425                 430
Gly Lys Gly Cys Leu Leu Asp Ser Ser Gly Met Leu Ser Pro Val Asp
            435                 440                 445
Ser Leu Glu Ser Pro His Gly Tyr Leu Ser Asp Val Ala Ser Pro Pro
450                 455                 460
```

-continued

```
Leu Leu Pro Ser Pro Phe Gln Gln Ser Pro Ser Val Pro Leu Asn His
465                 470                 475                 480

Leu Pro Gly Met Pro Asp Thr His Leu Gly Ile Gly His Leu Asn Val
                485                 490                 495

Ala Ala Lys Pro Glu Met Ala Ala Leu Gly Gly Gly Arg Leu Ala
            500                 505                 510

Phe Glu Thr Gly Pro Pro Arg Leu Ser His Leu Pro Val Ala Ser Gly
            515                 520                 525

Thr Ser Thr Val Leu Gly Ser Ser Gly Gly Ala Leu Asn Phe Thr
    530                 535                 540

Val Gly Gly Ser Thr Ser Leu Asn Gly Gln Cys Glu Trp Leu Ser Arg
545                 550                 555                 560

Leu Gln Ser Gly Met Val Pro Asn Gln Tyr Asn Pro Leu Arg Gly Ser
                565                 570                 575

Val Ala Pro Gly Pro Leu Ser Thr Gln Ala Pro Ser Leu Gln His Gly
            580                 585                 590

Met Val Gly Pro Leu His Ser Ser Leu Ala Ala Ser Ala Leu Ser Gln
        595                 600                 605

Met Met Ser Tyr Gln Gly Leu Pro Ser Thr Arg Leu Ala Thr Gln Pro
    610                 615                 620

His Leu Val Gln Thr Gln Gln Val Gln Pro Gln Asn Leu Gln Met Gln
625                 630                 635                 640

Gln Gln Asn Leu Gln Pro Ala Asn Ile Gln Gln Gln Ser Leu Gln
                645                 650                 655

Pro Pro Pro Pro Pro Gln Pro His Leu Gly Val Ser Ser Ala Ala
            660                 665                 670

Ser Gly His Leu Gly Arg Ser Phe Leu Ser Gly Glu Pro Ser Gln Ala
    675                 680                 685

Asp Val Gln Pro Leu Gly Pro Ser Ser Leu Ala Val His Thr Ile Leu
    690                 695                 700

Pro Gln Glu Ser Pro Ala Leu Pro Thr Ser Leu Pro Ser Ser Leu Val
705                 710                 715                 720

Pro Pro Val Thr Ala Ala Gln Phe Leu Thr Pro Pro Ser Gln His Ser
                725                 730                 735

Tyr Ser Ser Pro Val Asp Asn Thr Pro Ser His Gln Leu Gln Val Pro
            740                 745                 750

Glu His Pro Phe Leu Thr Pro Ser Pro Glu Ser Pro Asp Gln Trp Ser
        755                 760                 765

Ser Ser Ser Pro His Ser Asn Val Ser Asp Trp Ser Glu Gly Val Ser
    770                 775                 780

Ser Pro Pro Thr Ser Met Gln Ser Gln Ile Ala Arg Ile Pro Glu Ala
785                 790                 795                 800

Phe Lys
```

TREATMENT OF SQUAMOUS CELL CARCINOMA

REFERENCE TO RELATED APPLICATIONS

The present application is a continuation-in-part of International Application No. PCT/EP2019/071251, filed Aug. 7, 2019, which claims priority to U.S. provisional application No. 62/715,634, filed Aug. 7, 2018, the entire contents of each of which are incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Feb. 13, 2020, is named UTSCP1483US_ST25.txt and is 39.8 kilobytes in size.

BACKGROUND

1. Field

The present invention relates to a method of predicting the functional impact of NOTCH1 mutations in disease, including selection of the patient predicted to benefit from therapeutic administration with either a PI3K inhibitor or a NOTCH1 targeting agent. Moreover, the present invention relates to a method of treating mammalian cancers, preferably a human patient, through administering a therapeutically effective amount of either a PI3K inhibitor when treating a squamous cell carcinoma (SCC) that harbors a NOTCH1 loss-of-function mutation, or a NOTCH1 inhibitor when treating a liquid or solid tumor that harbors an activating NOTCH1 mutation. The present invention also relates to a method of treating a squamous cell carcinoma (SCC), such as a head and neck SCC, of a mammal, such as a human patient, comprising administering a combined therapeutically effective amount of a PDK1 inhibitor and a PI3K/mTOR pathway inhibitor, when the SCC harbors wild-type NOTCH1.

2. Description of Related Art

More than 90% of tumors in the head and neck are squamous cell carcinomas (HNSCC) (Ferlay et al., 2015; The Cancer Genome Atlas 2015). Head and neck squamous cell carcinoma (HNSCC) is a lethal, disabling, disfiguring cancer and the seventh leading cause of cancer-related deaths globally with more than 375,000 individuals dying from this cancer yearly (Ferlay et al., 2015). In this disease, treatment morbidity is high and recurrence is common. Although immunotherapy has had a striking effect in some patients with metastatic or recurrent HNSCC, the majority of patients still progress. Standard chemotherapy (methotrexate, docetaxel, others) or cetuximab beyond first line therapy benefits less than 15% of patients. Except for Cetuximab, for which there is no biomarker to predict response, there are no molecular targeted therapies approved for treating HNSCC patients, identifying a significant translational knowledge gap. Although the unbiased genomic characterization of multiple cancers has fundamentally changed our approach to cancer therapy and translational research, this revolution has not yet affected therapy for HNSCC and targeted therapy based on biomarkers does not yet exist for HNSCC.

Recent genomic characterization of HNSCC by several independent groups has demonstrated remarkable complexity but also four common driver-signaling pathways (Agrawal et al., 2011; Stransky et al., 2011; Iglesias-Bartolome et al., 2013; Pickering et al., 2013). Of the mitogenic pathways affected, the PI3K/AKT/mTOR pathway is the most often altered in HNSCC, with ~80% of HNSCC tumors containing molecular alterations in one or more components of the pathway (Iglesias-Bartolome et al., 2013; Lui et al., 2013). In HNSCC, the PI3K/mTOR pathway is altered in 54% of patients including copy number alterations in PIK3CA (35%), PTEN (6%), RICTOR (7%), AKT1 (3%), PIK3R1 (2%), and MTOR (3%) (Cerami et al., 2012). In particular PIK3CA is the third most frequently altered gene (18%) in HNSCC with frequent hotspot mutations in the helical (E542K or E545K) and kinase (H1047R) domains in human papilloma virus (HPV)-negative HNSCC patients and mutations in the helical domain in HPV-positive HNSCC patients (Iglesias-Bartolome et al., 2013). Clinical responses to PI3K/AKT/mTOR pathway inhibitors have been modest and short-lived in most solid tumors (Rodon et al., 2013; Fruman & Rommel, 2014) and there are no biomarkers to guide patient selection (Fruman & Rommel, 2014). Use of PIK3CA mutation as a biomarker is inconclusive, with studies showing both increased sensitivity (Di Nicolantonio et al., 2010; Lui et al., 2013) and no differential response to PI3K/AKT/mTOR inhibitors in clinical trials (Janku et al., 2011; Janku et al., 2012; Jimeno et al., 2015). Consistent with the clinical findings, HNSCC cell lines and patient derived xenografts (PDXs) with PIK3CA mutations were more sensitive to PI3K/mTOR pathway inhibitors than PIK3CAWT HNSCC cells but these drugs led to only cell-cycle arrest with no apoptosis in the mutant cell lines (Lui et al., 2013; Mazumdar et al., 2014; Jimeno et al., 2015). The frequent activation of the PI3K/AKT/mTOR pathway in HNSCC, the availability of pharmacologic inhibitors and the pathway's importance in cancer cell signaling make this pathway a promising target for needed improved systemic therapy and to identify potential targetable alterations within this pathway (Mazumdar et al., 2014).

NOTCH1 can function in cancer as either a tumor suppressor or oncogene depending upon the tissue specific context (Mao, 2015; Nowell & Radtke, 2017). NOTCH family receptors regulate cell fate decisions, lineage commitment, and differentiation (Mao, 2015; Nowell & Radtke, 2017). Humans have four NOTCH family receptors (NOTCH1-4) which are activated in a juxtacrine manner by any of five canonical ligands (Jagged-1, -2, Delta-like ligand 1, -3, and -4) expressed on neighboring cells (D'Souza et al., 2008; Agrawal et al., 2011). Aberrant NOTCH signaling has been implicated in the development, progression, and prognosis of many cancer types. However, actual genomic alterations to NOTCH family receptor genes mainly occur in NOTCH1, and are found frequently in only some tumor types, including T-cell acute leukemia (T-ALL) (Ferrando, 2009), adenoid cystic carcinoma (ACC) (Ho et al., 2013; Ferrarotto et al., 2017), and squamous cell carcinomas of the head and neck (Pickering et al., 2013), skin (Pickering et al., 2014), esophagus (Agrawal et al., 2012), and lung (The Cancer Genome Atlas 2015). NOTCH1 receptors are expressed after cleavage of a larger NOTCH1 precursor protein into extracellular and intracellular peptides that heterodimerize at the cell surface through specific heterodimerization domains (HDs) (Nowell & Radtke, 2017). Ligand binding to the extracellular EGF-like repeats on NOTCH1 receptors creates mechanical tension exposing the molecule to stepwise cleavage at the S2 site by α-secretases and finally at the S3 cleavage site by γ-secretase to release intracellular cleaved NOTCH1 (cl-NOTCH1; NOTCH1 intracellular domain=NCID1). cl-NOTCH1 translocates to the nucleus and binds other transcription co-factors, altering expression of genes (Nowell & Radtke, 2017).

NOTCH1 is among the top five most frequently mutated genes in HNSCC (Stransky et al., 2011; The Cancer Genome Atlas 2015) and NOTCH1 mutations occur at high frequency of about 20% in untreated and recurrent HNSCC (Cancer Genome Atlas Research, 2013; Morris et al., 2017). Recently, it has been described that NOTCH1 inactivating mutation mediates sensitivity to PI3K/mTOR inhibition in HNSCC and that HNSCC cell lines harboring NOTCH1 mutation underwent apoptosis after PI3K/mTOR pathway inhibition in vitro and decreased tumor size in vivo (Johnson et al., 2016; Sambandam et al., 2017; Sambandam et al., 2018).

Taken all of the above into consideration, there is an urgent need for developing a biomarker-based targeted therapy for the treatment of SCCs, in particular for HNSCC, which enables selection and treatment of patients with SCCs, in particular HNSCC, which are likely to benefit from said therapy, thus creating a positive risk/benefit ratio for patients.

In different cancer types, including but not limited to T-ALL (Ferrando, 2009), and ACC (Ho et al., 2013; Ferrarotto et al., 2017), NOTCH1 functions instead as an oncogene rather a tumor suppressor gene. Drugs inhibiting NOTCH1 have anti-tumor activity in mouse xenograft models of ACC harboring activating NOTCH mutations and in human ACC patients whose tumors have activating NOTCH1 mutations (Ferrarotto et. al., 2019). Activating driver NOTCH1 mutations are frequently found in T-ALL and treating leukemia patients harboring these activating NOTCH1 mutations with safe drugs to inhibit NOTCH1 function is an active area of clinical research (Habets, et. al., 2019).

SUMMARY

In one embodiment, provided herein are methods of treating a patient having a squamous cell carcinoma (SCC), the method comprising administering to the patient a therapeutically effective amount of a PI3K inhibitor, wherein the SCC has a NOTCH1 loss-of-function (LOF) mutation. In some aspects, the methods comprise (a) determining or having determined whether the SCC has a NOTCH1 LOF mutation; (b) selecting or having selected the patient for treatment with a PI3K inhibitor when the SCC has NOTCH1 LOF mutation; and (c) administering or having administered to the selected patient a therapeutically effective amount of a PI3K inhibitor.

In some aspects, step (a) comprises (i) obtaining or having obtained a biological sample from the SCC; and (ii) performing or having performed an assay on the biological sample to determine whether the SCC has one or more mutations in the NOTCH1 gene or a decreased protein level of cleaved NOTCH1 intracellular domain. In some aspects, the assay comprises sequencing the NOTCH1 gene in the SCC. In some aspects, the assay further comprises comparing the sequence of the NOTCH1 gene in the SCC to the sequence of the wild-type NOTCH1 gene. In some aspects, the wild-type NOTCH1 gene has the sequence of SEQ ID NO: 1. In some aspects, the wild-type NOTCH1 gene has a sequence determined by sequencing the NOTCH1 gene in a sample obtained from healthy or non-cancerous tissue in the patient. In some aspects, the one or more mutation(s) in the NOTCH1 gene is not a mutation in the TAD domain or in the PEST domain of the NOTCH1 gene, a missense or an in-frame mutation, or a mutation in the splice donor boundary (Exon 33) or the splice acceptor boundary (Exon 34) of the NOTCH1 gene. In some aspects, the mutation in the NOTCH1 gene is not within nucleotides 6477-7665 of SEQ ID NO:1. In some aspects, the mutation in the NOTCH1 gene is not within nucleotides 4326-5202 of SEQ ID NO:1. In some aspects, the mutation in the NOTCH1 gene is not within nucleotides 5639-6082 of SEQ ID NO:1.

In some aspects, the assay comprises determining a protein level of cleaved NOTCH1 intracellular domain in the SCC. In some aspects, the protein level of cleaved NOTCH1 intracellular domain in the SCC is the protein level of cleaved NOTCH1 intracellular domain in the nuclei of the SCC cells. In some aspects, the assay further comprises comparing the protein level of cleaved NOTCH1 intracellular domain in the SCC to the level of cleaved NOTCH1 intracellular domain in a reference sample. In some aspects, the reference sample is non-cancerous tissue from the patient. In some aspects, the reference sample is obtained from a healthy subject. In some aspects, a decreased protein level of cleaved NOTCH1 intracellular domain in the SCC relative to the level of cleaved NOTCH1 intracellular domain in a reference sample indicates that the SCC has a NOTCH1 LOF mutation.

In some aspects, the PI3K inhibitor is a PI3K/mTOR inhibitor. In some aspects, the squamous cell carcinoma is a head and neck squamous cell carcinoma (HNSCC), a skin squamous cell carcinoma, an esophagus squamous cell carcinoma, or a lung squamous cell carcinoma. In some aspects, the patient is a human.

In one embodiment, provided herein are methods of treating a patient having a squamous cell carcinoma (SCC), the method comprising administering to the patient a combined effective amount of a PDK1 inhibitor and another PI3K/mTOR pathway inhibitor. In some aspects, the patient's SCC cells has a wild-type NOTCH1 gene. In some aspects, the squamous cell carcinoma is a head and neck squamous cell carcinoma (HNSCC), a skin squamous cell carcinoma, an esophagus squamous cell carcinoma, or a lung squamous cell carcinoma. In some aspects, the patient is a human. In some aspects, the method inhibits the survival or proliferation of the patient's SCC cells. In some aspects, the PI3K/mTOR pathway inhibitor is a PI3K inhibitor. In some aspects, the PI3K/mTOR pathway inhibitor is an AKT inhibitor. In some aspects, the methods are methods of sensitizing the patient's SCC cells to the PI3K/mTOR pathway inhibitor. In some aspects, the methods further comprise administering a further anti-cancer therapy to the patient. In some aspects, the further anti-cancer therapy is a surgical therapy, chemotherapy, radiation therapy, cryotherapy, hormonal therapy, toxin therapy, immunotherapy, or cytokine therapy.

The present invention provides a method of predicting the vulnerability of squamous cell carcinoma (SCC) to inhibition by a PI3K inhibitor, preferably based on a specific selection of biomarkers in association with NOTCH1 mutations harbored in said SCCs, which mutations are considered to lead to loss of function (LoF). The present invention thus provides a novel targeted therapy for treating SCC of a mammal, preferably of a human patient, in particular for treating head and neck SCC (HNSCC) in human patients that have been selected as to benefit from said targeted therapy. In addition, the present invention provides a method of predicting the vulnerability of other tumor types with activating NOTCH1 mutations to drugs blocking NOTCH1 function. In detail, the present invention preferably relates to targeting SCC harboring specific NOTCH1 mutations considered to be loss of function (LoF), and in particular HNSCC harboring said specific NOTCH1 LoF mutations. The present invention also relates to targeting other solid and liquid tumor types harboring specific NOTCH1 mutations considered to be activating harboring said specific NOTCH1 gain of function mutations.

The prediction of the vulnerability of SCC, in particular HNSCC, and the selection criteria of the mammal, preferably human patients predicted to benefit from the targeted therapy in accordance with the present invention is, in particular, based on the occurrence, nature and distribution pattern of NOTCH1 mutations and the inventive specific selection of NOTCH1 mutations considered to be loss of function (LoF) mutations in accordance with the present invention. In particular, the present invention identifies specific selection criteria for said NOTCH1 mutations to predict the vulnerability of SCC, in particular HNSCC, and to predict the increased efficacy of a PI3K inhibitor for the treatment of SCC, in particular HNSCC.

The prediction of the vulnerability of solid and liquid tumors, in particular T-ALL and ACC, and the selection criteria of the mammal, preferably human patients predicted to benefit from the targeted therapy in accordance with the present invention is, in particular, based on the occurrence, nature and distribution pattern of NOTCH1 mutations and the inventive specific selection of NOTCH1 mutations considered to activating mutations in accordance with the present invention. In particular, the present invention identifies specific selection criteria for said NOTCH1 mutations to predict the vulnerability of cancers, and to predict the increased efficacy of NOTCH1 targeting agents, in particular for T-ALL and ACC.

In summary, the present invention establishes a biomarker-based targeted therapy for the treatment of SCCs and in particular for HNSCC that facilitate selection and treatment of patients with SCCs and in particular HNSCC which are likely to benefit from the inventive treatment. In addition, the present invention also establishes a biomarker useful for treatment of cancers driven by activating NOTCH1 mutations. The present invention, thus, advantageously and preferably, creates a favorable risk-benefit ratio for the mammal, preferably human patients by limiting said inventive treatment to said patients that will likely benefit from treatment using the principles of personalized medicine.

Further aspects and embodiments of the present invention will be become apparent as this description continues.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 6A-6F: NOTCH1 loss-of-function (LOF) mutations and NOTCH1 signaling in head and neck squamous cell carcinoma (HNSCC) are correlated with sensitivity to PI3K/mTOR pathway inhibitors. FIG. 6A: HNSCC cell lines (n=59) were incubated with seven different PI3K/mTOR pathway inhibitors. The drugs' $IC_{70}$ and area under the curve (AUC) values in wild type cell lines were compared with those in cell lines with mutations in 33 common driver genes using a modified two-sample t-test at a false discovery rate (FDR) of 0.05. Positive and negative correlations between the presence of a mutation and drug sensitivity are indicated by blue and red data points, respectively, with larger points representing significant differences. FIG. 6B: The $IC_{70}$ values in cell lines with wild type or mutant NOTCH1 and PIK3CA were compared using a Kruskal-Wallis test corrected for multiple comparisons by the Dunn test; p values are indicated in the figure. The dashed black lines indicate each drug's peak plasma concentration. N.S., not significant. FIG. 6C: The frequency and location of mutations in NOTCH1 in HNSCC cell lines (upper gene map) are compared with those of T-acute lymphoblastic leukemia (T-ALL; lower map, below the gene) and HNSCC patients (upper map, above the gene) based on data from the Catalogue of Somatic Mutations in Cancer and The Cancer Genome Atlas (TCGA). Oncogenic T-ALL NOTCH1 mutations occur in a hotspot of mostly missense mutations within the negative regulatory heterodimerization (NRD) domain or in a second hotspot of mostly truncating mutations near the C-terminus, deleting the proline-glutamic acid-serine-threonine (PEST) domain and increasing the stabilization of activated NOTCH1 in the nucleus. In contrast, the truncating mutations in HNSCC are scattered throughout the gene but not in the PEST domain, and the missense mutations cluster in the extracellular EGF ligand-binding domains. FIG. 6D: Most mutations in the NOTCH1 gene in TCGA HNSCC patient samples are missense mutations outside the C-terminal NRD and PEST domains. FIG. 6E: From our panel of 59 HNSCC cell lines, we identified 24 harboring NOTCH1 and/or PIK3CA mutations. Orange text corresponds to nonsense mutations outside the PEST domain; red text, frameshift mutations outside the PEST domain; blue text, missense mutations outside the NRD and PEST domains; and gray text, in-frame deletions. ¥Non-canonical mutations; †suspected single-nucleotide polymorphisms excluded from NOTCH1 LOF mutants. FIG. 6F: The basal expression levels of NOTCH1 and NOTCH intracellular domain (NICD) proteins in $NOTCH1^{WT}$ and $NOTCH1^{MUT}$ cell lines were compared using a two-sample t-test. The correlation between the expression levels of NICD and NOTCH1 was assessed by Spearman correlation.

FIG. 7A. Annexin V/propidium iodide or BrDU-terminal deoxynucleotidyl transferase (TdT) dUTP nick-end labeling (TUNEL) assays were used to measure apoptosis in HNSCC cells with the indicated NOTCH1 and PIK3CA mutations, which were treated with 50 nM GSK2126458 (GSK212) for 24 or 48 hours, respectively. Values are the means±standard deviations of three independent experiments. $*p<0.05$, unpaired two-tailed Student t-test. FIG. 7B. Western blotting of cleaved PARP (Cl-PARP) and cleaved caspase 3 (Cl-Caspase 3) levels in mutant and wild type cells after GSK212 treatment for 48 hours. FIG. 7C. $NOTCH1^{MUT}$ and $NOTCH1^{WT}$ HNSCC cells were plated sparsely and treated with GSK212 at the indicated concentrations for 48 hours. At 14-21 days after treatment, the cells were fixed and stained, images were captured using the GelCount Tumour Colony Counter, and colony numbers and the colorimetric intensity of the colonies were determined by measuring the optical density (OD) at 570 nm. Values are the means±standard deviations of three independent experiments. $*p<0.001$, unpaired two-tailed Student t-test. FIG. 7D. Three $NOTCH1^{WT}$ lines (black text and bars) and three $NOTCH1^{MUT}$ lines (red text and bars) were treated with increasing concentrations of GSK212 for 4 hours, and levels of PI3K/mTOR pathway proteins were measured by Western blot analysis.

FIGS. 8A and 8B. The $NOTCH1^{MUT}$ cell lines HN31 (FIG. 8A) and UMSCC22A (UM22A; FIG. 8B) were injected subcutaneously (SQ) into athymic nude mice. After tumors reached 150 mm³, the mice were randomized to receive either vehicle control (2-hydroxypropyl-β-cyclodextrin) or 1 mg/kg GSK2126458 (GSK212) by oral gavage daily for 28 days. Tumor sizes were measured and tumor volumes were calculated at the indicated times, and the percent change in tumor volume at the end of therapy was calculated using the formula (final tumor volume−initial tumor volume/initial tumor volume)×100%. The percentages of TUNEL-positive cells were calculated from image quantification at 40× magnification. FIGS. 8C and 8D. HN31 (FIG. 8C) and UM22A (FIG. 8D) were implanted orthotopically (OT) into the anterior tongues of athymic nude mice. After tumors reached 1.5-2.0 mm³, the mice were randomized to receive either vehicle control (16% 2-hydroxypropyl-β-cyclodextrin for GSK212) or GSK212 (3 mg/kg) by oral gavage daily for 28 days. Tumor sizes were measured, and tumor volumes and percent changes in tumor volumes were calculated as above. For the tumor growth curve analysis, we applied a linear model using generalized least squares with two variables (treatment and day) and an autocorrelation structure of order 1 in residuals. The percentages of TUNEL-positive cells were calculated as described above. Data are means±standard deviations from 5 mice per group; p values were calculated using an unpaired t-test with the Welch correction.

FIG. 9A. The CellTiter-Glo assay was used to assess the viability of cells treated for 72 hours with the indicated concentrations of GSK2126458 (GSK212). FIG. 9B. Western blot analysis of apoptosis markers, NOTCH1, and NOTCH intracellular domain (NICD) was performed after treatment with the indicated concentrations of GSK212 for 48 hours. FIG. 9C. Apoptosis in cells treated with 50 nM GSK212 or 200 nM BEZ235 for 48 hours was measured using an Annexin V/propidium iodide assay. Values are the means±standard deviations of three independent experiments. $*p<0.05$, unpaired two-tailed Student t-test. FIG. 9D. Cells were treated with 50 nM GSK212 for 48 hours and then incubated in drug-free medium for 14-21 days. Colony areas as percentages of the control were measured using ImageJ. Data are presented as the means±standard deviations of three independent experiments. *p<0.05, unpaired two-tailed Student t-test.

FIG. 10A. Two NOTCH1$^{WT}$ lines and four NOTCH1$^{MUT}$ lines were treated with 50 nM GSK2126458 (GSK212) for 24 hours and then subjected to Western blot analysis with the indicated antibodies to assess the expression of 3-phosphoinositide dependent kinase 1 (PDK1) and phosphorylated PDK1. FIG. 10B. Protein expression from Western blotting was quantified using ImageJ and normalized using β-actin as a control, and the relative fold control from untreated was calculated. Bars indicate means±standard errors of the means from two NOTCH1$^{WT}$ cell lines and four NOTCH1$^{MUT}$ cell lines. *p<0.05, one-tailed Student t-test. FIG. 10C. We established NOTCH1$^{MUT}$ lines (HN31, PCI15B, and UMSCC22A) with PDK1 overexpression, which was confirmed by Western blot analysis. FIGS. 10D and 10E. Parental and PDK1-overexpressing NOTCH1$^{MUT}$ cells were treated with 50 nM GSK212 for 24 or 48 hours, and apoptosis was assessed by measuring levels of cleaved PARP (Cl-PARP) and cleaved caspase 3 (Cl-Caspase 3) by Annexin V/propidium iodide assay (FIG. 10D) and Western blot analysis (FIG. 10E). The percentage of apoptotic cells are expressed as the means±standard deviations of three independent experiments. *p<0.001, two-way ANOVA corrected for multiple comparisons by the Tukey test.

FIG. 11B. NOTCH1$^{WT}$ (black text) and NOTCH1$^{MUT}$ (red text) HNSCC cells were treated with 50 nM GSK2126458 (GSK212), 10 µM GSK233, 10 µM MK2206, or the GSK233-MK2206 combination for 48 hours. Western blot analysis showed that the combination increased cleaved PARP (Cl-PARP) and cleaved caspase 3 (Cl-Casp3) in the NOTCH1$^{WT}$ lines. FIG. 11C. Four NOTCH1$^{WT}$ HNSCC cell lines were treated with 50 nM GSK212, 10 µM GSK233, 10 µM MK2206, or the GSK233-MK2206 combination for 48 hours. Apoptosis was measured by Annexin V/propidium iodide assay, and the percentages of apoptotic cells are expressed as the means±standard deviations of three independent experiments. *p<0.001, **p<0.05, two-way analysis of variance corrected for multiple comparisons with the Tukey test.

FIG. 12A. HNSCC cell lines (n=59) were incubated with seven PI3K/mTOR pathway inhibitors. FIG. 12B. The 70% inhibitory concentration ($IC_{70}$) values for each drug were plotted. Each data point represents one cell line. FIG. 12C. Spearman correlation analysis was used to assess the association of each drug's $IC_{70}$ value with those of the other drugs. The drugs included seven PI3K/mTOR pathway inhibitors (red text) and three cell cycle kinase inhibitors (blue text). The heat map shows the Spearman correlation values for each drug combination; unsupervised clustering showed that all PI3K/mTOR pathway inhibitors exhibited similar sensitivity patterns.

FIG. 13A. The basal protein expression levels of NOTCH1 were compared between NOTCH1WT (n=170) and NOTCH1MUT (n=38) tumors available in The Cancer Genome Atlas (TCGA) using a two-sample t-test. FIGS. 13B-13E. Basal NOTCH1 (FIGS. 13B and 13E) and NOTCH intracellular domain (NICD) (FIGS. 13C and 13D) protein expression was compared with drug sensitivity as measured by area under curve (AUC) for all 59 HNSCC cell lines (FIGS. 13B and 13C), NOTCH1WT cells only (n=45) (FIG. 13D), and with NOTCH1MUT cells only (n=14) (FIG. 13E). P values were calculated with Spearman rho correlation analysis. The dashed blue lines indicate trend line and the shaded area represent 95% confidence interval.

FIG. 14B. Spearman correlation analysis was used to assess associations between $IC_{70}$ values and PI3K proteomic scores, including for p-AKT (T308), p-AKT (S473), p-GSK3 (S9), p-GSK3-Î±/Î² (S9/21), p-p27 (T157), p-p27 (T198), p-PRAS40 (T246), INPP4B, and PTEN; no significant correlations were detected. FIG. 14C. Spearman correlation analysis was used to assess associations between $IC_{70}$ values and mTOR proteomic scores, including for Tp-4EBP1 (S65), p-4EBP1 (T37/46), p4EBP1 (T70), p-mTOR (S2488), p-p70S6K (T389), p-S6 (S235/236), and p-S6 (S240/244); no significant correlations were detected. The dashed blue lines indicate trend line and the shaded area represent 95% confidence interval.

FIGS. 15A and 15B. The sensitivity of HPV-positive cells to each drug using area under curve (AUC) values (FIG. 15A) or 70% inhibitory concentration ($IC_{70}$) values (FIG. 15B) was compared with that of HPV-negative cells; no significant differences were found. P values were calculated using a two-sample t-test. FIGS. 15C-15D. Spearman correlation analysis was used to assess associations between $IC_{70}$ values and epithelial to mesenchymal (EMT) and DNA repair proteomic scores with the indicated p values. The dashed blue lines indicate trend line, the red lines indicate local regression line (LOWESS line) and the shaded area represent 95% confidence interval.

FIG. 16A. The Annexin V/propidium iodide assay was used to assess apoptosis in HNSCC cells that had the indicated NOTCH1 and PIK3CA mutations and were treated with 500 nM BAY806946. Values are the means {plus minus} standard deviations of three independent experiments. *p>0.05, unpaired two-tailed Student t-test. FIG. 16B. NOTCH1MUT lines (red text) and NOTCH1WT lines (black text) were treated with increasing concentrations of BAY806946 for 3 hours, and then Western blotting was used to assess levels of p-AKT (S473). FIG. 16C. NOTCH1WT lines (black text), NOTCH1MUT lines (red text), and PIK3CAMUT lines (blue text) were treated with 50 nM GSK2126458 (GSK212) and then pulse-labeled with BrDU and counterstained with 7-AAD for flow cytometry.

FIGS. 17A and 17B. The CellTiter-Glo assay was used to assess the viability of cells treated for 72 hours with the indicated concentrations of GSK212. FIGS. 17C and 17D. Annexin V/propidium iodide staining was used to assess the apoptosis of cells treated with 50 nM GSK212 for 48 hours. Values are the means {plus minus} standard deviations of three independent experiments; n.s., not significant, unpaired two-tailed Student t-test. FIG. 17E. Western blot analysis of apoptotic markers was performed after treatment with the indicated concentrations of GSK212 for 48 hours.

FIG. 18A. Four NOTCH1WT HNSCC cell lines were treated with the indicated concentrations of GSK2126458 (GSK212) and 20 µM N—[N-(3,5-difluorophenacetyl-L-alanyl)]-S-phenylglycine t-butyl ester (DAPT) or 20 µM dibenzazepine (DBZ) for 72 hours, and cell viability was assessed with the CellTiter-Glo assay. Representative dose-response curves are shown. FIG. 18B. The combination index (CI) for each fraction affected (Fa) was calculated using the Chou-Talalay method. FIG. 18C. Western blotting for apoptosis markers after treatment with 50 nM GSK212 and 20 µM DAPT for 48 hours. FIGS. D and E. NOTCH1WT cells were treated with 50 nM GSK212 and 20 µM DBZ or DAPT for 48 hours, and apoptosis was measured using an Annexin V/propidium iodide assay. The percentages of apoptotic cells are expressed as the means {plus minus} standard deviations of three independent experiments. *>0.001, **p>0.05, two-way ANOVA corrected for multiple comparisons by the Tukey test; ns, not significant.

FIG. 19A. NOTCH1MUT cells (red text) and NOTCH1WT cells (black text) were treated with increasing concentrations (0-200 nM, 2-fold dilution) of GSK2126458 (a dual PI3K/mTOR inhibitor), BAY806946 (a pan-PI3K inhibitor), rapamycin and ridaforolimus (two mTOR inhibitors), and MK2206 (an AKT inhibitor) for 72 hours, and cell viability was assessed using the CellTiter-Glo assay. FIG. 19B. The protein p-S6 (S240/244) bands in FIG. 2D were quantified using ImageJ software and normalized to $î^2$-actin expression, and the fold change from the control was calculated. Data are the means {plus minus} standard errors for three cell lines. *p>0.05, unpaired one-tailed Student t-test.

FIG. 20A. Two NOTCH1WT lines and four NOTCH1MUT lines were treated with 100 nM BAY806946 for 24 hours and then subjected to Western blot analysis with the indicated antibodies. FIG. 20B. Parental and PDK1-overexpressing NOTCH1MUT cells were treated with 50 nM GSK212 for 24 hours and then subjected to Western blot analysis with the indicated antibodies. FIG. 20C. Three NOTCH1MUT HNSCC lines were treated with increasing concentrations (0-10 µM, 2-fold dilution) of MK2206 and/or GSK2334470 for 72 hours, and cell viability was assessed using the CellTiter-Glo assay. FIG. 20D. The combination index (CI) for the fractions affected (Fa) for each combination was calculated with the Chou Talalay method using Calcusyn (Biosoft, Cambridge, UK).

DETAILED DESCRIPTION

Figure 1:
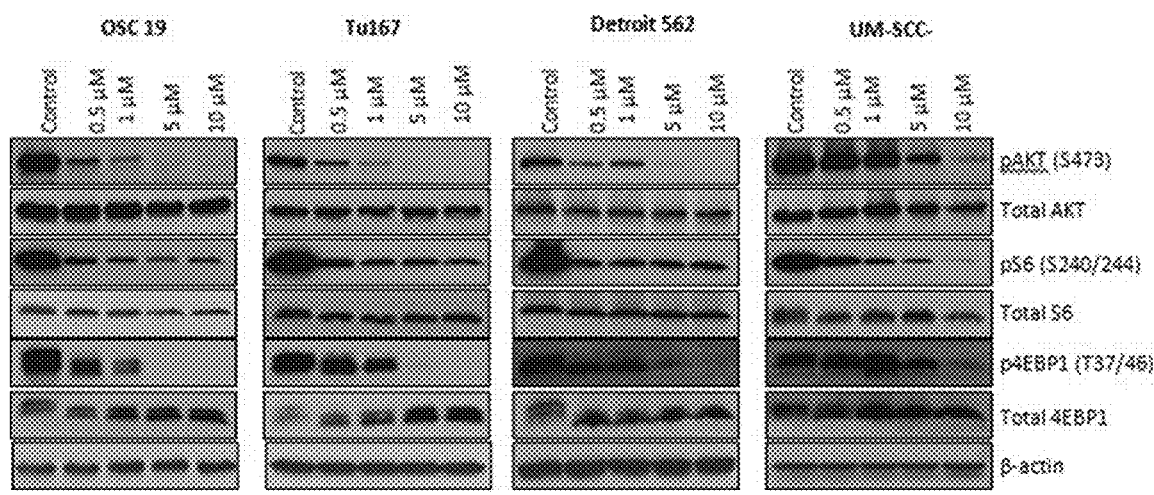
FIG. 1: Bimiralisib inhibits PI3K pathway signaling in HNSCC. Four HNSCC cell lines were treated with the indicated concentrations of bimiralisib for 2 hours. Cells were lysed and then resolved by SDS PAGE. Western blot analysis was performed using the indicated antibodies.

Although head and neck squamous cell carcinoma (HNSCC) has a high mutation rate, genomic sequencing has not detected druggable driver mutations in the disease. Rather, HNSCC is dominated by mutations in non-targetable tumor suppressor genes such as TP53 (72%), NOTCH1 (18%), KMT2D (16%), and AJUBA (6%) (Cancer Genome Atlas, 2015; Agrawal et al., 2011). The most frequently altered mitogenic signaling pathway in HNSCC is the phosphoinositide 3-kinase (PI3K)/mammalian target of rapamycin (mTOR) pathway, with 54% of patients having mutations or copy number alterations in PIK3CA (35%), PTEN (6%), RICTOR (7%), AKT1 (3%), PIK3R1 (2%), and MTOR (3%) (Iglesias-Bartolome et al., 2013). PIK3CA, the third most frequently mutated gene in HNSCC (18%), has frequent hotspot mutations in the helical (E542K or E545K) and kinase (H1047R) domains (Iglesias-Bartolome et al., 2013; Lui et al., 2013).

PI3K signaling and its effectors protein kinase B (AKT), mTOR, and phosphoinositide-dependent kinase 1 (PDK1), which play critical roles in cell proliferation and survival, are validated therapeutic targets in other cancers (Rodon et al., 2017). With the exception of PI3K inhibitors that are approved for the treatment of hematologic malignancies and target of rapamycin complex 1 (TORC1) inhibitors that are approved for renal cell carcinoma, PI3K/AKT/mTOR inhibitors have elicited only modest response rates in solid tumors (Rodon et al., 2017). Strategies guiding the selection of patients for these agents also remain elusive. Whether PIK3CA mutant (PIK3CA$^{MUT}$) tumors have increased sensitivity to PI3K/AKT/mTOR inhibitors is unclear (Lui et al., 2013; Janku et al., 2012; Jimeno et al., 2015). PI3K/AKT/mTOR inhibitors have a low clinical response rate in PIK3CA$^{MUT}$ tumors (~30%) (Janku et al., 2012) compared with other targeted therapies, such as the epidermal growth factor receptor inhibitor osimertinib, which has a response rate of about 80% in EGFR$^{MUT}$ lung cancers (Soria et al., 2018). Consistent with these clinical findings, PIK3CA$^{MUT}$ HNSCC cell lines and patient-derived xenografts (PDXs) are more sensitive to PI3K/mTOR pathway inhibitors than PIK3CA wild type (PIK3CA$^{WT}$) HNSCC cells are; however, the drugs cause only cell-cycle arrest with no apoptosis in the mutant cell lines (Lui et al., 2013; Mazumdar et al., 2014; Keysar et al., 2013; Li et al., 2014; Elkabets et al., 2015).

Molecular therapies targeting activated oncogenes are common, but only one such therapy has been approved for cancers driven by the loss of tumor suppressor function: poly (ADP-ribose) polymerase (PARP) inhibitors for BRCA1/BRCA2$^{MUT}$ breast cancer (Tutt et al., 2010). Perhaps because of feedback pathways, targeting pathways activated downstream of tumor suppressors has not been effective for cancer therapy. To date, the new genomic information available for this disease has not been translated into clinical care largely because the genomic landscape is dominated by tumor suppressors. In this study, the hypothesis that an unbiased pharmacogenomics approach would identify novel, translationally applicable molecular vulnerabilities to HNSCC with the loss of tumor suppressor function was tested. To address the lack of effective molecularly targeted therapies for HNSCC, an unbiased pharmacogenomics approach was used to integrate drug sensitivity data for seven diverse PI3K/mTOR pathway inhibitors in a panel of 59 molecularly characterized HNSCC cell lines (Kalu et al., 2017; Zhao et al., 2011). A striking correlation was identified between NOTCH1 loss of function (LOF) mutations and sensitivity to PI3K/mTOR pathway inhibitors in HNSCC that was confirmed with both in vitro and in vivo studies.

The data provided herein establish a therapeutic vulnerability of NOTCH1$^{MUT}$ HNSCC to PI3K inhibitors. Thus, these findings have the potential to advance the approval of a biomarker-driven targeted therapy for HNSCC. Further, based on the mechanism of sensitivity of NOTCH1$^{MUT}$ HNSCC (i.e., a cell line or tumor having a NOTCH1 mutation), a combination therapy has been identified that may be effective against NOTCH1$^{WT}$ HNSCC.

I. ASPECTS OF THE PRESENT INVENTION

With the data provided herein, NOTCH1 LOF mutations in HNSCC are now established as a significant therapeutic vulnerability to PI3K/mTOR pathway inhibition. Unlike PIK3CA$^{MUT}$ HNSCC cell lines, which underwent only cell cycle arrest following PI3K/mTOR pathway inhibition, NOTCH1$^{MUT}$ HNSCC cell lines also underwent apoptosis. Likewise, PI3K/mTOR inhibitors decreased NOTCH1$^{MUT}$ HNSCC tumor size in vivo. Selective mTOR or AKT inhibitors did not have differential effects on NOTCH1$^{WT}$ or NOTCH1$^{MUT}$ HNSCC. This led to the examination of PDK1, whose expression decreased following PI3K/mTOR inhibition in only NOTCH1$^{MUT}$ HNSCC, supporting the hypothesis that persistent PDK1 activation leads to PI3K/mTOR inhibition resistance in NOTCH1$^{WT}$ HNSCC despite robust AKT inhibition. Consistent with this hypothesis, a combination of drugs that inhibit both PDK1 and AKT led to apoptosis.

Two other lines of evidence support these conclusions. First, the PI3K inhibitor PX-886 significantly reduced tumor growth in two NOTCH1$^{MUT}$ HNSCC PDX models (Keysar et al., 2013). Second, NOTCH pathway activation confers resistance to PI3K/mTOR inhibitors via c-Myc activation in breast cancer (Muellner et al., 2011). Although basal c-Myc gene or protein expression did not predict response, and c-Myc expression did not differ according to NOTCH1 mutation status, c-Myc may be differentially regulated downstream of PDK1 in a PIP$_3$-independent manner.

Although activating mutations in PIK3CA also occur in HNSCC and other solid tumors, PI3K/mTOR inhibitors have had limited clinical success. Compared with PIK3CA$^{WT}$ HNSCC, PIK3CA$^{MUT}$ HNSCC cell lines and PDX models are more sensitive to PI3K/mTOR pathway inhibitors (Lui et al., 2013; Mazumdar et al., 2014; Keysar et al., 2013; Li et al., 2014; Elkabets et al., 2015; Zumsteg et al., 2016). However, PI3K/mTOR inhibition does not cause significant apoptosis in PIK3CA$^{MUT}$ HNSCC cell lines (Mazumdar et al., 2014). These published findings are consistent with those of the present study and with clinical findings demonstrating that PIK3CA$^{MUT}$ tumors tend to be more sensitive than PIK3CA$^{WT}$ tumors to PI3K/mTOR pathway inhibitors but still have modest clinical responses (Lui et al., 2013; Janku et al., 2012; Jimeno et al., 2015; Cal et al., 2017). Because HNSCC tumors with NOTCH1 mutations undergo cell death (rather than simple growth arrest) in response to PI3K/mTOR inhibitors, it was hypothesized that drugs targeting the PI3K/mTOR pathway have greater clinical efficacy in this genomic subtype that in PIK3CA$^{MUT}$ or NOTCH1$^{WT}$ HNSCC.

Resistance to PI3K/mTOR pathway inhibitors manifests as a lack of sustained pathway inhibition despite the use of potent agents. For example, mTORC1 inhibition blocks S6 kinase-dependent inhibition of insulin receptor substrate 1, leading to insulin-like growth factor 1 receptor and then PI3K/AKT activation (Wang et al., 2017). A second feedback loop occurs because AKT activation inhibits the nuclear localization of forkhead box class O, a transcriptional driver of receptor tyrosine kinase (RTK) expression. AKT inhibition relieves this feedback suppression, leading to RTK expression and subsequent extracellular signal-regulated kinase (ERK) activation (Chandarlapaty et al., 2011). Similarly, in HNSCC, the addition of mitogen-activated protein kinase kinase (MEK)/ERK or RTK pathway inhibition enhances anti-tumor effects of PI3K/mTOR inhibition (Mazumdar et al., 2014; Wang et al., 2014; Yamaguchi et al., 2016; Mohan et al., 2015). However, no differential effects on p-ERK after PI3K/mTOR inhibition based on NOTCH1 status were found. A third mechanism is the sustained PDK1 signaling that mediates residual mTORC1 activity despite potent PI3Kα inhibition in PI3Kα inhibitor-resistant PIK3CA$^{MUT}$ breast cancers (Castel et al., 2016). These findings suggest that sustained PDK1 activity is a mechanism of resistance to PI3K/mTOR inhibition in NOTCH1$^{WT}$ HNSCC. Additionally, other factors may influence response of HNSCC to PI3K/mTOR pathway inhibitors such as TP53 and TGFβ (Herzog et al., 2013).

This is the first study to establish a therapeutic vulnerability of NOTCH1$^{MUT}$ HNSCC to any class of drugs. Because NOTCH1 LOF mutations are common in other squamous cell carcinomas, including lung (8%) and esophageal (21%) carcinomas (Zhang et al., 2016), these findings have wide-ranging implications. The finding that NOTCH1 LOF mutations predict response to PI3K inhibitors may lead to the first biomarker-driven targeted therapy for HNSCC. In addition, targeting PDK1 may sensitize NOTCH1$^{WT}$ HNSCC to PI3K/mTOR pathway inhibitors.

Activating NOTCH1 mutations in T-ALL and ACC usually occur as missense or in-frame mutations to the heterodimerization domain that destabilize negative regulatory features leading to ligand-independent activation of the NOTCH1 pathway, or as truncating and nonsense mutations in the C-terminal part of the NOTCH1 protein (TAD and PEST) domains that interfere with intranuclear degradation of intracellular NOTCH1 and thus prolong signal activation (Agrawal et al., Chiang, et al., 2016). In cancer patient tumors, some common hotspot activating mutations in NOTCH1 do occur within the heterodimerization domain or PEST domain affecting the same amino acids in multiple cancer patients, which provides evidence they are activating. However, non-hotspot mutations also occur in cancers, including but not limited to T-ALL and ACC, where the functional impact of the amino acid changes cannot be so easily interpreted. The current invention uses an algorithm to make predictions about whether these additional NOTCH1 mutations occurring in amino acids outside known hot spots are likely to be activating, inactivating, or neutral with respect to NOTCH1 pathway function.

II. DEFINITIONS

Unless defined otherwise, all technical and scientific terms used herein have the same meanings as commonly understood by one of ordinary skill in the art to which this invention belongs.

A "biomarker" is anything that can be used as an indicator of a particular disease state or some other physiological state of an organism, such as a mammal or a human. A biomarker can be the presence or absence of a gene, measure of gene expression, presence or absence of a protein, measure of protein expression or functional effect of the protein activity that can be measured and correlated with a physiological state. Biomarkers are used in medicine as laboratory parameters that a physician can use to help make decisions in making a diagnosis and selecting a course of treatment. Moreover, biomarkers, as is typically and preferably the case for the biomarkers of the present invention, are used to help optimize ideal treatments and indicates the likelihood of benefiting from a specific therapy. The preferred biomarker of the present invention are described throughout the specification and appended claims.

The term "status of a biomarker", as used herein, should refer to a status of a biomarker that is correlated with vulnerability to the PI3K inhibitor in accordance with the present invention. Thus, by identifying the status of a biomarker and comparing it to the normal status of said biomarker, it can be determined whether a mammal or human patient's SCC is more likely to be vulnerable to the PI3K inhibitor therapy of the present invention, and, thus, whether the mammal or human patient is a good responder or responder that will benefit from said therapy, or, to the contrary, a poor responder or non-responder that will not benefit or will have little benefit from said therapy.

Thus, the term "normal status" of a biomarker can denote a normal status of such biomarker, which corresponds to the status of the biomarker which, typically and preferably, correspond to the status of such biomarker in a healthy mammal or human patient, specifically such as the wild-type DNA NOTCH1 sequence, or can denote a normal status and level, respectively, cleaved NOTCH1 protein (NICD1). Thus, by comparing the status of a biomarker of a mammal or human patient's tumor material or sample with its normal status, it can be determined, whether a mammal or human patient's tumor material or sample and thus a mammal or human patient is likely to benefit from said PI3K inhibitor therapy in accordance with the present invention. The "normal status" can, thus, refer to the sequence, parameter or level, typically and preferably, measured for comparison in a non-cancerous, healthy, wild-type tissue or cell, or in particular embodiment, placebo treated tumor cell.

The term "tumor" as used herein, should not be limited to a said primary tumor but typically and preferably include any tumor cell or group of cells that has moved away from the primary tumor. In the metastatic setting, the "tumor" of a said mammal or human patient may be localized in numerous different sites of the mammal's or human patient's body. Unless stated otherwise, when used in the form of "the tumor of a patient", the term refers to all tumor cells in the said mammal or human patient's body.

The term "squamous cell carcinoma" abbreviated as "SCC", as used herein, should typically and preferably include any SCC cell or group of cells that has moved away from the primary SCC site. In the metastatic setting, the "SCC" of a said mammal or human patient may be localized in numerous different sites of the mammal's or human patient's body. Unless stated otherwise, when used in the form of "the SCC of a patient", the term refers to all SCC cells in the said mammal or human patient's body.

The term "head and neck squamous cell carcinoma" abbreviated as "HNSCC", as used herein, should typically and preferably include any HNSCC cell or group of cells that forms a primary tumor, has recurred at the primary HNSCC site, or has moved away from the primary HNSCC site. In the metastatic setting, the "HNSCC" of a said mammal or human patient may be localized in numerous different sites of the mammal's or human patient's body. Unless stated otherwise, when used in the form of "the HNSCC of a patient", the term refers to all HNSC cells in the said mammal or human patient's body.

The term "recurrent head and neck squamous cell carcinoma", as used herein, refers to a head and neck squamous cell carcinoma (HNSCC), which had disappeared in response to a previous treatment but subsequently recurred.

The term "metastatic head and neck squamous cell carcinoma", as used herein, refers to a head and neck squamous cell carcinoma (HNSCC), which has spread to other sites within the body, forming so-called metastases.

The term "tumor material", as used herein, should refer to any material, such as, typically and preferably, any group of cells, any cell, or any sub-cellular component, DNA, mRNA, protein or product secreted therefrom, that originates from a said tumor, said SCC, and/or said HNSCC as defined herein, regardless of the method by which it was collected. The methods of collection of said tumor material are known to the skilled person in the art.

The term "sequenced DNA" as used herein, should refer to DNA obtained by sequencing methods known to the skilled person such as next generation sequencing but further should include cell-free circulating tumor DNA (ctDNA). "Next generation sequencing" methods are a group of high-throughput sequencing methods that parallelize the sequencing process, producing thousands or millions of sequences at once. The combination of the increase in data generated, coupled with lowered costs required to generate these data, has made this technology be recognized by those of skill in the art as a tractable, general purpose tool. Although a primary tumor itself or metastases derived from a primary tumor are currently the main source of tumor material including tumor DNA, acquiring tumor DNA through a biopsy is invasive, risky and often not possible. Dying tumor cells release small pieces of their DNA via different mechanisms into the bloodstream. These pieces are called cell-free circulating tumor DNA (ctDNA). In other words, ctDNA is tumor-derived fragmented DNA in the bloodstream that is not associated with cells. Because ctDNA may reflect the tumor genome in a more comprehensive manner, it has gained traction for its potential clinical utility. ctDNA can be isolated from different body fluids of a person, commonly referred to liquid biopsies. At present, plasma (derived from blood) is most commonly used as a source for ctDNA, but other body fluids including but not limited to saliva, urine and cerebrospinal fluid may also contain ctDNA.

The term "vulnerability of a squamous cell carcinoma (SCC)" as used herein, should in particular refer to the prediction that selected mammals or human SCC patients are predicted to likely benefit from therapeutic administration of the PI3K inhibitor because the SCC is sensitive and susceptible to the PI3K inhibitor therapy, including but not limited due to increased growth arrest and/or increased apoptosis believed to be caused by the loss of function in accordance with the present invention of the NOTCH1 protein. A "loss of function" (LoF) mutation, as used herein, is a mutation in the DNA of a gene, the result of which is that the gene product (such as the encoded protein) has less than normal or no function in a cell or organism (including a human cell or human being).

The term "treating" as used herein, unless otherwise indicated, means reversing, alleviating, inhibiting the progress of the growth of tumors, tumor metastases, or other cancer-causing or neoplastic cells in a mammal or a human patient. The term "treatment" as used herein, unless otherwise indicated, refers to the act of treating.

The phrase "a method of treating" or its equivalent, when applied to cancer treatment, refers to a procedure or course of action that is designed to reduce or eliminate the number of cancer cells or to alleviate the symptoms of a cancer. "A method of treating" cancer or another proliferative disorder does not necessarily mean that the cancer cells or other disordered cells will actually be eliminated, that the number of cells or disorder will actually be reduced, or that the symptoms of a cancer or other disorder will actually be alleviated. Often, a method of treating cancer will be performed even with a low likelihood of success, but which, given the medical history and estimated survival expectancy, is nevertheless deemed an overall beneficial course of action.

A "therapeutically effective amount" or "effective amount" is the amount of a PI3K inhibitor in accordance with the present invention that will elicit the biological or medical response of a tumor material, mammal or human patient that is being sought by the researcher, veterinarian, medical doctor or other clinician. The term "therapeutic administration", as used herein, should refer to the administration of therapeutically effective amount.

A "pharmaceutical composition" is a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives, for example; proteins, peptides, amino acids, lipids, and carbohydrates (e.g., sugars, including monosaccharides and oligosaccharides; derivatized sugars such as alditols, aldonic acids, esterified sugars and the like; and polysaccharides or sugar polymers), which can be present singly or in combination, comprising alone or in combination 1-99.99% by weight or volume. Carbohydrate excipients include, for example; monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, sorbitol (glucitol) and myoinositol. It can be solid or in a liquid form.

The term "NOTCH1 loss-of-function (LoF) mutation", as used herein, refers to any genetic mutation in the NOTCH1 gene in accordance with the present invention which are considered to result in loss of function of the NOTCH1 protein.

The term "an amount incompatible with NOTCH1 loss-of-function" as used herein, in particular in relation to the presence of NICD (e.g., NICD1), refers to an amount of NICD (e.g., NICD1) that is normally physiologically translocated into the nucleus following activation of NOTCH1 at the plasma membrane.

The terms "cleaved NOTCH1 intracellular domain protein", "cleaved NOTCH1 protein", "cl-NOTCH1 protein", "cl-NOTCH1" and "NICD1", are interchangeably used herein.

A "substitution" is a mutation that exchanges one base for another (i.e., a change in a single "chemical letter" such as switching an A to a G). Such a substitution could (i) change a codon to one that encodes a different amino acid and cause a small change in the protein produced; (ii) change a codon to one that encodes the same amino acid and causes no change in the protein produced ("silent mutations"); or (iii) change an amino-acid-coding codon to a single "stop" codon and cause an incomplete protein (an incomplete protein is usually nonfunctional). An "insertion" is a mutation in which one or multiple extra base pairs are inserted into a place in the DNA. A "deletion" is a mutation in which a one or multiple base pairs or a section of DNA is lost, or deleted.

A "splice site mutation" is a genetic mutation that inserts or deletes a number of nucleotides in the specific site at which splicing of an intron takes place during the processing of precursor messenger RNA into mature messenger RNA. The abolishment of the splicing site results in one or more introns remaining in mature mRNA and may lead to the production of aberrant proteins.

An "in-frame mutation" or a "frameshift mutation", which terms are interchangeably used herein, is a mutation caused by insertions or deletions of a number of nucleotides that is not evenly divisible by three from a DNA sequence. Due to the triplet nature of gene expression by codons, the insertion or deletion can change the reading frame (the grouping of the codons), resulting in a completely different translation from the original. This often generates truncated proteins that result in loss of function.

A "missense mutation" is a point mutation where a single nucleotide is changed to cause substitution of a different amino acid. Missense mutation is a type of nonsynonymous substitution in a DNA sequence. Missense mutations can render the resulting protein nonfunctional, however, not all missense mutations lead to appreciable protein changes. An amino acid may be replaced by an amino acid of very similar chemical properties, in which case, the protein may still function normally; this is termed a neutral, "quiet", "silent", or "conservative mutation". A "nonsense mutation", in turn, is another type of nonsynonymous substitution in which a codon is changed to a premature stop codon that results in truncation of the resulting protein.

The term "a missense or an in-frame mutation incompatible with NOTCH1 loss-of-function" as used herein should refer to a missense or an in-frame mutation which mutation either does not cause truncation or which mutation would still lead to a functional protein, and thus said later mutation would be, for example, a silent or conservative missense mutation. The missense or an in-frame mutation incompatible with NOTCH1 loss-of-function may be a missense or an in-frame mutation (i) not causing truncation of the resulting protein, preferably of a protein corresponding to human NOTCH1 protein of SEQ ID NO:2, or (ii) leading to a functional protein, preferably to a functional protein corresponding to human NOTCH1 protein of SEQ ID NO:2. The missense or an in-frame mutation incompatible with NOTCH1 loss-of-function may be a missense or an in-frame mutation not causing truncation of the resulting protein, preferably of a protein corresponding to human NOTCH1 protein of SEQ ID NO:2.

III. NOTCH1 Loss-of-Function Mutations

In accordance with the present invention, SCCs considered to harbor a LoF mutation in the NOTCH1 gene are more likely to respond to (i.e., to shrink due to believed increased apoptosis) a PI3K inhibitor. Detection of one or more of said LoF mutations in the NOTCH1 gene predicts that the patient will benefit from treatment with the PI3K inhibitor. On the other hand, detection of wild-type NOTCH1 predicts that the patient will benefit from treatment with a combination of a PDK1 inhibitor and another PI3K/mTOR pathway inhibitor.

In an embodiment of the present invention, said identifying the status of a biomarker from tumor material from a mammal, preferably from a human patient, comprise providing the status of said biomarker of said tumor material such as, typically and preferably, the sequenced tumor DNA, preferably sequenced human tumor DNA, and/or the protein level of NICD (E.G., NICD1), typically and preferably by using appropriate assays. Typically and preferably, the status of said biomarker is provided by generating said sequenced tumor DNA by a sequencing assay, typically and preferably by a commercially available sequencing assay, and detecting said one or more mutations in the NOTCH1 gene from the dataset generated by said sequencing assay. Thus, typically and preferably, the methods of the present invention may include but need not to include the steps such as the generating of said sequenced tumor DNA; the provision of the status of said biomarker of said tumor material which allows the identification of one or more mutations in the NOTCH1 gene and/or the protein level of NICD (E.G., NICD1) in accordance with the present invention is sufficient.

In a preferred embodiment of the present invention, said SCC is selected from the group consisting of head and neck squamous cell carcinoma (HNSCC), skin squamous cell carcinoma, esophagus squamous cell carcinoma, and lung squamous cell carcinoma. In another very preferred embodiment of the present invention, said SCC is head and neck squamous cell carcinoma (HNSCC). In a further preferred embodiment of the present invention, said SCC is recurrent or metastatic HNSCC. In a further preferred embodiment of the present invention, said SCC is recurrent HNSCC. In a further preferred embodiment of the present invention, said SCC is metastatic HNSCC. In a further preferred embodiment of the present invention, said SCC is recurrent and metastatic HNSCC.

In a preferred embodiment of the present invention, said biomarker is sequenced tumor DNA, preferably human tumor DNA, to identify one or more mutations in the NOTCH1 gene, preferably in the human NOTCH1 gene of SEQ ID NO:1, encoding the NOTCH1 protein, preferably the human NOTCH1 protein of SEQ ID NO:2. In a very preferred embodiment of the present invention, said mammal is a human patient, and said biomarker is sequenced human tumor DNA to identify one or more mutations in the human NOTCH1 gene of SEQ ID NO:1, encoding the human NOTCH1 protein of SEQ ID NO:2.

In an embodiment of the present invention, in particular for the method of predicting the vulnerability of a tumor material from a squamous cell carcinoma (SCC) of a mammal, preferably of a human patient, to a PI3K inhibitor, said identifying the status of a biomarker of said tumor material comprise contacting a tumor material from a squamous cell carcinoma (SCC) with said PI3K inhibitor, and/or further providing the status of said biomarker of said tumor material such as the sequenced tumor DNA, preferably sequenced human tumor DNA, and/or the protein level of NICD (E.G., NICD1), typically and preferably, by using appropriate assays such as by generating said sequenced tumor DNA by a sequencing assay, typically and preferably by a commercially available sequencing assay, and detecting said one or more mutations in the NOTCH1 gene from the dataset generated by said sequencing assay. Thus, typically and preferably, the methods of the present invention, in particular the method of predicting the vulnerability of a tumor material from a squamous cell carcinoma (SCC) of a mammal, preferably of a human patient, to a PI3K inhibitor, may include but need not to include the contacting step and/or the generating of said sequenced tumor DNA; the provision of the status of said biomarker of said tumor material which allows the identification of one or more mutations in the NOTCH1 gene and/or the protein level of NICD (E.G., NICD1) in accordance with the present invention is sufficient.

In a preferred embodiment of the present invention, said NICD (E.G., NICD1) is determined by immunohistochemistry (IHC). In a further preferred embodiment of the present invention, said assay to measure said protein level of NICD (E.G., NICD1) is by immunohistochemistry (IHC), and wherein preferably said IHC assay is effected as described in the examples.

In a preferred embodiment of the present invention, said mammal is a mammal selected from the group consisting of a cat, a dog, a horse or a human, preferably a cat, a dog, or a human. In a further very preferred embodiment of the present invention, said mammal is a human patient.

In a further very preferred embodiment of the present invention, said mammal is a human patient, wherein for this very preferred embodiment of the present invention, the inventive methods thus refer, typically and preferably to the respective human genes and proteins.

In a first aspect, the present invention provides a method of predicting the vulnerability of a squamous cell carcinoma (SCC) to inhibition by a PI3K inhibitor, wherein said method comprises
  (a) identifying the status of a biomarker from tumor material from a mammal, preferably from a human patient, wherein the biomarker is selected from the group consisting of
    (i) sequenced tumor DNA, preferably human tumor DNA, to identify one or more mutations in the NOTCH1 gene, preferably in the human NOTCH1 gene of SEQ ID NO:1, encoding the NOTCH1 protein, preferably the human NOTCH1 protein of SEQ ID NO:2;
    (ii) protein level of cleaved NOTCH1 intracellular domain, preferably the protein level of human cleaved NOTCH1 intracellular domain (NICD1; SEQ ID NO:3); and
    (iii) a combination of biomarker (i) and (ii);
  (b) comparing the status of the biomarker in said tumor material to a normal status of the biomarker; and
  (c) selecting the mammal, preferably the human patient, as being predicted to benefit from therapeutic administration of the PI3K inhibitor, if
    (i) said mammal's, preferably human patient's, SCC harbors one or more NOTCH1 mutations, wherein said NOTCH1 mutation is not
      a. a mutation in the TAD domain or in the PEST domain of said NOTCH1 gene, and wherein preferably said NOTCH1 mutation is not a mutation in the TAD domain or in the PEST domain of said human NOTCH1 gene corresponding to aa 2159-2555 of SEQ ID NO:2;
      b. a missense or an in-frame mutation, preferably a missense or an in-frame mutation incompatible with NOTCH1 loss-of-function, in the Lin-12/

Notch 1 Repeats (LNR) or in the heterodimerization domain (HD domain) of said NOTCH1 gene, and wherein preferably said NOTCH1 mutation is not a missense or not an in-frame mutation, further preferably not a missense or an in-frame mutation incompatible with NOTCH1 loss-of-function, in the Lin-12/Notch 1 Repeats (LNR) or in the heterodimerization domain (HD domain) of said human NOTCH1 gene corresponding to aa 1442-1734 of SEQ ID NO:2; and/or c. a mutation in the splice donor boundary (Exon 33), or in the acceptor boundary (Exon 34) of said NOTCH1 gene, and wherein preferably said NOTCH1 mutation is not a mutation in the splice donor boundary (Exon 33), or in the acceptor boundary (Exon 34) of said human NOTCH1 gene corresponding to nt 5639-6082 of SEQ ID NO:1; and/or (ii) said mammal's, preferably human patient's, SCC comprises cleaved NOTCH1 intracellular domain protein, preferably human cleaved NOTCH1 intracellular domain (NICD1; SEQ ID NO:3) in an amount incompatible with NOTCH1 loss-of-function; and/or (iii) a combination of (i) and (ii).

The Cancer Genome Atlas (TCGA) describes nearly 100 NOTCH1 mutations identified for T-ALL and HNSCC with the pattern, site of occurrence and nature of said NOTCH1 mutations (Cancer Genome Atlas 2015; Nowell & Radtke 2017). The comparison of the pattern of said NOTCH1 mutations led to the conclusion that the oncogenic NOTCH1 mutations found in T-ALL occur in a hotspot of mostly missense mutations within the negative regulatory HD domain or in a second hotspot of mostly truncating mutations near the C-terminus, deleting the PEST domain and causing increased stabilization of activated NOTCH1 in the nucleus (Ferrando 2009; Nowell & Radtke 2017). However, in HNSCC the truncating mutations are scattered throughout the protein but not in the PEST domain, and the missense mutations cluster in the extracellular EGF-ligand binding domains. Unlike T-ALL, only 1% of NOTCH1 missense mutations in HNSCC are in either the negative regulatory or PEST domains. Without being bound, it is believed that mutations in the splice donor boundary (Exon 33), or in the acceptor boundary (Exon 34) of said NOTCH1 gene are able to truncate said NOTCH1 gene, in particular, said human NOTCH1 gene of SEQ ID NO:1, within said TAD domain or said PEST domain.

Thus, essentially any mutations in the TAD or PEST domains, any missense or in-frame mutations in the LNR and HD domains, and splice donor (Exon 33) or acceptor (Exon 34) boundaries which would hypothetically truncate the protein within the TAD/PEST domains will be excluded as considered to benefit from the treatment in accordance with the present invention. All other NOTCH1 mutations will be eligible. Thus, for said very preferred embodiments, human patients with NOTCH1 mutations in regions associated with activation including TAD/PEST domains or mutations in LNR and HD domains that are not truncating would be excluded. Splice mutations in Exon 33 or 34 would also be excluded, but patients with NOTCH1 mutation in all other regions would be eligible to benefit from the treatment in accordance with the present invention.

IV. PI3K/mTOR PATHWAY INHIBITORS

Phosphoinositide 3-kinase (PI3K) pathway inhibitors, including dual PI3K/mammalian target of rapamycin (mTOR) inhibitors are known for the skilled person in the art and have been described extensively (Janku et al., Nat. Rev. Clin. Oncol., 15:278-291, 2018; Thorpe et al., PI3K in cancer: divergent roles of isoforms, modes of activation and therapeutic targeting. (2015) Nat. Rev. Cancer 15, 7-24; WO2010/052569; WO2016/075130, the entire disclosure of each of which is incorporated herein by way of reference). PI3K inhibitors, usable for the present invention, are disclosed in Table 2 of Janku et al. (2018) and are selected from the group of BKM120, CNIO-PI3Ki, GCD0032, GDC0941, GNE317, PI103, PIK75, BAY806946 (copanlisib), ZSTK474, PX866, XL147, CH5132799, GDC0980, PF04691502, BGT226, BEZ235, XL765, GSK1059615, GSK2126458 (omipalisib), DS7423, PKI402, MK2206, PWT33597, SF1126, PF05212384, BAY806942, BYL719, XL147, and bimiralisib (also known as PQR309, PQR-309; identified by CAS No.: 1225037-39-7).

In a further preferred embodiment of the present invention, said PI3K inhibitor is selected from the group consisting of 5-(4,6-dimorpholino-1,3,5-triazin-2-yl)-4-(trifluoromethyl)pyridin-2-amine;

5-(4,6-dimorpholino-1,3,5-triazin-2-yl)-4-(trifluoromethyl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;

(S)-4-(difluoromethyl)-5-(4-(3-methylmorpholino)-6-morpholino-1,3,5-triazin-2-yl)pyrimidin-2-amine;

(R)-4-(difluoromethyl)-5-(4-(3-methylmorpholino)-6-morpholino-1,3,5-triazin-2-yl)pyridin-2-amine;

(R)-4-(difluoromethyl)-5-(4-(3-methylmorpholino)-6-morpholino-1,3,5-triazin-2-yl)pyrimidin-2-amine;

4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

4-(difluoromethyl)-5-(4-morpholino-6-(piperazin-1-yl)-1,3,5-triazin-2-yl)pyrimidin-2-amine; and 4-(difluoromethyl)-5-(4,6-dimorpholino-1,3,5-triazin-2-yl)pyridin-2-amine.

In a further preferred embodiment of the present invention, said PI3K inhibitor is selected from any of the following formula

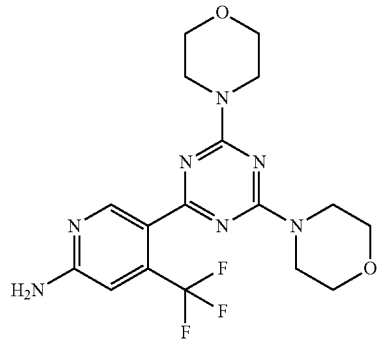

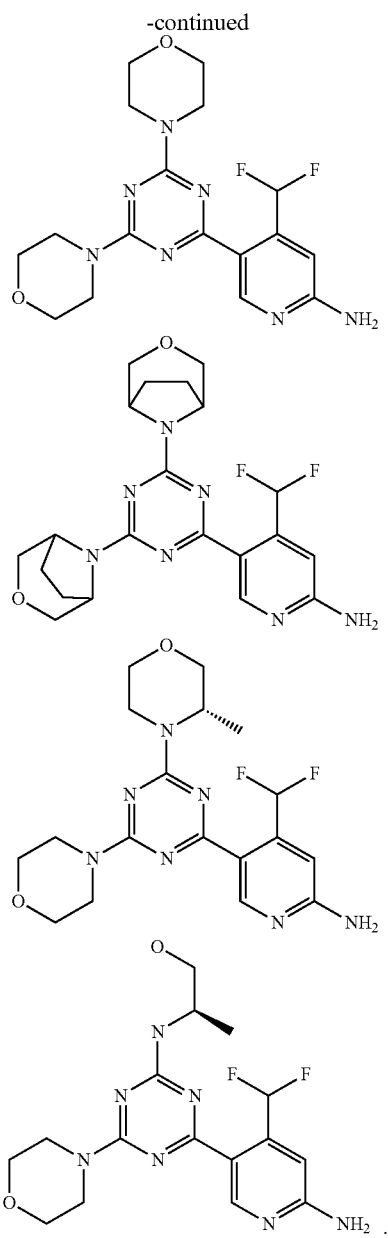

In some embodiments, a PI3K/mTOR pathway inhibitor may be an AKT inhibitor. In additional embodiments, the AKT inhibitor is selected from the group consisting of (2s)-1-(1h-Indol-3-yl)-3-{[5-(3-Methyl-1h-Indazol-5-Yl) pyridin-3-Yl]oxy}propan-2-Amine or 5-{5-[(2S)-2-amino-3-(1H-indol-3-yl)propoxy]pyridin-3-yl}-3-methyl-1H-indazole (also called A-443654); ALM301 described in U.S. Pat. No. 9,221,838, which is herein incorporated by reference in its entirety; 3-(3-(4-(1-aminocyclobutyl)phenyl)-5-phenyl-3H-imidazo[4,5-b]pyridin-2-yl)pyridin-2-amine; COTI2 described in U.S. Pat. No. 8,034,815, which is herein incorporated by reference in its entirety. Suitable AKT inhibitors are also described, for example, in Nitulescu (2016) International Journal of Oncology 48, 869-885, the disclosure of which is incorporated by reference herein. In additional embodiments, the AKT inhibitors may include ATP-competitive inhibitors, such as isoquinoline-5-sulfonamides, including H-8, H-89 and NL-71-101; aminofurazans, including GSK690693; heterocyclic rings, including CCT128930, ipatasertib, A-674563, and A-443654; phenylpyrazole derivatives, including AT7867 and AT13148; thiophenecarbozamide derivatives, including afuresertib (GSK2110183); 2-pyrimidyl-5-amidothiophene derivatives, including DC120, uprosertib (GSK2141795); allosteric inhibitors, such as 2,3-diphenylquinoxaline analogues, including 2-[4-(2-aminoprop-2-yl)phenyl]-3-phenylquinoxaline and triazolo[3,4-f][1,6]naphthyridin 3(2H) one derivative (MK-2206); alkylphospholipids, including edelfosine, ilmofosine (1-Hexadecylmercapto-2-methoxymethyl-3-propyl phosphoric acid monocholine ester; BM 41.440), miltefosine (hexadecylphosphocholine, HePC), perifo sine (Octadecyl-(1,1-dimethyl-4-piperidylio) phosphate; D 21266), erucylphosphocholine (ErPC), erufosine (ErPC3), and erucylphosphohomocholine; indole-3-carbinol analogues, including Indole 3 carbinol, 3 chloroacetylindole, diindolylmethane, diethyl 6-methoxy-5,7-dihydroindolo[2,3-b]carbazole-2,10-dicarboxylate (SR13668), and (OSU-A9); sulfonamide and thiourea derivatives, including PH-316, PHT-427, PIT-1, and DM-PIT-1; purine derivatives, including triciribine, API-1,3-phenyl-3H-imidazo[4,5-b]pyridine derivative; triciribine mono phosphate active analogue (tricyclic nucleotide triciribine phosphate or triciribine phosphate monohydrate (TCN-P), 4-Amino-5,8-dihydro-5-oxo-8-β-D-ribofuranosyl-pyrido[2,3-d]pyrimidine-6-carboxamide) or other structures and derivatives (e.g. 3 methyl xanthine, quinoline-4-carboxamide and 2-[4-(cyclohexa 1,3-dien 1-yl)-1H-pyrazol-3-yl]phenol, 3 oxo tirucallic acid, 3α-acetoxy tirucallic and 3β acetoxy tirucallic acids, and acetoxy tirucallic acid); or irreversible inhibitors including luctoquinomycin or Boc-Phe-vinyl ketone.

Several PI3K/mTOR inhibitors are known and have been described (Courtney et al., 2010; Maira, 2011; Rodon et al., 2013; Fruman & Rommel, 2014; Beaufils et al., 2017; Bohnacker et al., 2017; Fruman et al., 2017). Among them bimiralisib is a pan-class I PI3K/mTOR antagonist that potently inhibits PI3Kα and mTOR (IC50=2 to 25 nM), with less potency against PI3Kβ (IC50=820 nM) (Beaufils et al., 2017, Bohnacker et al., 2017). It is highly selective and does not significantly inhibit other protein kinases tested in biochemical assays (KINOMEscan), or receptors or ion channels in the CEREP Bioprint profile (Beaufils et al., 2017, Bohnacker et al., 2017). Bimiralisib is administered orally and crosses the blood-brain barrier (Beaufils et al., 2017, Bohnacker et al., 2017). Human pharmacokinetic data demonstrate rapid drug absorption (Tmax<2 h), terminal half-life of 51 hours, and Cmax of 0.96 to 1.46 μg/mL (2.3 to 3.5 μM) (Wicki et al., 2018). Pharmacodynamic data demonstrate marked decreases of pAKT, pS6 and p4EBP in tumor tissue at therapeutic doses (Beaufils et al., 2017, Bohnacker et al., 2017, Wicki et al., 2018).

V. PDK1 INHIBITORS

3-Phosphoinositide-dependent protein kinase 1 (PDK1) is a serine/threonine protein kinase that can phosphorylate a number of protein kinases, including protein kinase B (Akt), and is an important component of the PI3K-PDK1-Akt pathway. Many inhibitors of PDK1 have been identified and are being developed for the treatment of cancer (e.g. BX-424 (Berlex Biosciences); OSU-03012; OSU-03013 (also called NSC-728209 and NSC-728210); GSK2334470; BX-912; BX-795; BAG 956; PHT-427).

In some embodiments, the PDK1 inhibitor is selected from the group consisting of 4-[3-chloro-4-[[(2R)-3,3,3-trifluoro-2-hydroxy-2-methylpropanoyl]amino]phenyl]

sulfonyl-N,N-dimethylbenzamide (also called AZD7545); sodium dichloroacetate (also called CERESINE); 6,8-bis (benzylsulfanyl)octanoic acid (also called CPI613); lipoic acid or 6,8-bis[(phenylmethyl)thio]-octanoic acid (also called JTT251); and 4-amino-N-[(1 S)-1-(4-chlorophenyl)-3-hydroxypropyl]-1-(7H-pyrrolo[2,3-d]pyrimidin-4-yl)piperidine-4-carboxamide (AZD5363). For example, U.S. Pat. No. 6,727,284 describes the ceresine inhibitors and is herein incorporated by reference in its entirety. U.S. Pat. No. 8,263,653 describes the CPI613 inhibitors and is herein incorporated by reference in its entirety.

Additional PDK1 inhibitors are described by Medina, J Med Chem. 2013 Apr. 11; 56(7):2726-37; Nagashima et al., J Biol Chem. 2011 Feb. 25; 286(8):6433-48; U.S. Publication No. 2010/0144730; Rettenmaier et al., 2014, Proc. Natl. Acad. Sci. U.S.A. 111(52):18590-18595; Rettenmaier et al., 2015, J. Med. Chem. 58(20):8285-8291; Hossen et al., 2015, Expert Op. Ther. Pat. 25(5):513-537; International Publication No. WO 2005/041953; International Publication No. WO 2006/106326; U.S. Pat. No. 7,105,563; International Publication No. WO 2008/005457; International Publication No. WO2005054238; International Publication No. WO 2006/015124; International Publication No. WO 2004/087707; International Publication No. WO 2003/064397; U.S. Publication No. 2007/0135429; E.P. Patent No. 1486488; International Publication No. WO 2011/076327; International Publication No. WO 2011/006567; International Publication No. WO 2010/017047; Erlanson et al., 2011, Biorg. Med. Chem. Lett. 21:3078-83; Nagashim et al., 2011, J. Biol. Chem. 286:6433-48; International Publication No. WO 2010/065384; International Publication No. WO 2010/127754; International Publication No. WO 2008/107444; International Publication No. WO 2010/007114; International Publication No. WO 2010/007116; International Publication No. WO 2010/019637; International Publication No. WO 2010/120854; International Publication No. WO 2009/153313; International Publication No. WO 2008/079988; International Publication No. WO 2011/044157; International Publication No. WO 2008/109599; International Publication No. WO 2008/109613; Nittoli et al., 2010, Eur. J. Med. Chem. 45:1379-86; U.S. Publication No. 2009/0111799; U.S. Publication No. 2012/0208819; U.S. Publication No. 2014/0017701; U.S. Publication No. 2011/0269958; U.S. Publication No. 2012/0245355; International Publication No. WO 2012/072200; International Publication No. WO 2012/036974; International Publication No. WO 2012/058174; U.S. Publication No. 2013/0165450; International Publication No. WO 2012/058176; International Publication No. WO 2011/137219; U.S. Publication No. 2013/0053382; U.S. Publication No. 2012/0277229; International Publication No. WO 2012/135799; and U.S. Publication No. 2012/0003668. (Each of which is incorporated by reference in its entirety herein).

VI. METHODS OF TREATMENT

The present invention provides methods of treating a patient having a squamous cell carcinoma with a PI3K/mTOR pathway inhibitor, either alone or in combination with a PDK1 inhibitor. In cases where the patient's SCC harbors a NOTCH1 loss-of-function mutation, the patient is treated with a PI3K inhibitor alone. In cases where the patient's SCC does not harbor a NOTCH1 loss-of-function mutation, the patient is treated with a combination of a PI3K/mTOR pathway inhibitor in addition to a PDK1 inhibitor. Such treatment may also be in combination with another therapeutic regime, such as chemotherapy or immunotherapy. Certain aspects of the present invention can be used to select a cancer patient for treatment based on the presence of a NOTCH1 loss-of-function mutation in the patient's cancer cells. In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may harbor an NOTCH1 loss-of-function mutation.

The present invention provides a method of method of treating a squamous cell carcinoma (SCC) of a mammal, preferably a human patient, comprising administering a therapeutically effective amount of a PI3K inhibitor to said mammal, preferably said human patient, wherein (i) said mammal's, preferably human patient's, SCC harbors one or more NOTCH1 mutations, wherein said NOTCH1 mutation is not
  a. a mutation in the TAD domain or in the PEST domain of said NOTCH1 gene, and wherein preferably said NOTCH1 mutation is not a mutation in the TAD domain or in the PEST domain of said human NOTCH1 gene corresponding to aa 2159-2555 of SEQ ID NO:2;
  b. a missense or an in-frame mutation, preferably a missense or an in-frame mutation incompatible with NOTCH1 loss-of-function, in the Lin-12/Notch 1 Repeats (LNR) or in the heterodimerization domain (HD domain) of said NOTCH1 gene, and wherein preferably said NOTCH1 mutation is not a missense or not an in-frame mutation, further preferably not a missense or an in-frame mutation incompatible with NOTCH1 loss-of-function, in the Lin-12/Notch 1 Repeats (LNR) or in the heterodimerization domain (HD domain) of said human NOTCH1 gene corresponding to aa 1442-1734 of SEQ ID NO:2; or
  c. a mutation in the splice donor boundary (Exon 33), or in the acceptor boundary (Exon 34) of said NOTCH1 gene, and wherein preferably said NOTCH1 mutation is not a mutation in the splice donor boundary (Exon 33), or in the acceptor boundary (Exon 34) of said human NOTCH1 gene corresponding to nt 5639-6082 of SEQ ID NO:1; or (ii) said mammal's, preferably human patient's, SCC comprises cleaved NOTCH1 intracellular domain protein, preferably human cleaved NOTCH1 intracellular domain (NICD1; SEQ ID NO:3) in an amount incompatible with NOTCH1 loss-of-function; or (iii) a combination of (i) and (ii).

In another aspect, the present invention provides a method of method of treating a squamous cell carcinoma (SCC) of a mammal, preferably a human patient with a PI3K inhibitor, wherein said method comprises (a) selecting said mammal, preferably said human patient, as being predicted to benefit from said treatment with said PI3K inhibitor, wherein said selecting comprises
  (i) identifying the status of a biomarker from tumor material from said mammal, preferably from said human patient, wherein the biomarker is selected from the group consisting of
    a. sequenced tumor DNA, preferably human tumor DNA, to identify one or more mutations in the NOTCH1 gene, preferably in the human NOTCH1 gene of SEQ ID NO:1, encoding the NOTCH1 protein, preferably the human NOTCH1 protein of SEQ ID NO:2;

b. protein level of cleaved NOTCH1 intracellular domain, preferably the protein level of human cleaved NOTCH1 intracellular domain (NICD1; SEQ ID NO:3); and
c. a combination of biomarker (i) and (ii);
(ii) comparing the status of the biomarker in said tumor material to a normal status of the biomarker; and
(iii) selecting the mammal, preferably the human patient, as being predicted to benefit from said treatment with said PI3K inhibitor, if
   a. said mammal's, preferably human patient's, SCC harbors one or more NOTCH1 mutations, wherein said NOTCH1 mutation is not
      i. a mutation in the TAD domain or in the PEST domain of said NOTCH1 gene, and wherein preferably said NOTCH1 mutation is not a mutation in the TAD domain or in the PEST domain of said human NOTCH1 gene corresponding to aa 2159-2555 of SEQ ID NO:2;
      ii. a missense or an in-frame mutation, preferably a missense or an in-frame mutation incompatible with NOTCH1 loss-of-function, in the Lin-12/Notch 1 Repeats (LNR) or in the heterodimerization domain (HD domain) of said NOTCH1 gene, and wherein preferably said NOTCH1 mutation is not a missense or not an in-frame mutation, further preferably not a missense or an in-frame mutation incompatible with NOTCH1 loss-of-function, in the Lin-12/Notch 1 Repeats (LNR) or in the heterodimerization domain (HD domain) of said human NOTCH1 gene corresponding to aa 1442-1734 of SEQ ID NO:2 (full length human NOTCH1 protein]
      iii. a mutation in the splice donor boundary (Exon 33), or in the acceptor boundary (Exon 34) of said NOTCH1 gene, and wherein preferably said NOTCH1 mutation is not a mutation in the splice donor boundary (Exon 33), or in the acceptor boundary (Exon 34) of said human NOTCH1 gene corresponding to nt 5639-6082 of SEQ ID NO:1; or
   b. said mammal's, preferably human patient's, SCC comprises cleaved NOTCH1 intracellular domain protein, preferably human cleaved NOTCH1 intracellular domain (NICD1; SEQ ID NO:3) in an amount incompatible with NOTCH1 loss-of-function; or
   c. a combination of a. and b.;
(b) administering a therapeutically effective amount of said PI3K inhibitor to said selected mammal, preferably said selected human patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

In a preferred embodiment of the present invention, said administration is an oral administration, parenteral administration, intravenous administration, or a topical administration. In a further preferred embodiment of the present invention, said administration is an oral administration.

In a further very preferred embodiment of the present invention, said PI3K inhibitor is formulated for oral administration, wherein preferably said PI3K inhibitor is in the form of a tablet, a pill or a capsule, most preferably in the form of a capsule.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below, either (a) a PI3K/mTOR pathway inhibitor is "A" and another anti-cancer therapy is "B" or (b) a PI3K/mTOR pathway inhibitor in combination with a PDK1 inhibitor is "A" and another anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids, such as retinoic acid; capecitabine; carboplatin, procarbazine, plicomycin, gemcitabine, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as y-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p9'7), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739, 169; Hui and Hashimoto, Infection Immun., 66(11):5329-5336, 1998; Christodoulides et al., Microbiology, 144(Pt 11):3027-3037, 1998); cytokine therapy, e.g., interferons α, β, and γ, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, Nat Rev Cancer, 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human- ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immunoglobulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675,206, also known as tremelimumab; formerly ticilimumab); U.S. Pat. No. 6,207,156; Hurwitz et al. (1998) *Proc Natl Acad Sci USA,* 95(17): 10067-10071; Camacho et al. (2004) *J Clin Oncology,* 22(145): Abstract No. 2505 (antibody CP-675206); and Mokyr et al. (1998) *Cancer Res,* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP_002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STATS and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

VII. KITS

In various aspects of the invention, a kit is envisioned containing, diagnostic agents, therapeutic agents and/or delivery agents. In some embodiments, the present invention contemplates a kit for detecting a NOTCH1 loss-of-function in a patient's tumor cells. In some embodiments, the present invention contemplates a kit for preparing and/or administering a therapy of the invention. The kit may comprise reagents capable of use in administering an active or effective agent(s) of the invention. Reagents of the kit may include one or more anti-cancer components of a combination therapy, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass. The kit may further include an instruction sheet that outlines the procedural steps of the methods, and will follow substantially the same procedures as described herein or are known to those of ordinary skill.

As such, the present invention provides a kit for selecting a mammal, preferably a human patient, with squamous cell carcinoma being predicted to benefit or not to benefit from administration of a PI3K inhibitor, the kit comprising:
(a) a means for identifying in a tumor material a status of a biomarker selected from the group consisting of
 (i) sequenced tumor DNA, preferably human tumor DNA, to identify one or more mutations in the NOTCH1 gene, preferably in the human NOTCH1 gene of SEQ ID NO:1, encoding the NOTCH1 protein, preferably the human NOTCH1 protein of SEQ ID NO:2;
 (ii) protein level of cleaved NOTCH1 intracellular domain (cl-NOTCH1, [NICD1]; SEQ ID NO:3), wherein preferably said NICD1 is determined by immunohistochemistry (IHC); and
 (iii) a combination of biomarker (i) and (ii);
(b) a means for identifying the normal status.

In a preferred embodiment of the inventive kit, said means for identifying the normal status is information containing a predetermined normal status of the biomarker that has been correlated with vulnerability to the PI3K inhibitor.

In a further very preferred embodiment, said kit for selecting a mammal with squamous cell carcinoma being predicted to benefit or not to benefit from administration of a PI3K inhibitor is a kit for selecting a human patient with squamous cell carcinoma, preferably HNSCC, being predicted to benefit or not to benefit from administration of said PI3K inhibitor.

In a further preferred embodiment of the inventive kit, said biomarker is sequenced tumor DNA, preferably sequenced human tumor DNA, and wherein the means for identifying the normal status is the wild-type human NOTCH1 gene of SEQ ID NO:1.

In a further very preferred embodiment of the inventive kit, said kit is a kit for selecting a human patient with squamous cell carcinoma, preferably HNSCC, and said biomarker is sequenced human tumor DNA, and wherein the means for identifying the normal status is the wild-type human NOTCH1 gene of SEQ ID NO:1.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods for Examples 4-9

Cells and reagents. We obtained and subjected 50 human papilloma virus (HPV)-negative and 9 HPV-positive HNSCC cell lines to whole-exome sequencing, reverse-phase protein array analysis, and gene expression profiling as described previously (Kalu et al., 2017; Kalu et al., 2018; Zhang et al., 2017). All the cell lines were genotyped by short tandem repeat analysis, and all cell lines were mycoplasma-free at the time of testing with a mycoplasma detection kit (Lonza, Walkersville, MD). UMSCC49 parental and NOTCH1 knockout (KO) cells were purchased from Dr. Chad Brenner at the University of Michigan. An erythromycin ribosomal methylase (ERM) plasmid expressing PDK1-green fluorescent protein was a gift from Dr. Gordon Mills. Cells were transfected with the PDK1-expressing plasmid with Lipofectamine 3000 (Life Technologies, Grand Island, NY) for 6 hours and selected with 1-2 mg/ml G418 (Sigma, St. Louis, MO). To create the PJ34, FaDU, and MDA686LN NOTCH1 KO lines, we transfected the parental cell lines with a NOTCH1 CRISPR/Cas9 KO plasmid (sc-421930; Santa Cruz, Dallas, TX) using GenJet DNA transfection reagent (Signagen, Rockville, MD). The transfected cells were sorted based on green fluorescent protein expression, and individual clones were obtained. All other drugs were purchased from Selleck Chemicals (Houston, TX) and prepared as 10 mmol/L stock solutions in dimethyl sulfoxide (DMSO).

Cell viability assay. HNSCC cell lines were treated with DMSO (vehicle) or PI3K/mTOR pathway inhibitors at seven different concentrations (0.018-9.613 µM) for 72 hours. A CellTiter-Glo luminescent cell viability assay (Promega, Madison, WI) was performed as described previously (Castel et al., 2016; Muellner et al., 2011). Inhibitory concentration (ICs) and area under the curve (AUC) values were calculated using the drexplorer R package with a best-fit dose-response model (Zumsteg et al., 2016). The combination indices were calculated using the Chou-Talalay method (Cal et al., 2017) in CalcuSyn (Biosoft, Cambridge, UK). We tested the reproducibility and robustness of the data generated using three quality control parameters as described previously (Bohnacker et al., 2017). These parameters were the concordance correlation coefficient, location shift, and maximum standard deviation between two biological replicates for three technical and two biological replicates. Based on heuristics from our previous screening studies in lung cancer (Bohnacker et al., 2017), the cut-offs for reproducibility were a concordance correlation coefficient greater than 0.8, a location shift less than 0.9, and a standard deviation less than 0.23 based on the normal mixture fit model. Experiments not satisfying these criteria were repeated. The replicate with the smallest experimental variation measured by the median of standard deviation was chosen as a representative of the replicates, and its IC values served as the final values for subsequent analysis.

Western blot analysis. Western blot analysis was performed as described previously (Ferrarotto et al., 2016). In brief, cells were lysed with ice-cold lysis buffer, and the lysates were centrifuged at 20,000×g for 10 minutes at 4° C. Cell samples containing equal amounts of protein were resolved using sodium dodecyl sulfate-polyacrylamide gel electrophoresis, transferred to nitrocellulose membranes, and immunoblotted with different primary antibodies. Protein expression was detected using a horseradish peroxidase-conjugated secondary antibody (Bio-Rad, Hercules, CA) and electrochemiluminescence reagent (Amersham Biosciences, Pittsburg, PA). The antibodies are listed in Table 1.

tutes of Health, Bethesda, MD). Assays were performed in triplicate, and each test was completed twice on different days.

Mouse models. This study was performed in accordance with the Guide for the Care and Use of Laboratory Animals of the National Institutes of Health and approved by MD Anderson's Institutional Animal Care and Use Committee. Subcutaneous xenograft and orthotopic nude mouse tongue models were created as described previously (Myers et al., 2002). GSK2126458 was administered by oral gavage 5 days per week at 1 mg/kg (orthotopic model) or 3 mg/kg (subcutaneous xenograft model).

TUNEL tissue staining. Harvested tumor tissues were fixed in 10% formalin, embedded in paraffin, cut into 5-μm sections, and stored until further use. Deparaffinized and rehydrated tissue sections were processed for DNA labeling by terminal deoxynucleotidyl transferase, and then strepta-

TABLE 1

Antibodies used in Western blot analyses

| Antibody | Host species | Supplier | Dilution |
| --- | --- | --- | --- |
| p-AKT$^{S473}$ | Rabbit | Cell Signaling Technology | 1:1000 |
| p-AKT$^{T308}$ | Rabbit | Cell Signaling Technology | 1:1000 |
| AKT | Rabbit | Cell Signaling Technology | 1:1000 |
| P-S6$^{S242/244}$ | Rabbit | Cell Signaling Technology | 1:2000 |
| P-S6$^{S235/236}$ | Rabbit | Cell Signaling Technology | 1:2000 |
| S6 | Rabbit | Cell Signaling Technology | 1:1000 |
| p-4EBP1$^{T37/42}$ | Rabbit | Cell Signaling Technology | 1:2000 |
| 4EBP1 | Rabbit | Cell Signaling Technology | 1:1000 |
| NICD | Rabbit | Cell Signaling Technology | 1:1000 |
| NOTCH1 | Rabbit | Cell Signaling Technology | 1:1000 |
| PARP | Rabbit | Cell Signaling Technology | 1:1000 |
| Caspase 3 | Rabbit | Cell Signaling Technology | 1:1000 |
| Cleaved PARP | Rabbit | Cell Signaling Technology | 1:1000 |
| Cleaved Caspase 3 | Rabbit | Cell Signaling Technology | 1:1000 |
| PDK1 | Rabbit | Cell Signaling Technology | 1:1000 |
| p-PDK1$^{S241}$ | Rabbit | Cell Signaling Technology | 1:1000 |
| p-RSK2$^{S227}$ | Rabbit | Cell Signaling Technology | 1:1000 |
| Actin | Mouse | Sigma | 1:10,000 |
| P-TSC2 | Rabbit | Cell Signaling Technology | 1:1000 |
| c-Myc | Rabbit | Cell Signaling Technology | 1:1000 |

Apoptosis and cell cycle assays. To measure apoptosis, we performed terminal deoxynucleotidyl transferase dUTP nick end labeling (TUNEL) staining with an APO-BRDU Kit (BD Biosciences, San Jose, CA) and Annexin V/propidium iodide staining with an FITC Annexin V Apoptosis Detection Kit (BD Pharmingen, San Diego, CA) as described previously (Chandarlapaty et al., 2011). For the cell cycle analysis, cells were harvested, fixed, incorporated with bromodeoxyuridine (BrdU), and stained with 7-aminoactinomycin D using a BrdU Flow Kit (BD Biosciences, San Jose, CA). Data were acquired with a three-laser, 10-color Gallios flow cytometer (Beckman Coulter, Brea, CA) and analyzed using Kaluza software (Beckman Coulter, Brea, CA). All apoptosis assays were performed in triplicate, and each test was completed twice on different days.

Colony formation assays. HNSSC cells were seeded in 60-mm plates. One day later, the cells were treated with DMSO or the indicated drugs for 48 hours. The medium was changed, and the cells were incubated in drug-free medium for 14-21 days. The cell colonies were then washed, fixed in 10% formaldehyde, and stained with crystal violet (0.5% w/v). Colony images were taken with a GelCount Tumour Colony Counter (Oxford Optronix Ltd., San Francisco, CA). The total colony number and area were counted and analyzed using the ImageJ software program (National Instividin-conjugated horseradish peroxidase/diaminobenzidine was detected using a TUNEL apoptosis detection kit (Trevigen, Gaithersburg, MD, USA). Images were taken at 40× magnification, and Image J software was used to calculate the percentage of TUNEL-positive cells.

Statistical analysis. We used the beta-uniform mixture model to control the false discovery rate (Kalu et al., 2018). To identify differentially expressed features between groups, we applied modified two-sample t-tests using the Limma package in R. We used the Fisher exact test and Wilcoxon rank-sum test to evaluate associations between molecular characteristics and drug sensitivities. In vitro experiment results were compared using a two-sample t-test and two-way analysis of variance corrected for multiple comparisons with the Tukey method in GraphPad Prism 7 (La Jolla, CA). In vivo experiment results were analyzed using a linear mixed model in R.

Example 1—Testing of Efficacy of the Preferred Dual PI3K/mTOR Inhibitor Bimiralisib in a Panel of 69 HNSCC Cell Lines We observed a decrease in pAKT, pS6 and p4EBP1 upon treatment with bimiralisib (FIG. 1). We tested 69 HNSCC cell lines for sensitivity to bimiralisib and found that the majority were sensitive and 66 cell lines had IC$_{50}$ values <3

μM and 36 cell lines had $IC_{70}$ values <3 μM. To identify potential biomarkers of response to bimiralisib, we compared the drug sensitivity to baseline gene and protein expression as well as gene mutations. We found 3 proteins whose expression correlated with sensitivity to bimiralisib: CHK2, caveolin, and E2F1 while the sensitivity did not correlate with mutations in TP53, CDKN2A, CASP8, HRAS, PIK3CA), FAT1, AJUBA, FBXW7, KRAS, MAML. However, the sensitivity did best correlate with the presence of a NOTCH1 mutation (Table 2) indicating that there is sensitivity to bimiralisib in cells having NOTCH1 mutations.

IC50 values were estimated from the best-fit dose-response model selected by calculating residual standard error using the R packages Dose Finding and drc (dose response curve) (Ritz and Streibig 2005, Bornkamp, Bretz et al. 2011). All experiments were done in duplicate and we compared the response between two experiments using concordance correlation coefficient (CCC). The CCC can be computed based on the scaled response as well as original unscaled response. The scaled version should be more relevant since this is actually the data used in IC estimation. Gene expression data were available for 49 of the 69 cell lines treated with bimiralisib. Reverse phase protein array (RPPA) data were obtained as previously described (Byers, Wang et al. 2012, Byers, Diao et al. 2013, Akbani, Ng et al. 2014) and available for 62 lines tested with bimiralisib. To identify differentially expressed features between the comparative groups, we applied modified two-sample t-tests using the Limma package. The beta-uniform mixture (BUM) model, described by Pounds and Morris was used to control false discovery rate (FDR) (Pounds and Morris 2003).

TABLE 2

Bimiralisib sensitivity and NOTCH1 Mutations

|  | Sensitive | Resistant |
|---|---|---|
| WT | 18 | 20 |
| Mutant | 12 | 3 |

P = 0.0368

Example 2—Exome Sequencing (WES) on 66 Established HNSCC Lines

Figure 2A:
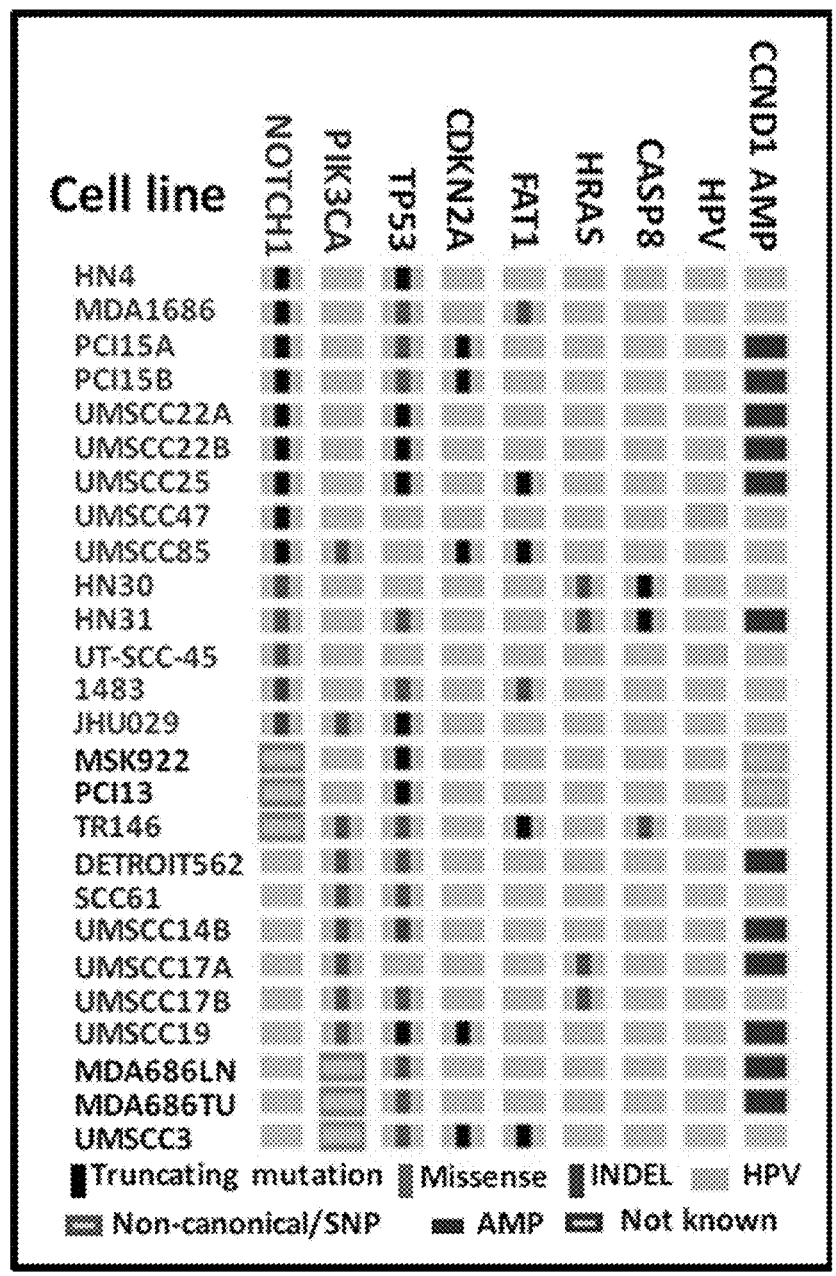
FIG. 2A: Genotype of HNSCC cell lines. Whole exome sequencing (WES) was performed on 66 established HNSCC lines. A number of these cell lines were mutant for NOTCH1 or had PIK3CA mutations in known hotspots, but they also had additional driver mutations frequently observed in HNSCC.
Figures 2B, 3A:
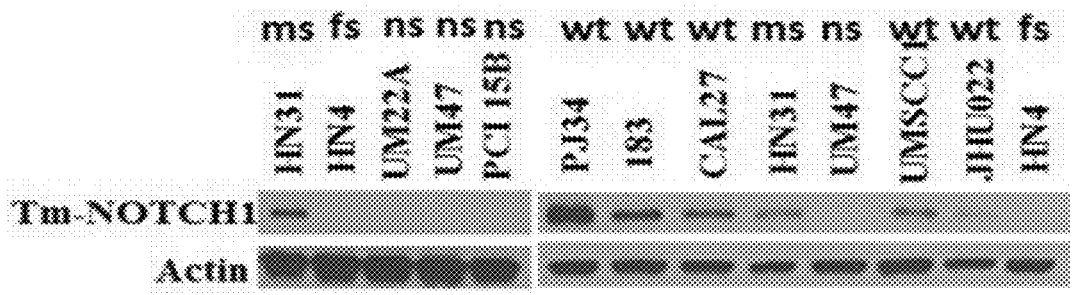
FIG. 2B: Genotype of HNSCC cell lines. Non-canonical mutations or possibly SNPS were excluded from the analysis. a: non-canonical mutation excluded from analysis; b: possible SNP excluded from NOTCH1 analysis; *non characterized NOTCH1 mutation.
FIG. 3A: Loss and restoration of NOTCH1 expression. Total NOTCH1 is absent from cells with truncating mutations (ns=non sense mutation, fs=frames shift mutation), but present in wt cells or in HN31 with a missense (ms) mutation.
Figures 3B, 3C:
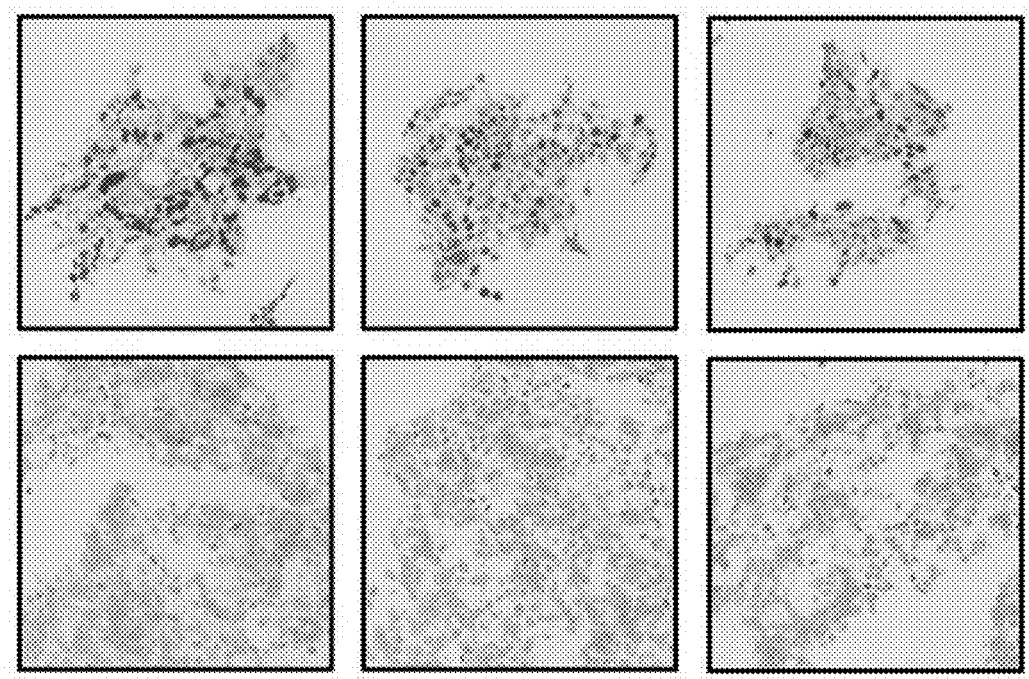
FIG. 3B: Loss and restoration of NOTCH1 expression. Infection with full length wt NOTCH1 (NFL1) but not empty vector (MigR1) restores NOTCH1 activation detected as cleaved-NOTCH1. Jag1=NOTCH ligand. FC=protein; UN=untreated.
FIG. 3C: Loss and restoration of NOTCH1 expression. The presence and residual levels of activated NOTCH1 is assessed by determination of the expression of cleaved NOTCH1 (cl-NOTCH1) in tumors or tumor cells, typically and preferably, by immunohistochemistry (IHC) according to published methods (Kluk, Ashworth et al. 2013, Rettig, Chung et al. 2015), with an antibody that specifically detects cl-NOTCH1. Upper panel shows section of paraffin-embedded pellets of FADU HNSCC cell line expressing NOTCH1wt. Lower panel shows section of paraffin-embedded pellets of FADU HNSCC cell line where the NOTCH1wt was deleted by CRISPR/Cas9.

To address the function of NOTCH1 mutations and other genes frequently altered in HNSCC, we performed whole exome sequencing (WES) on 66 established HNSCC lines. A number of these cell lines were mutant for NOTCH1 or had PIK3CA mutations in known hotspots, but they also had additional driver mutations frequently observed in HNSCC (FIG. 2) and were therefore reflective of genomic subtypes found in patients. Most NOTCH1 mutations in the HNSCC cell lines were truncating, and loss of NOTCH1 protein was confirmed in four of the mutant cell lines tested (FIG. 3A). A missense mutation (C478F) that occurred in two cell lines derived from the same patient (HN31 and HN30) was confirmed to result in loss of NOTCH1 signaling upon ligand activation (FIG. 3B). Using an antibody that recognized only the activated form of NOTCH1 (cl-NOTCH1), no signal was present in mutant UM47 (G192*) or HN31 (C478F) (FIG. 3B) when cells were cultured on immobilized NOTCH1 ligand Jagged1 (Jag1) after infection with an empty control retrovirus (MigR1); however, infection with retrovirus restoring wild type (wt) full-length NOTCH1 (NFL1) resulted in cl-NOTCH1 that increased greatly in cells grown on Jag1 (FIG. 3B). The presence of activated NOTCH1 are assessed by determination of the levels of expression of cleaved NOTCH1 (cl-NOTCH1) in the nucleus of tumor cells by immunohistochemistry (IHC) according to published methods (Kluk, Ashworth et al. 2013, Rettig, Chung et al. 2015) with an antibody that specifically detects cl-NOTCH (NICD; Notch intracellular domain) which is formed following activation of NOTCH1 at the plasma membrane (Nowell and Radtke 2017) (FIG. 3C).

Figure 4A:
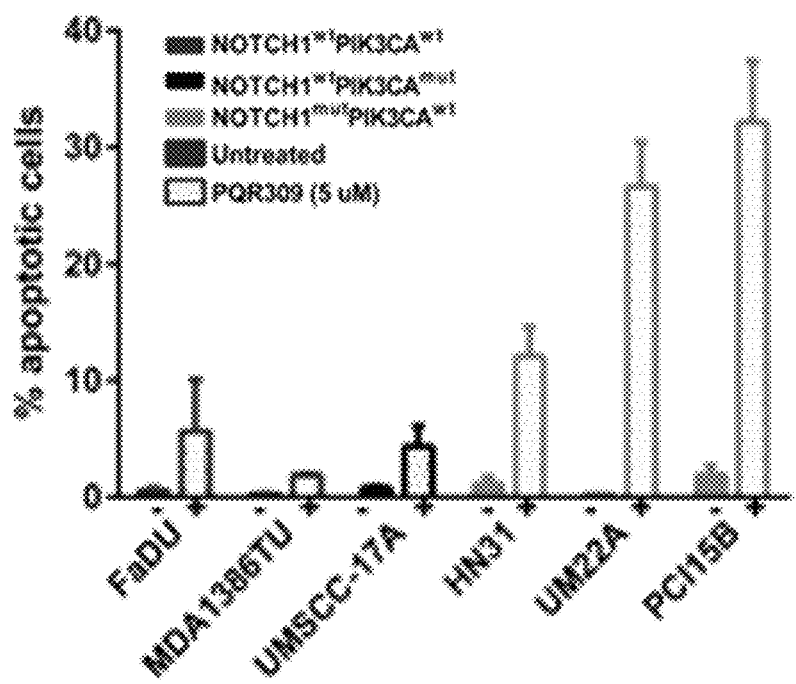
FIG. 4A: HNSCC cells with NOTCH1-LoF mutants are more sensitive to bimiralisib than NOTCH1$^{wt}$ cells in vitro. Bimiralisib at 5 µM induces death in HNSCC cell lines with NOTCH1 mutations. Cell death as measured with BrdU TUNEL was significantly increased in HNSCC cell lines with NOTCH1 mutations (dotted) but not in HNSCC lines with wt NOTCH1 (grey) or PIK3CA mutations (black) 48 hours after treatment with bimiralisib. Apoptotic death in NOTCH1 mutants, but not wt cell lines, was confirmed with cleaved PARP and Caspase 3.
Figure 4B:
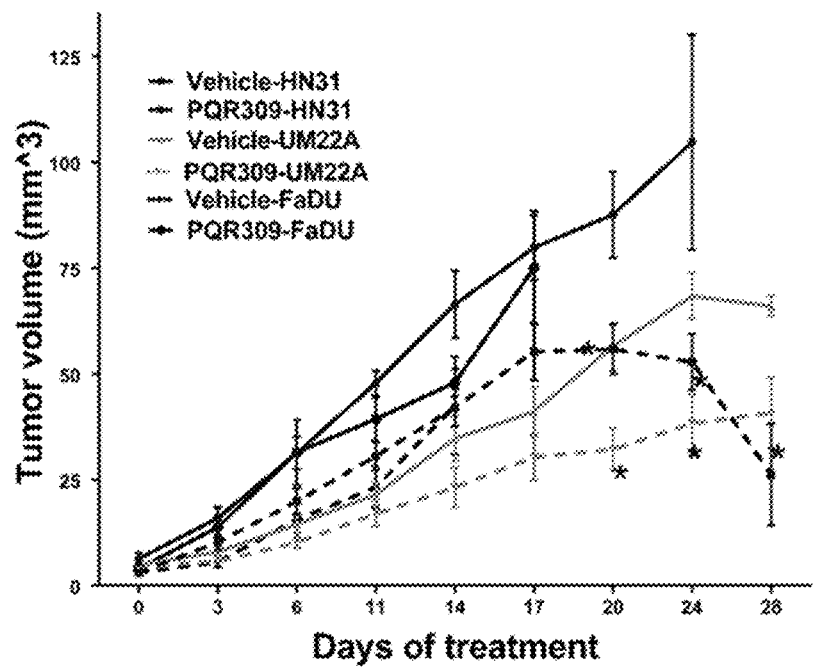
FIG. 4B: HNSCC tumors harboring NOTCH1-LoF mutants are more sensitive to bimiralisib than NOTCH1$^{wt}$ cells in vivo. Bimiralisib (50 mg/kg QD, PO) treatment in NOTCH1$^{mut}$ and WT orthotopic xenografts in vivo. Reduction in tumor growth was seen in mutant lines compared to FaDU. In detail, in vivo response of bimiralisib (50 mg/kg) PO once daily against 2 orthotopic tongue xenograft model with 2 NOTCH1mutant lines. After the growth of the xenografts, the mice were randomized and treated with bimiralisib daily for 28 days. The figure shows tumor growth curve over time. The solid lines are tumor volume of UM22A and HN31 (NOTCH1 inactivating mutants) when treated with vehicle or when FaDu tumors with NOTCH1wt were treated once daily with 50 mg/kg bimiralisib PO. Dotted lines are the tumor volumes of UM22A and HN31 after PO once daily treatment with 50 mg/kg bimiralisib.

Example 3—NOTCH1-LOF Mutants are More Sensitive than NOTCH1wt Cells to Drugs Targeting PI3K/mTOR Six different HNSCC cell lines with and without NOTCH1 mutations were analyzed for their sensitivity towards bimiralisib. At 5 μM bimiralisib induces only cell death in HNSCC cell lines with NOTCH1 mutations as determined by BrDU-TUNEL staining, while in HNSCC NOTCH1wt bimiralisib arrested cell lines in G1/S. Cell death as measured by BrdU-TUNEL was significantly increased in HNSCC cell lines with NOTCH1 mutations but not in HNSCC lines with NOTCH1wt or PIK3CA mutations (FIG. 4A). To further validate these findings an in vivo experiment was performed by sublingual implantation of 2 NOTCH1 mutant HNSCC cell lines (UM22A and HN31) and one NOTCH1wt HNSCC cell line (FaDu) (FIG. 4B) followed by once daily PO treatment with bimiralisib (50 mg/kg) for 28 days. This regiment of bimiralisib was well tolerated during the whole treatment period of 28 days without body weight loss. There was significant reduction of tumor growth after treatment with bimiralisib drug in the 2 HNSCC tumors that harboured the NOTCH1 inactivating mutations (*p<0.05) while the growth of the HNSCC tumor harboring the NOTCHwt was not affected by the bimiralisib treatment. These data clearly indicate that that cells harboring NOTCH1 inactivating mutations are sensitive and vulnerable to the treatment of bimiralisib both in vitro and in vivo. In summary these data demonstrate that cell harboring NOTCH1-LoF mutation are sensitive both in vitro and in vivo to dual PI3K/mTOR inhibitor bimiralisib.

Figures 12A, 12B:
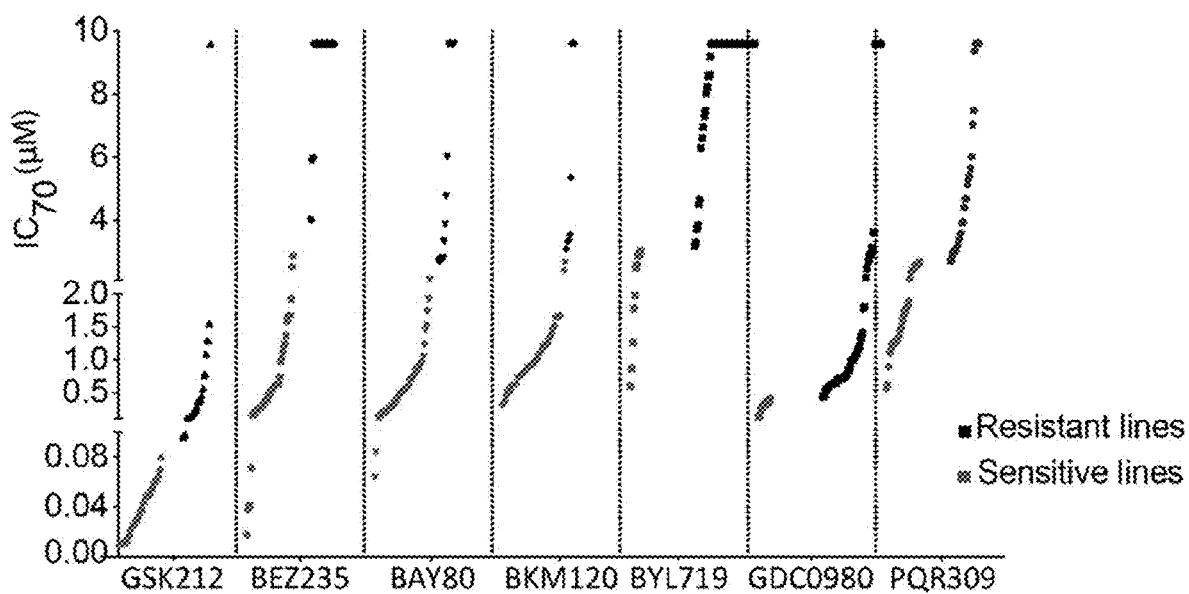
FIGS. 12A-12C: Landscape of sensitivity to PI3K/mTOR pathway inhibitors in head and neck squamous cell carcinoma (HNSCC) cell lines.
Figure 12C:
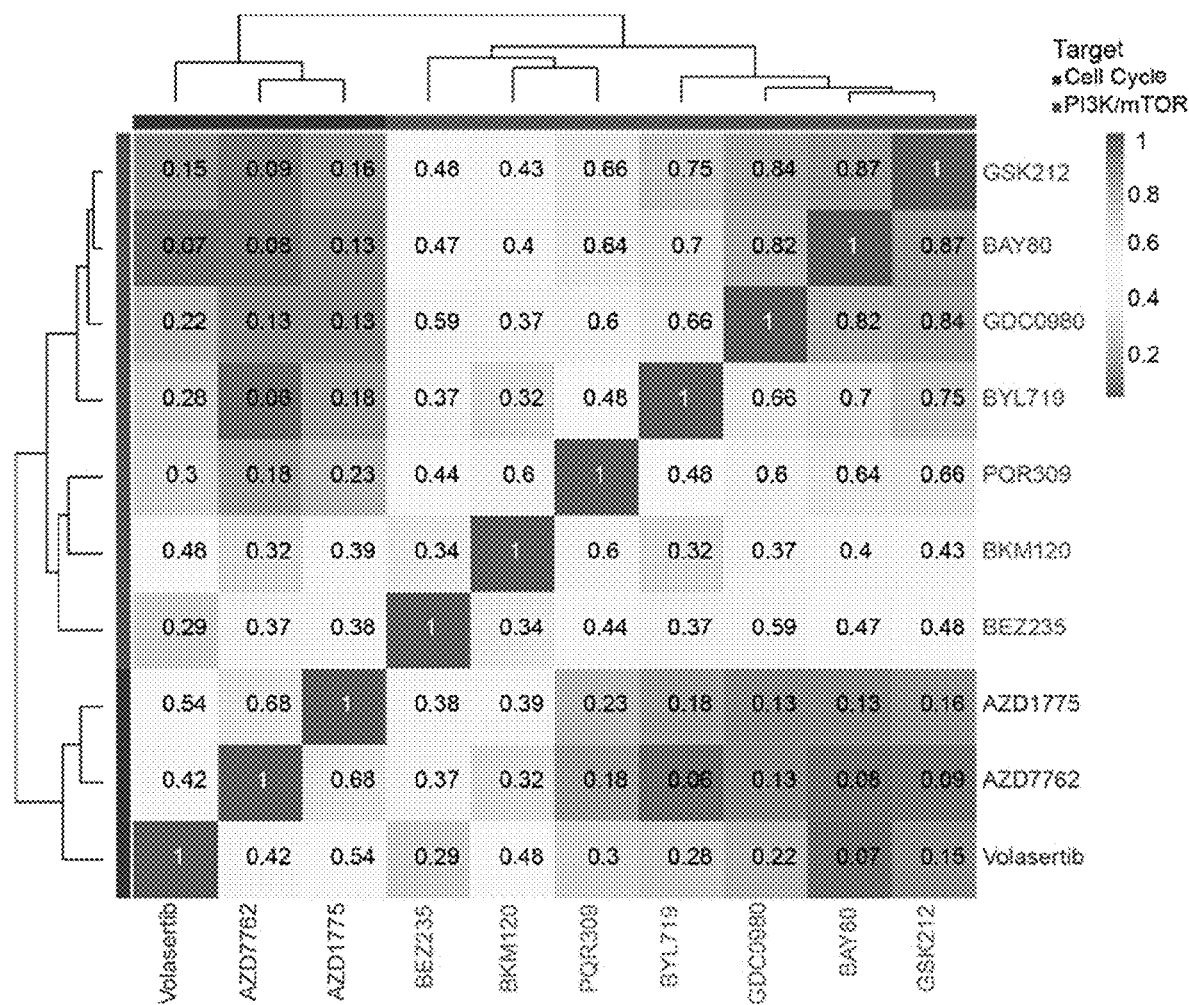

Example 4—HNSCC Cell Lines with LOF NOTCH1 Mutations are Sensitive to PI3K/mTOR Pathway Inhibitors In Vitro To identify novel predictive therapeutic vulnerabilities linked to PI3K/mTOR pathway inhibition, 59 HNSCC cell lines were treated with seven different PI3K/mTOR pathway inhibitors that were in clinical development at the start of this study (Munster et al., 2016; Bendell et al., 2015; Liu et al., 2013; Bendell et al., 2012; De Buck et al., 2014; Wicki et al., 2018; Beaufils et al., 2017. Of the drug-cell line combinations, 95% met the predefined quality control cutoff. The HNSCC cell lines exhibited diverse sensitivity to PI3K/mTOR pathway inhibitors (FIGS. 12A and 12B). Because the dose-response curves for PI3K/mTOR pathway inhibitors often plateau near the $IC_{50}$ values (Mazumdar et al., 2014), the more robust $IC_{70}$ and AUC values were used as parameters for drug potency as described previously (Ferrarotto et al., 2016). Cell lines were classified as sensitive based on $IC_{70}$ values less than the peak plasma concentration for each drug. To determine if cross-comparison of the PI3K/mTOR inhibitors as a class was feasible, their drug sensitivity patterns were compared with those of three cell cycle kinase inhibitors tested previously (Zhang et al., 2017). The PI3K/mTOR pathway inhibitors clustered separately from the cell cycle inhibitors (FIG. 12C).

Figure 6A:
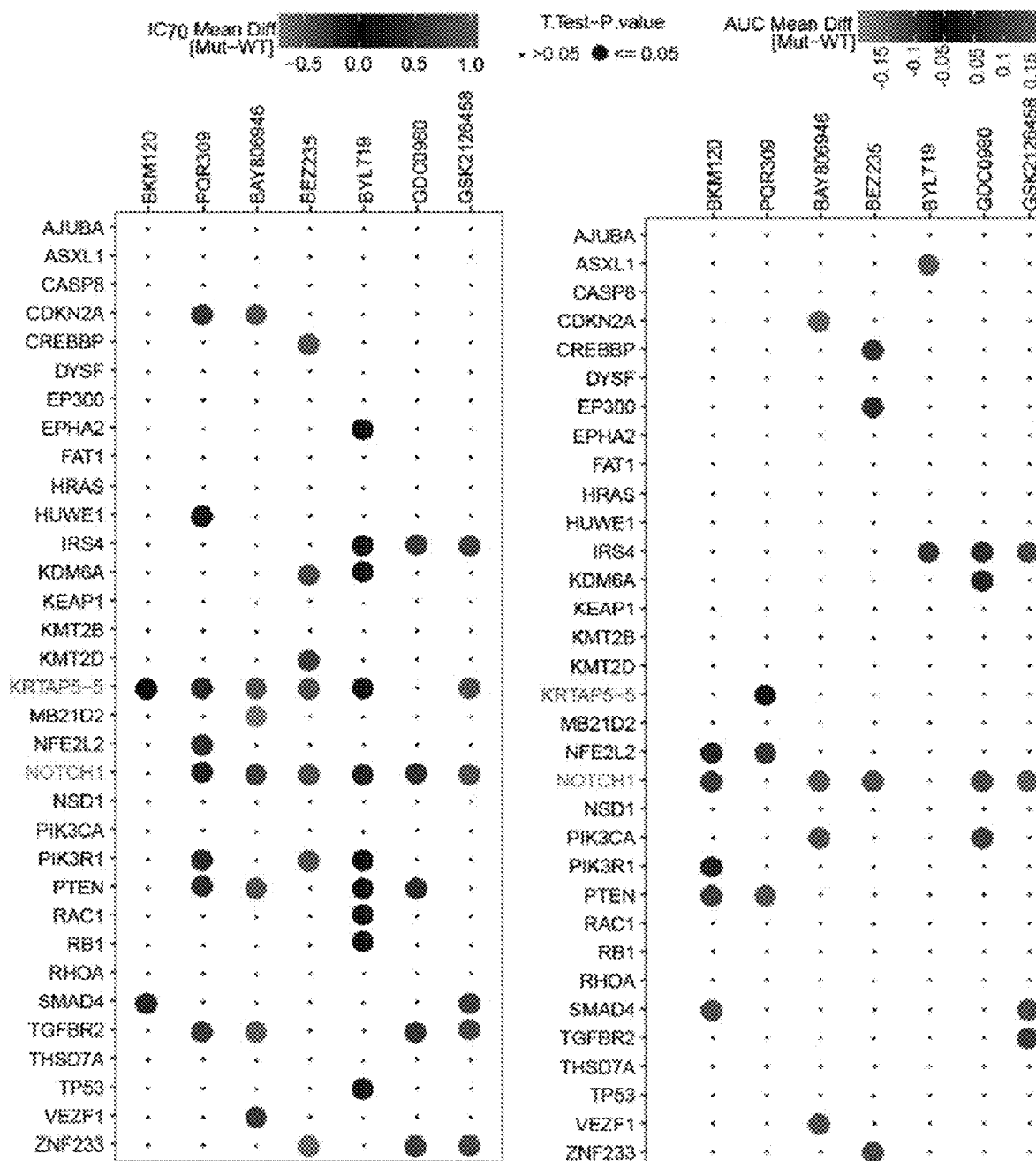

Drug sensitivity was then compared to common driver genes identified in HNSCC tumors from The Cancer Genome Atlas (TCGA) (Zhang et al., 2017). The cell lines did not have any mutations in 11 of the top 50 mutated genes, and 6 genes were mutated in only one cell line, precluding comparison. Of the 515 sequenced TCGA HNSCC tumors, 92% had a mutation in at least one of the remaining 33 genes, demonstrating that the cell lines were genomically representative of HNSCC patients. Of the 33 genes, only mutated NOTCH1 and KRTAP5-5 were significantly correlated with sensitivity to six of the seven drugs (FIG. 6A). KRTAP5-5 was not studied further because it is mutated in only two cell lines and 6% of HNSCC patients (Cancer Genome Atlas, 2015; Agrawal et al., 2011).

Figure 6B:
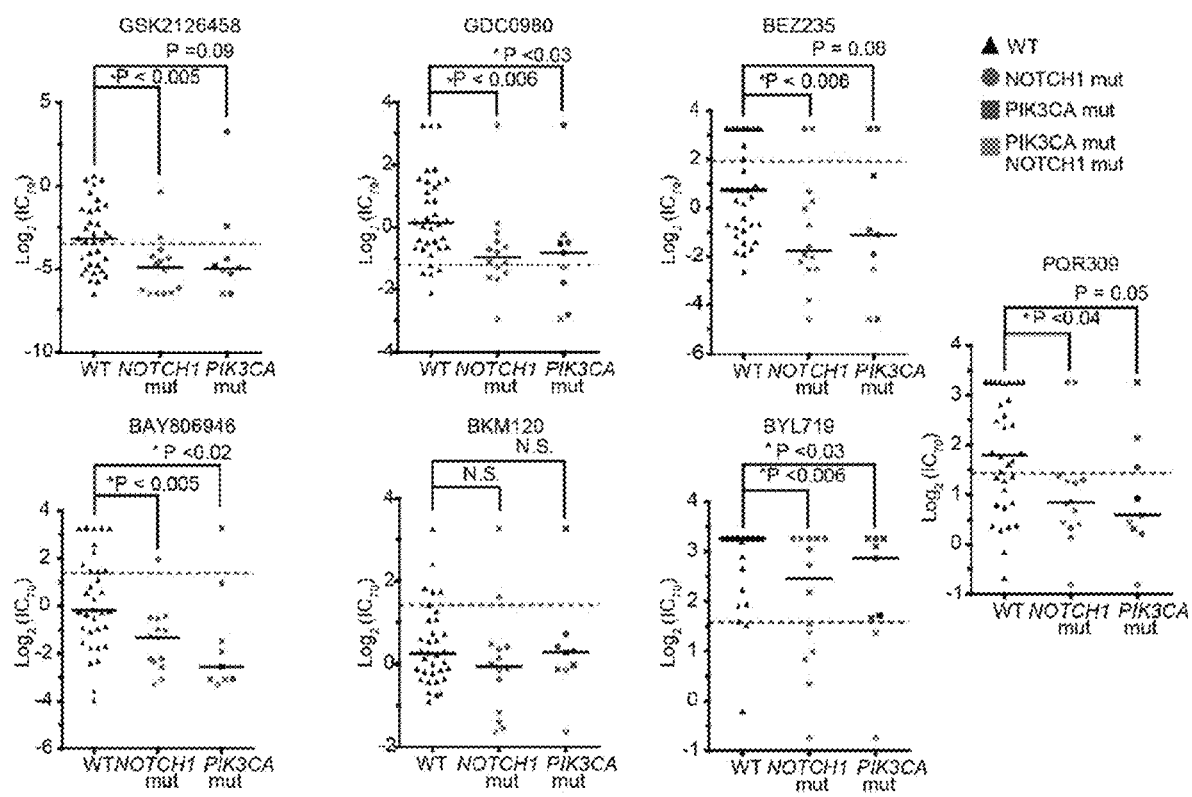

Because PIK3CA mutations predict pathway inhibitor response in HNSCC (Mazumdar et al., 2014; Keysar et al., 2013; Li et al., 2014), their relationship with drug sensitivity was specifically examined. No consistent correlation was found between PIK3CA mutations and drug sensitivity when all 12 PIK3CA$^{MUT}$ cell lines were included (FIG. 6A). Compared with PIK3CA$^{WT}$ cell lines, PIK3CA$^{MUT}$ HNSCC cell lines (excluding three cell lines with uncharacterized mutations) were significantly more sensitive to four drugs and substantially more sensitive to two drugs (FIG. 6B). The median $IC_{70}$ values of six drugs for the NOTCH1$^{MUT}$ lines were significantly lower than those of the drugs for the NOTCH1$^{WT}$ lines; the seventh drug, BKM120, was almost universally effective in HNSCC cell lines, likely owing to its multiple off-target effects (Bohnacker et al., 2017). Two cell lines harbored both NOTCH1 and PIK3CA mutations and were sensitive to all the inhibitors tested. There was no mutual exclusivity of these two mutations in the 515 sequenced TCGA HNSCC patient samples, but there was a tendency towards co-occurrence (available on the world wide web at cbioportal.org: accessed on Sep. 15, 2018).

Figure 13A:
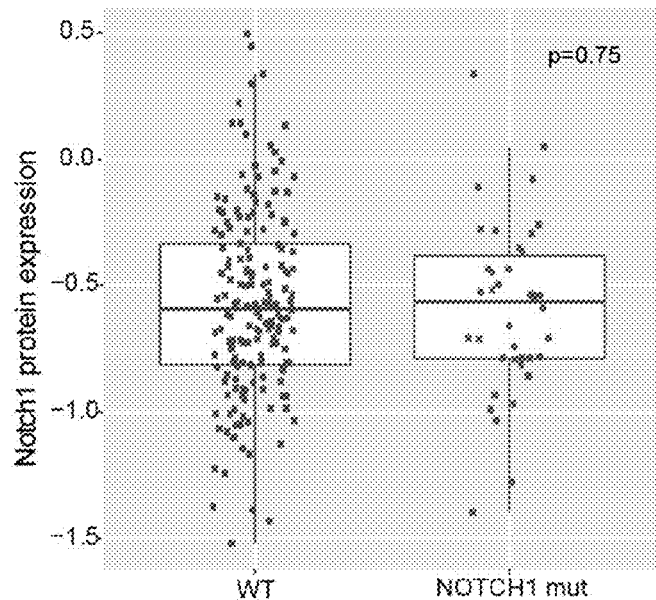
FIGS. 13A-13E: Relationship of NOTCH1 protein expression, activation, and mutation in head and neck squamous cell carcinoma (HNSCC) tumors and cell lines.
Figure 13B:
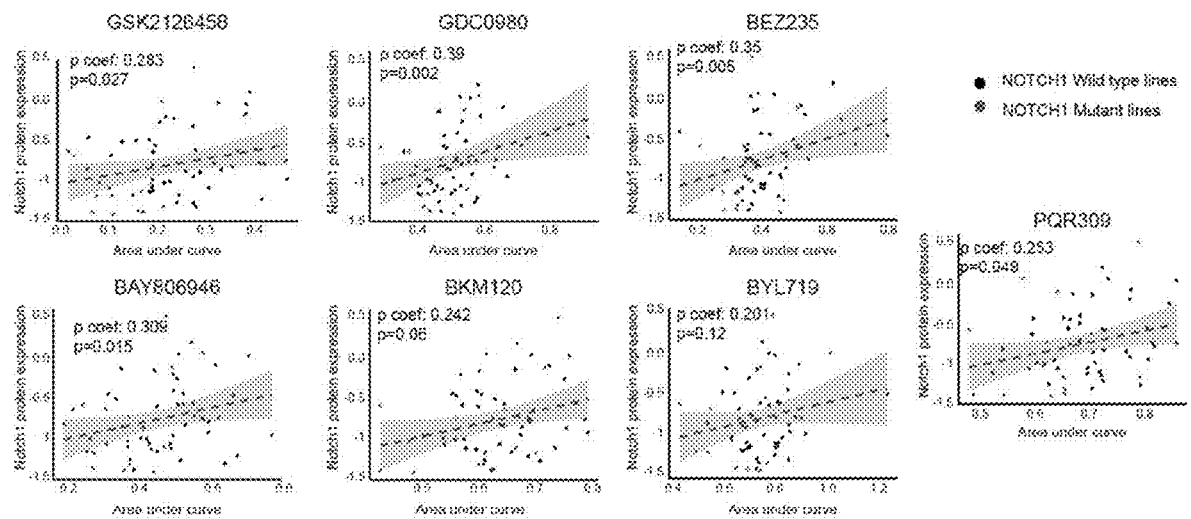
Figure 13C:
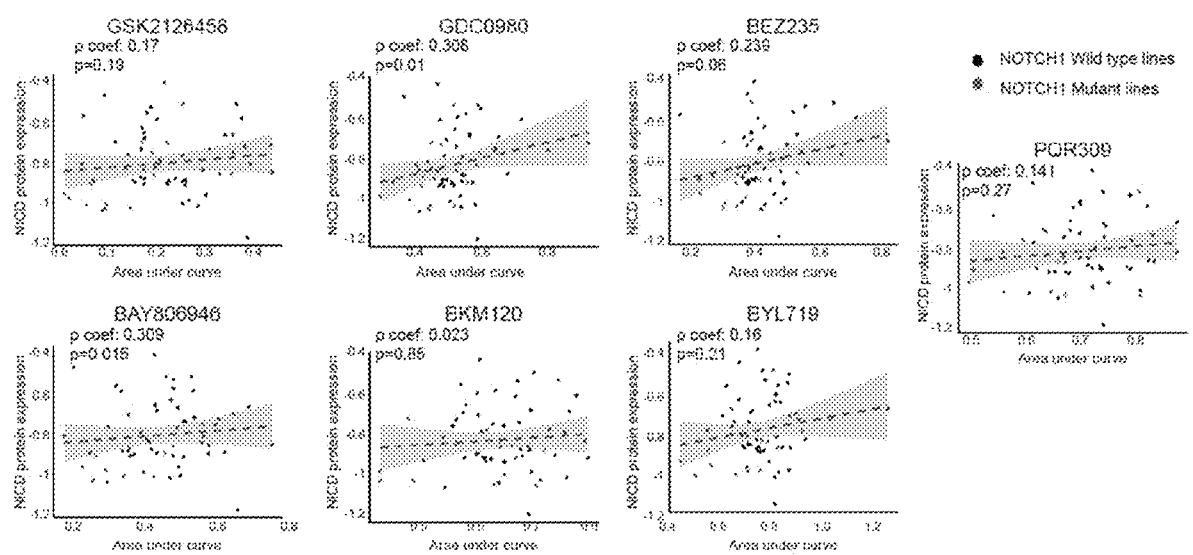
Figure 13D:
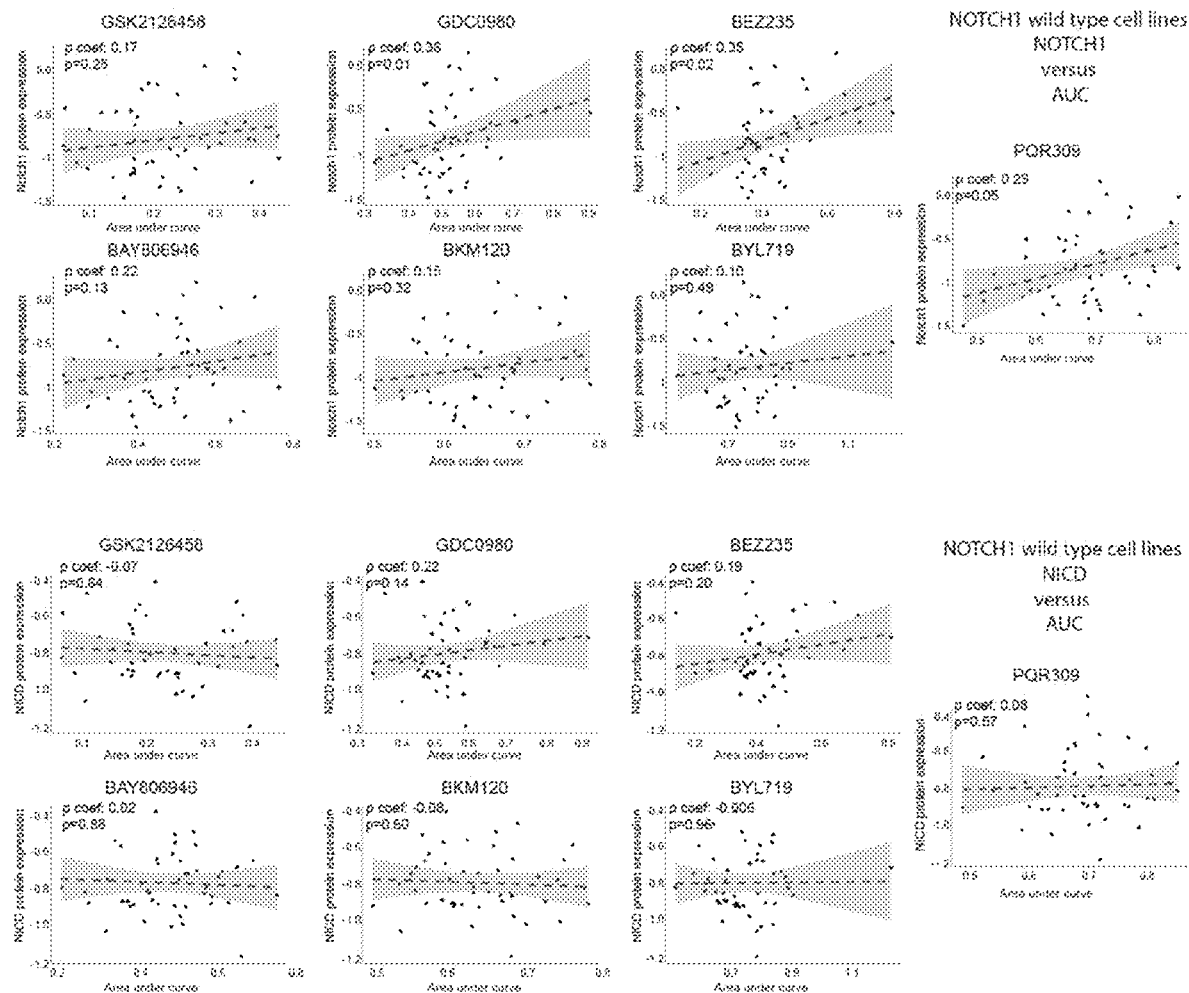
Figure 13E:
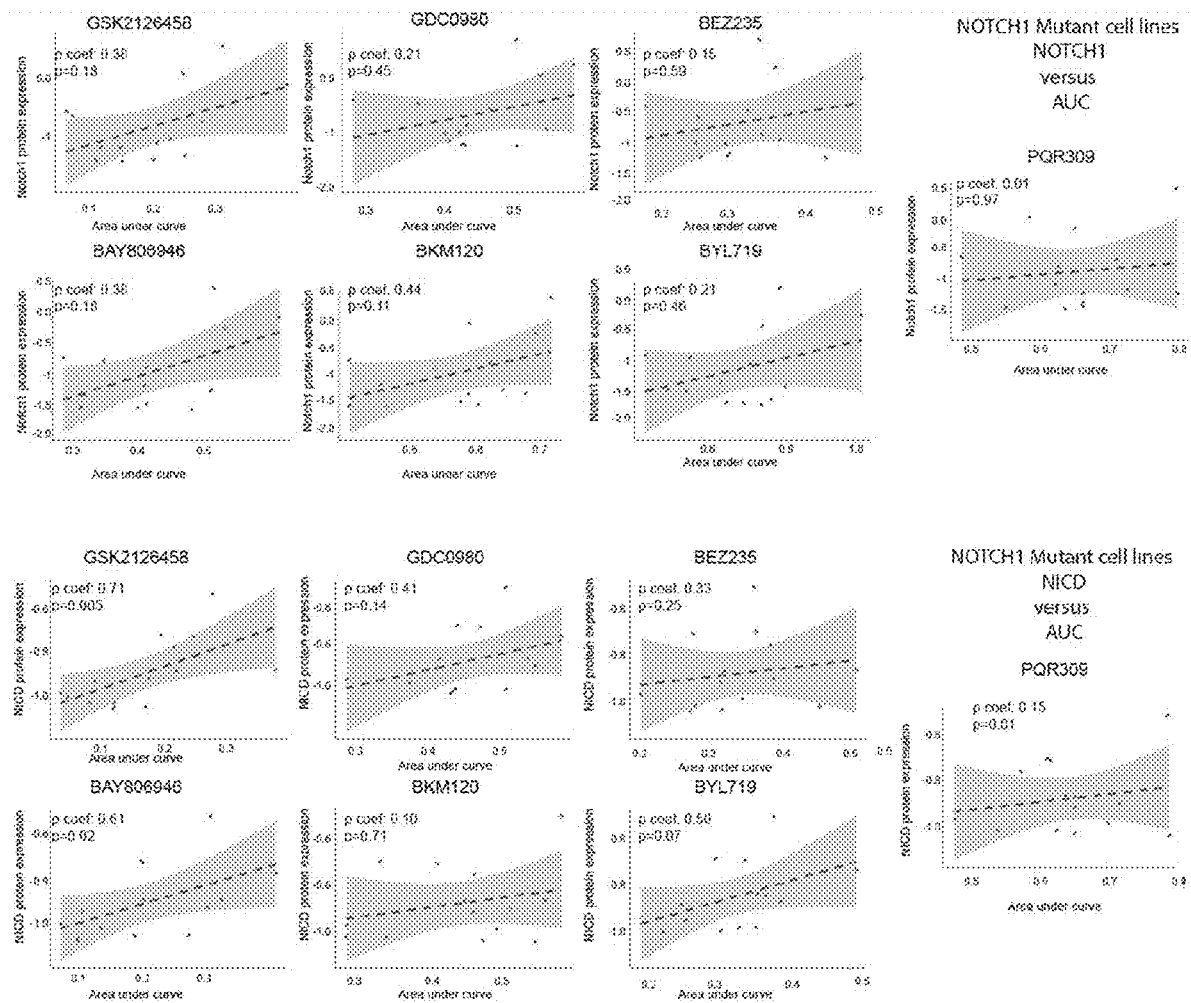

HNSCC patient samples have frequent truncating NOTCH1 mutations (Agrawal et al., 2011). The distribution of these mutations was found to be very different from that of the activating mutations found in T-cell acute lymphoblastic leukemia (T-ALL); mutations in HNSCC cell lines were similar to the mutation pattern in HNSCC patient samples (FIGS. 6C and 6) (Hales et al., 2014). Of the 17 HNSCC lines found to harbor NOTCH1 mutations, six had truncating mutations (nonsense mutations and deletions) and 11 had missense mutations. Of those 11, three were excluded from analysis because their NOTCH1 alterations occurred in the nuclear regulatory domain and more likely represented single-nucleotide polymorphisms. Of the 14 HNSCC lines with NOTCH1 LOF mutations (FIG. 6E), two had both bona fide NOTCH1 and PIK3CA mutations. Both NOTCH1 and cleaved NOTCH1 (NOTCH intracellular domain [NICD]) protein levels were lower in NOTCH1$^{MUT}$ lines than in NOTCH1$^{WT}$ lines, although the difference was not significant, likely owing to diverse protein expression levels in NOTCH1$^{WT}$ lines. However, a significant positive correlation between NICD and total NOTCH1 protein levels in the cell lines was found (FIG. 6F). TCGA HNSCC patient samples also showed diverse NOTCH1 protein expression levels regardless of NOTCH1 mutation status (FIG. 13A). NOTCH1 and NICD levels did not consistently correlate with drug sensitivity in NOTCH1$^{MUT}$ or NOTCH1$^{WT}$ lines (FIGS. 13B-13E).

Figure 14A:
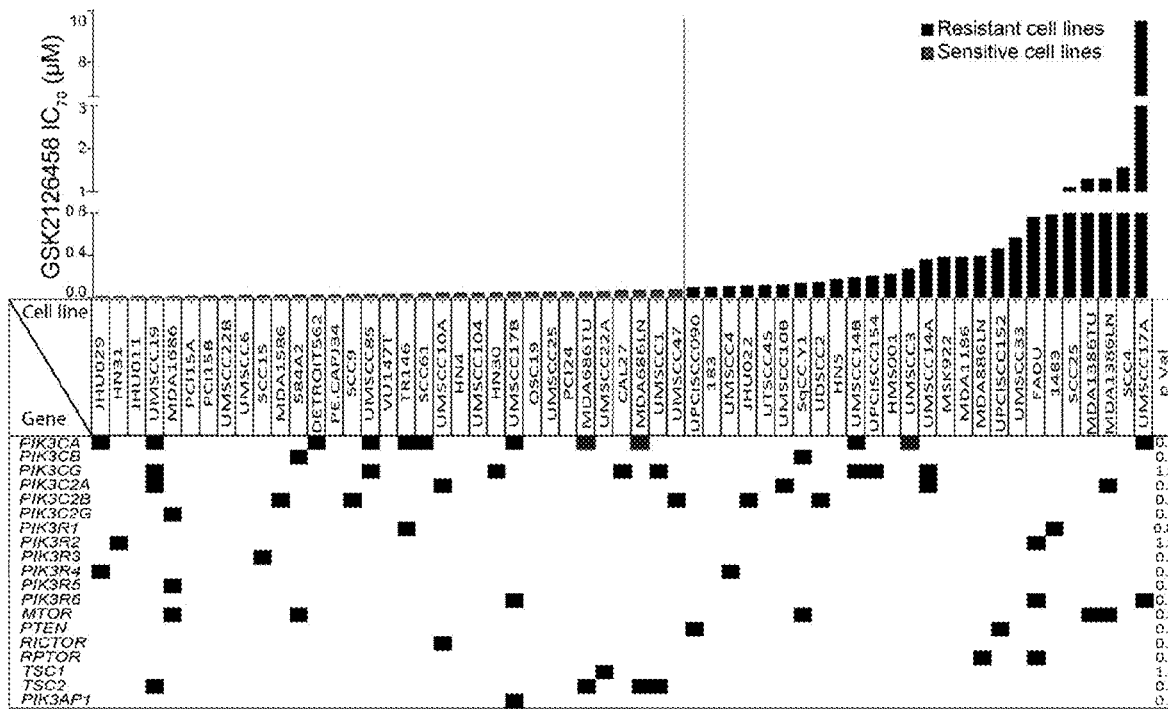
FIGS. 14A-C: Sensitivity to PI3K/mTOR pathway inhibitors is not significantly associated with PI3K/mTOR pathway alterations FIG. 14A. The heat map depicts the association between 19 genetic mutations in the PI3K/mTOR pathway (left column) and GSK2126458 sensitivity in 59 head and neck squamous cell carcinoma (HNSCC) cell lines. P values were calculated using the Fisher exact test; no significant associations were observed. Similar results were obtained with other PI3K inhibitors using the Wilcoxon rank-sum test (data not shown). Black boxes in the heatmap indicate mutations; white (i.e., absent) boxes indicate wild type genes; blue boxes indicate non-canonical mutations in the PIK3CA gene. The black vertical line in the bar graph indicates the peak plasma concentration of GSK2126458.
Figure 14B:
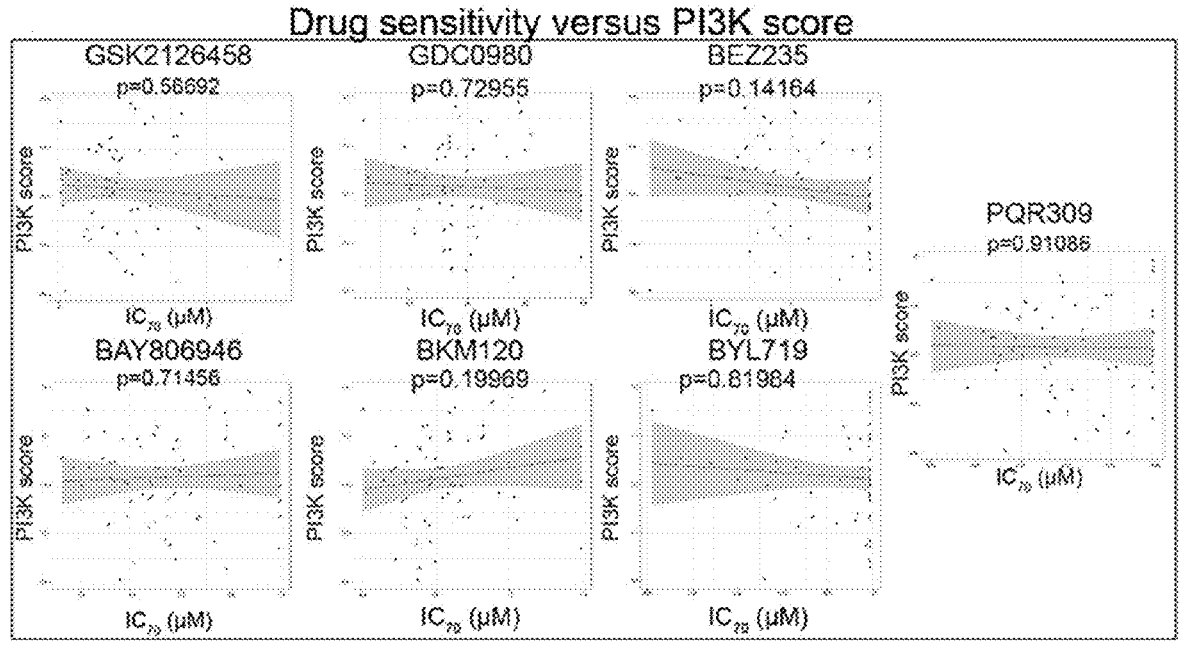
Figure 14C:
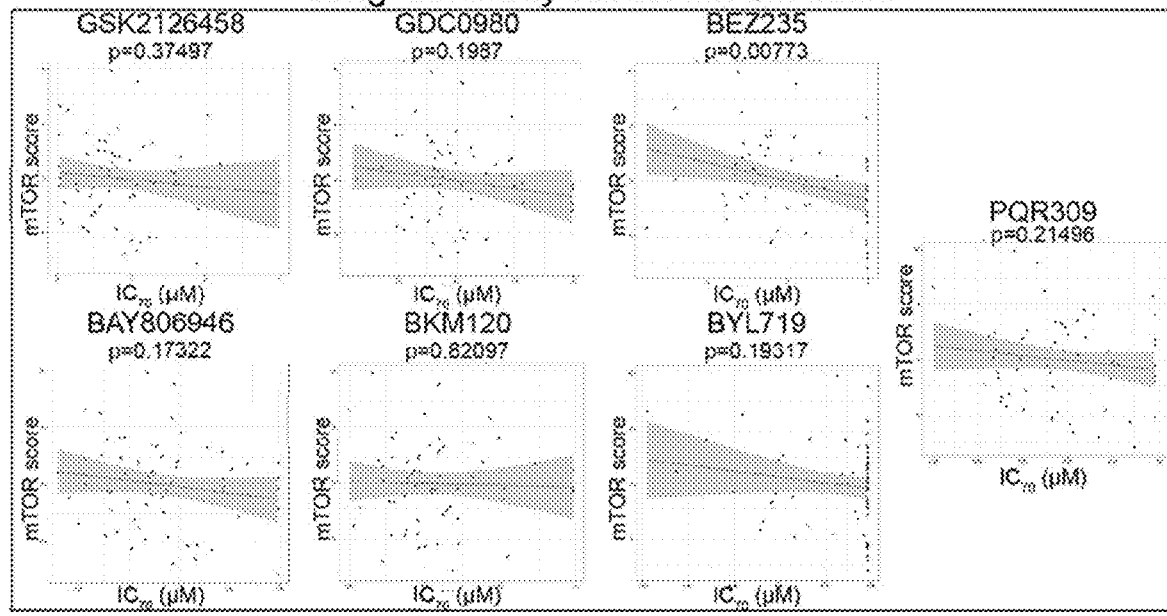
Figure 15A:
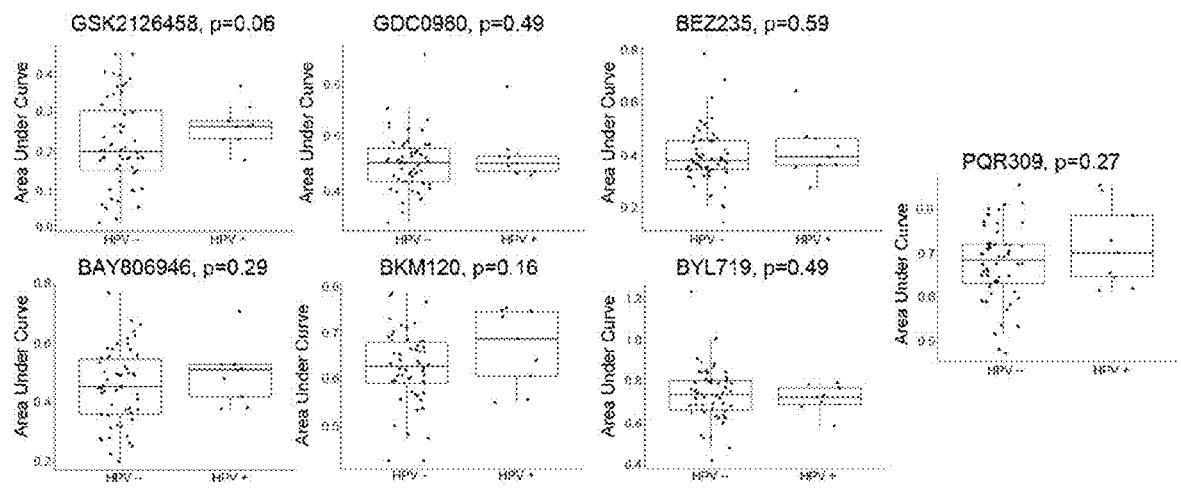
FIGS. 15A-15D: Association between sensitivity to PI3K/mTOR pathway inhibitors and human papilloma virus (HPV) status and proteomic scores in head and neck squamous cell carcinoma (HNSCC) cell lines.
Figure 15B:
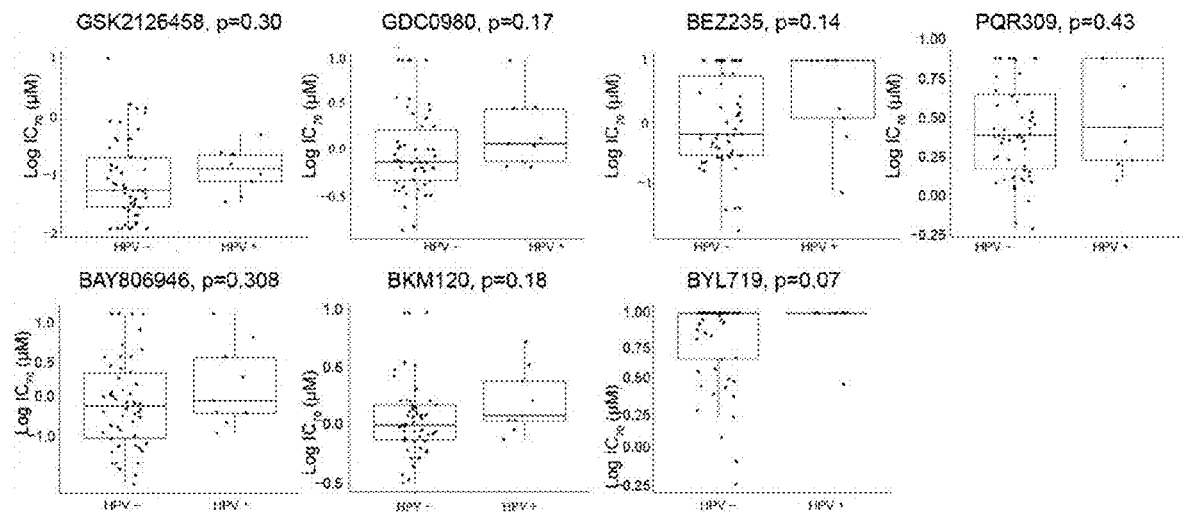

Example 5—Basal Activation of the PI3K/mTOR Pathway and HPV Status do not Predict Sensitivity to PI3K/mTOR Pathway Inhibitors The diverse drug sensitivity suggested that subsets of cell lines have inherent molecular therapeutic vulnerabilities. Although there was a trend for PIK3CA$^{MUT}$ cell lines to be more sensitive to PI3K/mTOR pathway inhibitors, none of the 28 mutations in the PI3K/mTOR pathway described previously (Lui et al., 2013) consistently correlated with drug sensitivity (FIG. 14A). Likewise, no significant correlation between the basal activation of the PI3K/mTOR pathway and drug sensitivity was found (FIGS. 14B and 14C). Of note, drug sensitivity did not correlate with RICTOR amplification or PDK1 protein or gene expression. Although HPV-positive HNSCC is molecularly distinct from HPV-negative HNSCC, drug sensitivity did not correlate with HPV status (FIGS. 15A and 15B).

Figure 15C:
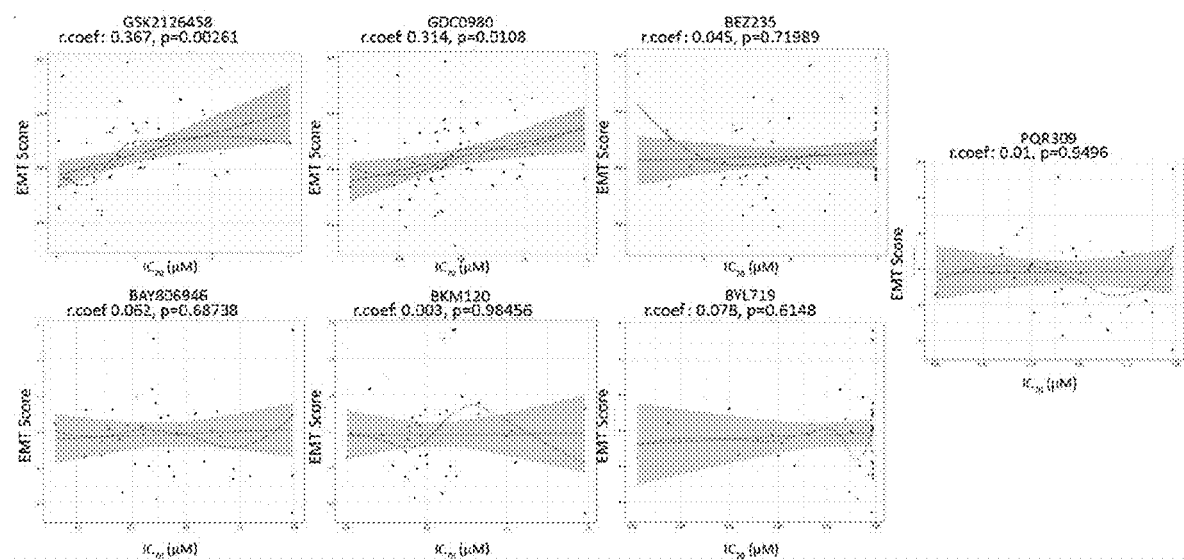
Figure 15D:
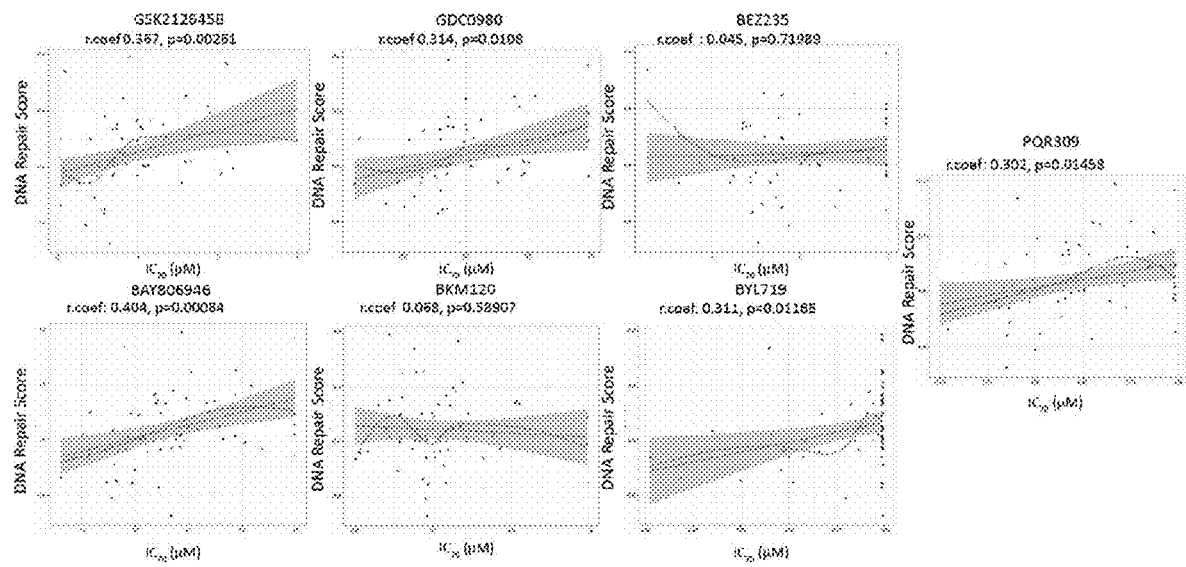

Basal gene and protein expression levels were also compared between resistant and sensitive cell lines and two additional proteomic scores (Ferrarotto et al., 2016). There was no robust correlation between DNA repair and epithelial to mesenchymal transition scores and sensitivity to drugs (r. coefficient <0.4) (FIGS. 15C-15D). These differentially expressed genes or proteins or these proteomic scores were not studied further owing to both inconsistency of the correlations and a lack of prior validation of the scores in HNSCC.

Figure 16A:
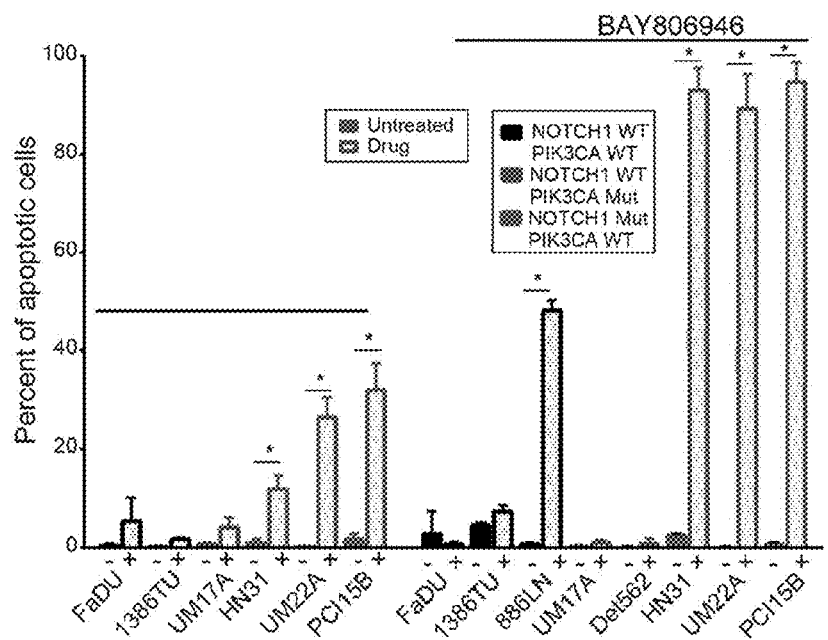
FIGS. 16A-16C: Effects of PI3K/mTOR signaling inhibition on the survival of NOTCH1MUT and NOTCH1WT head and neck squamous cell carcinoma (HNSCC) cell lines in vitro.
Figure 16B:
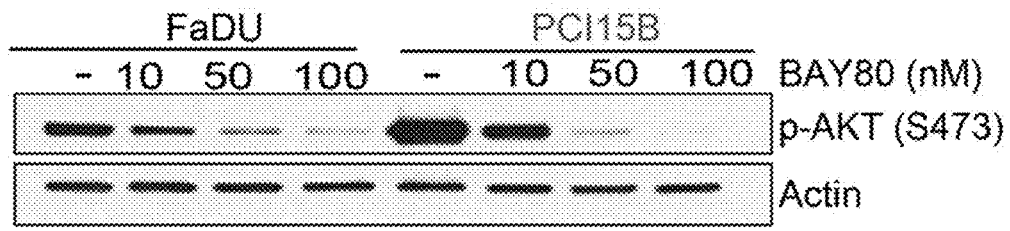
Figure 16C:
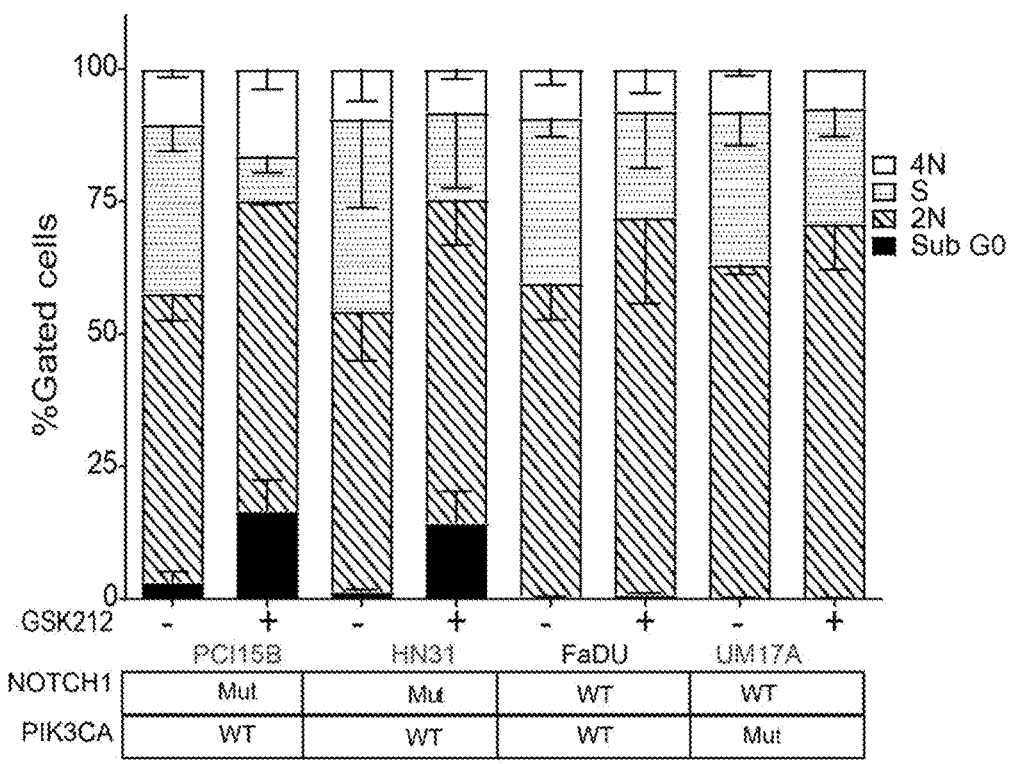
Figure 17A:
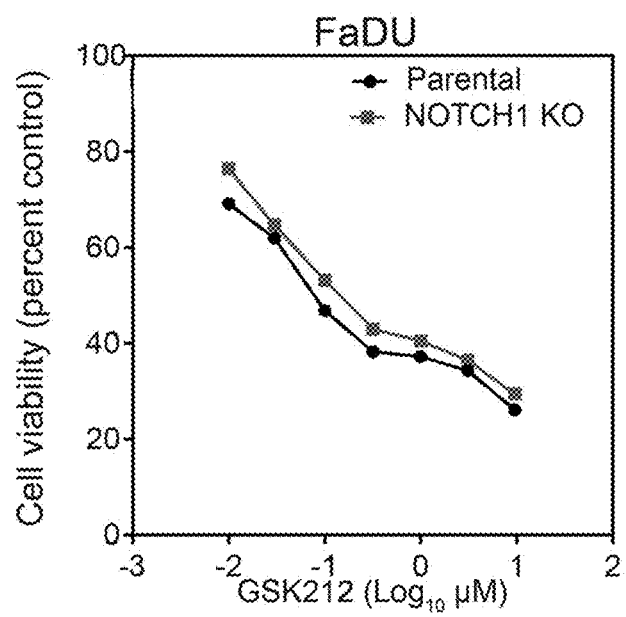
FIGS. 17A-17E: Effects of PI3K/mTOR pathway inhibition in NOTCH1WT HNSCC with and without NOTCH1 knock out (KO). Two NOTCH1WT HNSCC cell lines (FaDU and MDA686LN), parental cell lines, and NOTCH1 KO cell lines were treated with GSK2126458 (GSK212).
Figure 17B:
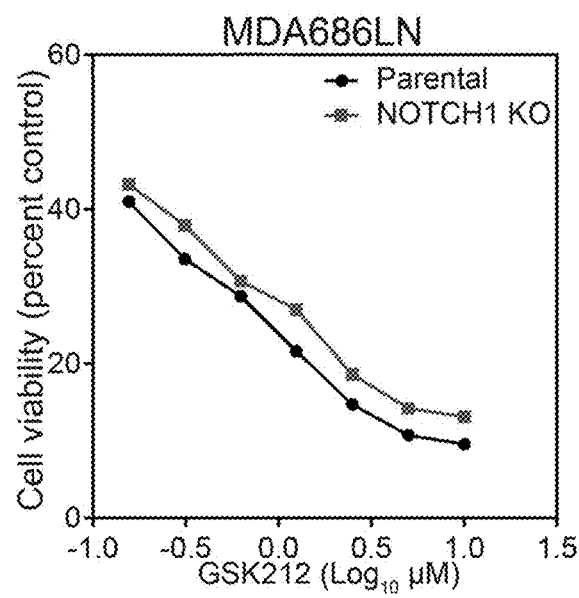
Figure 17C:
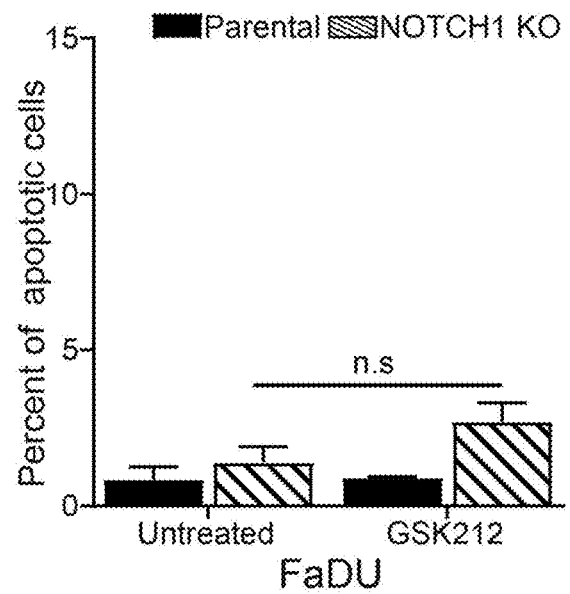
Figure 17D:
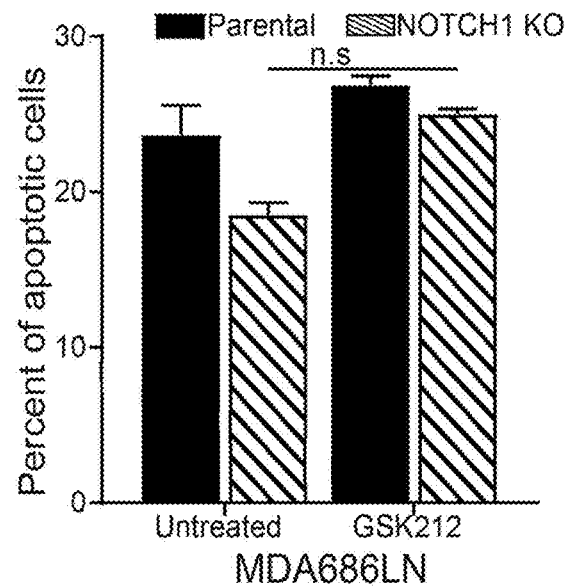
Figure 17E:
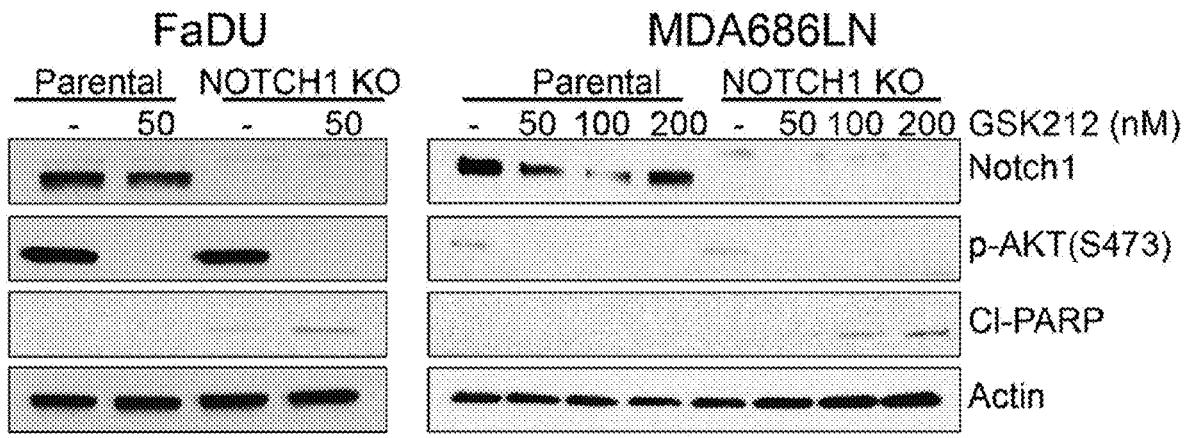

Example 6—PI3K/mTOR Pathway Inhibition Induces Apoptosis and Reduces Clonogenic Growth in NOTCH1$^{MUT}$ Cell Lines The susceptibility of NOTCH1$^{MUT}$ HNSCC to PI3K/mTOR inhibition was then validated with GSK2126458. GSK2126458 induced significant apoptosis in all NOTCH1$^{MUT}$ lines tested; no apoptosis was detected in the two NOTCH1$^{WT}$/PIK3CA$^{WT}$ lines or three NOTCH1$^{WT}$/PIK3CA$^{MUT}$ lines (FIGS. 2A and 2B). BAY806946 elicited similar results (FIG. 16A). Consistent with these data, GSK2126458, even at concentrations well below the peak plasma concentration value, significantly reduced the number of colonies formed and the total cell number in NOTCH1$^{MUT}$ lines compared with NOTCH1$^{WT}$ lines (FIG. 2C). GSK2126458 induced G1 arrest in all cell lines but increased the sub-G0 fraction in only NOTCH1$^{MUT}$ lines (FIG. 16C). GSK2126458 had dose-dependent target inhibition in representative NOTCH1$^{WT}$ and NOTCH1$^{MUT}$ lines (FIG. 2D).

Example 7—PI3K/mTOR Pathway Inhibition Reduces Tumor Growth in Both Orthotopic Tongue and Subcutaneous Xenograft Models of NOTCH1$^{MUT}$ HNSCC To assess the anti-tumor effect of PI3K/mTOR inhibition in NOTCH1$^{MUT}$ HNSCC, two NOTCH1$^{MUT}$ lines were first used to create subcutaneous xenograft models. The GSK2126458-treated tumors regressed, whereas the vehicle-treated control tumors grew significantly. TUNEL staining showed that, consistent with the in vitro data, tumors treated with GSK2126458 had significant apoptosis (FIGS. 3A and 3B).

An orthotopic xenograft model of HNSCC, whose local growth patterns and histology are similar to those of human HNSCC, was also used (Myers et al., 2002). In both NOTCH1$^{MUT}$ models, GSK2126458 significantly reduced tumor size compared with vehicle alone. TUNEL staining showed that the NOTCH1$^{MUT}$ tumors underwent apoptosis at the end of treatment (FIGS. 3C and 3D).

Figure 4C:
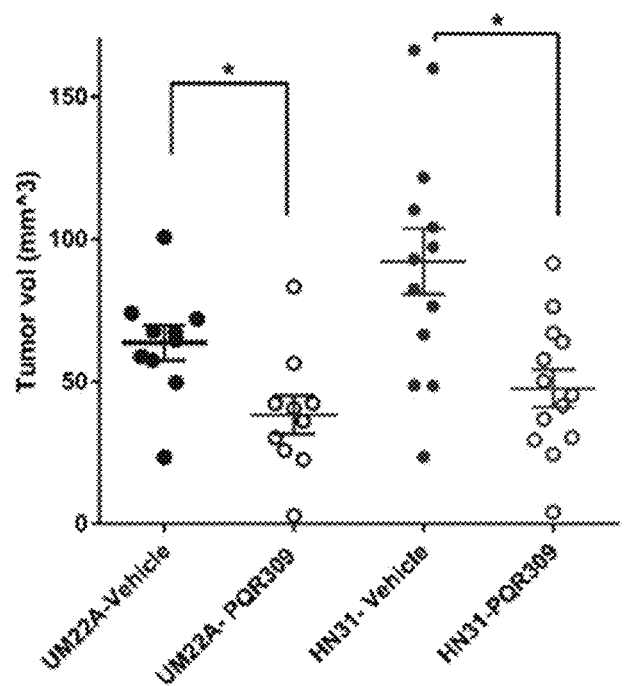
FIG. 4C: HNSCC tumors harboring NOTCH1-LoF mutants are more sensitive to bimiralisib than NOTCH1wt cells in vivo. There was significant reduction of tumor growth (p<0.05) after treatment once daily with bimiralisib (50 mg/kg) in the UM22A and HN31 NOTCH1 inactivating mutant tumors.

Example 8—CRISPR-Cas9 NOTCH1KO Sensitizes NOTCH1$^{WT}$ HNSCC to PI3K/mTOR Pathway Inhibitor-Mediated Apoptosis Four NOTCH1$^{WT}$ lines with NOTCH1 KO were used to test the hypothesis that abrogating NOTCH1 signaling renders NOTCH1$^{WT}$ cells more sensitive to PI3K/mTOR pathway inhibition. Compared with their parental cell lines, the PJ34 and UMSCC49 lines with NOTCH1 KO showed decreased cell viability after GSK2126458 treatment, with IC$_{70}$ values that dropped from 0.1 µM to 0.024 µM and from 1.48 µM to 0.36 µM, respectively (FIG. 4A); had a significantly higher rate of apoptosis when treated with PI3K/mTOR inhibitors (FIGS. 4B and 4C); and formed significantly fewer colonies after PI3K/mTOR inhibition (FIG. 4D). However, NOTCH1 KO did not significantly increase the sensitivity of the NOTCH1$^{WT}$ lines FaDU and MDA686LN to PI3K/mTOR pathway inhibition (FIG. 17).

Figures 18A, 18B:
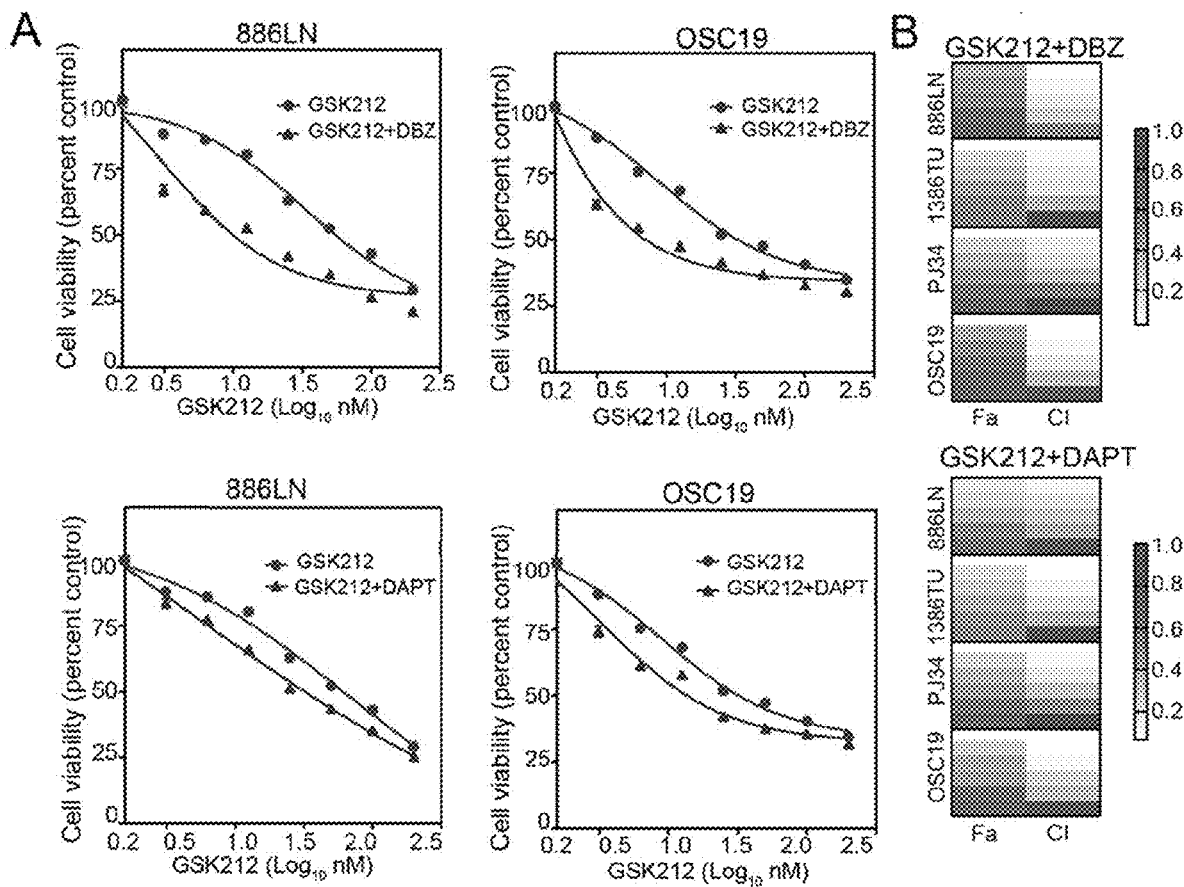
FIGS. 18A-18E: Effects of the combined inhibition of the PI3K/mTOR and NOTCH1 pathways in NOTCH1WT head and neck squamous cell carcinoma (HNSCC).
Figure 18C:
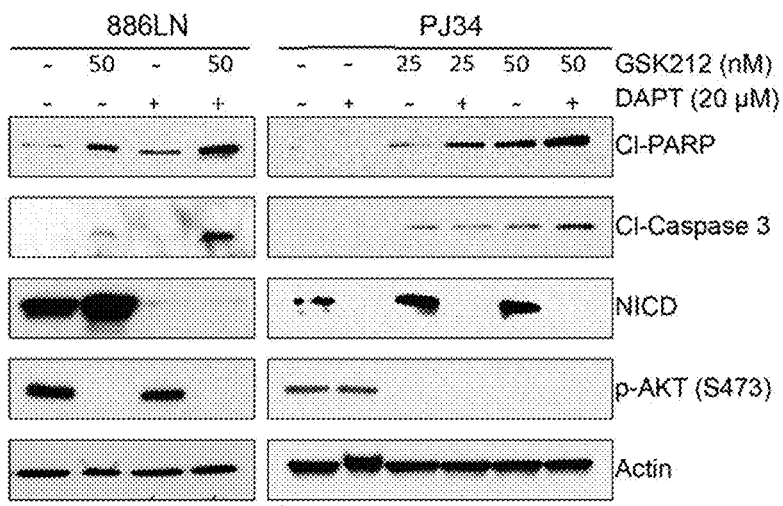
Figure 18D:
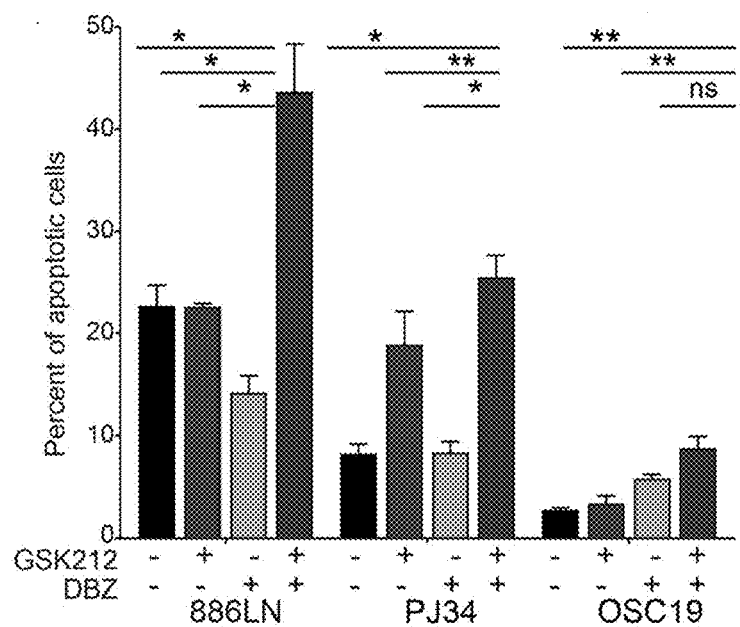
Figure 18E:
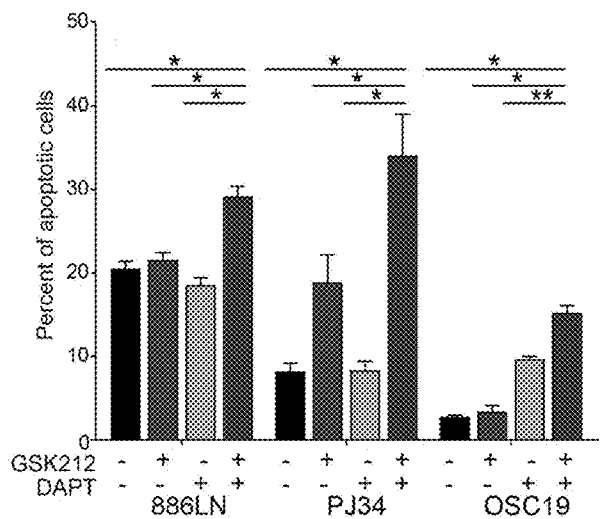

The γ-secretase inhibitors N—[N-(3,5-difluorophenacetyl-L-alanyl)]-S-phenylglycine t-butyl ester and dibenzazepine were also sued to inhibit the intra-membrane proteolytic cleavage/activation of NOTCH1. The combination of PI3K/mTOR and NOTCH1 signaling inhibitors decreased cell viability in four NOTCH1$^{WT}$ lines (FIGS. 18A and 18B), with most combination indices of less than 1 for a range of fractions affected. Consistent with these findings, the combination also increased apoptosis (FIGS. 18C-18E). As with the NOTCH1-KO lines, combined γ-secretase and PI3K/mTOR inhibition was not synergistic in two NOTCH1$^{WT}$ lines, likely because of the diverse molecular mechanisms of resistance.

Figure 19A:
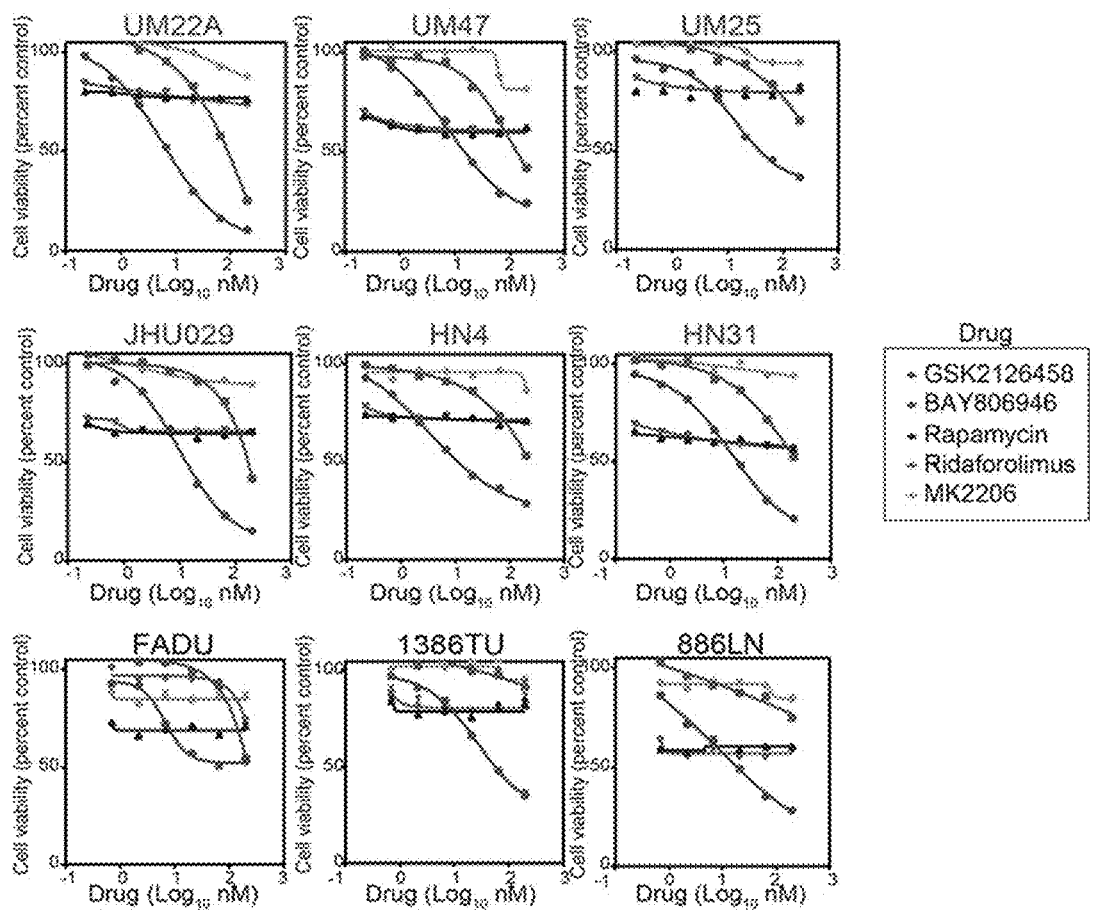
FIGS. 19A-19B: Effect of the inhibition of multiple components of the PI3K/mTOR pathway in head and neck squamous cell carcinoma (HNSCC) cell lines.

Example 9—PDK1 Mediates Resistance to PI3K/mTOR Pathway Inhibition in NOTCH1$^{WT}$ HNSCC To identify the mechanism of sensitivity in NOTCH1$^{MUT}$ HNSCC, components of the PI3K/mTOR pathway were inhibited in both NOTCH1$^{MUT}$ and NOTCH1$^{WT}$ cell lines. All cell lines were resistant to the mTOR inhibitors (rapamycin and ridaforolimus) and the AKT inhibitor (MK-2206), but both the dual PI3K/mTOR inhibitor (GSK2126458) and pan-PI3K inhibitor (BAY806946) had differential effects on NOTCH1$^{MUT}$ and NOTCH1$^{WT}$ cells (FIG. 19A). These results suggest that an important signaling node that is downstream of PI3K but independent of AKT and mTOR is responsible for the differential sensitivity.

Figure 5:
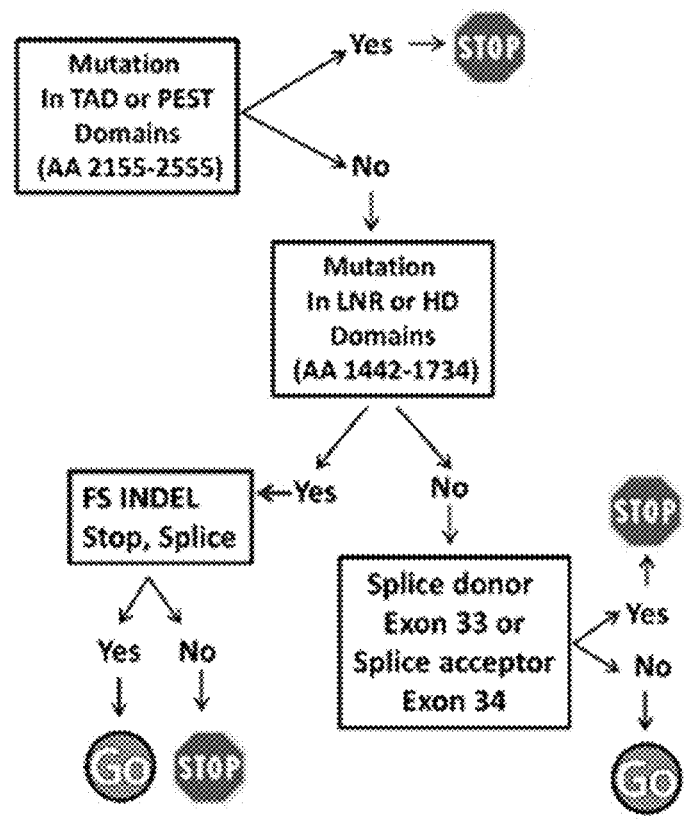
FIG. 5: Flow-diagram for selecting NOTCH1-LoF mutations in accordance with a preferred embodiment of the present invention. Patients with NOTCH1 mutations in regions associated with activation including TAD/PEST domains or mutations in LNR and HD domains that are not truncating are excluded. Splice mutations in Exon 33 or 34 are also excluded, but patients with NOTCH1 mutation in all other regions are eligible.
Figure 19B:
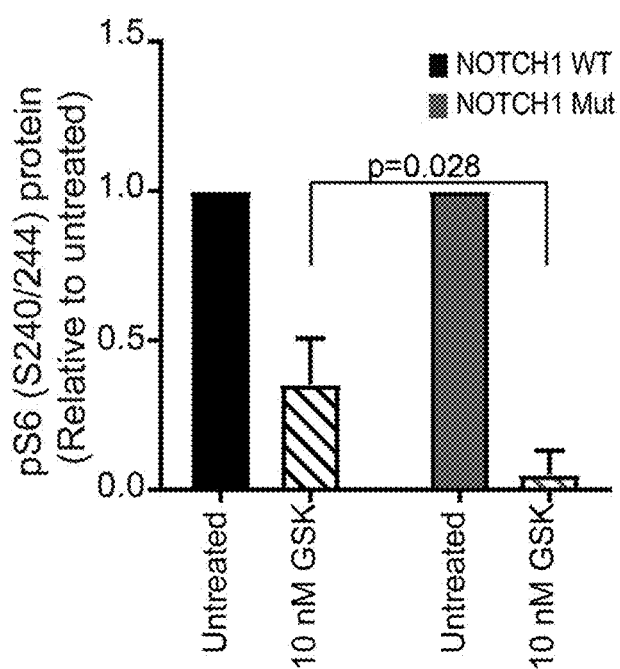
Figure 20A:
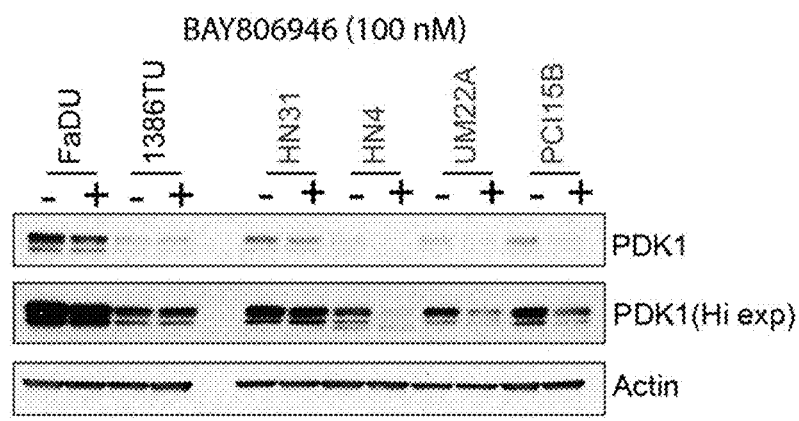
FIGS. 20A-20D: PDK1 inhibition and AKT inhibition act synergistically against NOTCH1MUT head and neck squamous cell carcinoma (HNSCC).
Figure 20B:
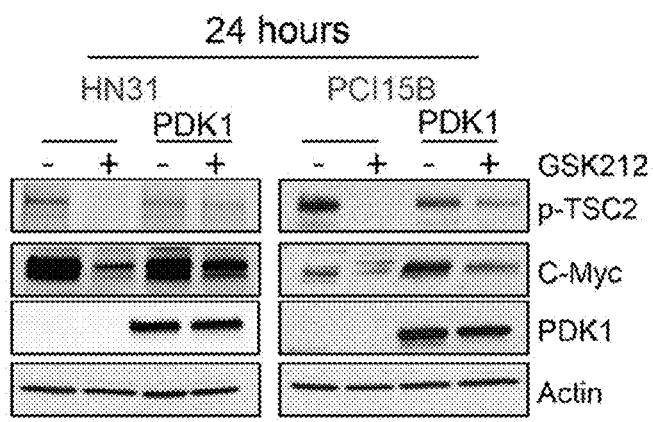

Next, PDK1's role in the differential sensitivity was investigated, because PDK1 is activated by PI3K, mediates resistance to PI3K inhibition in breast cancer (Castel et al., 2016), and can regulate p70S6K, which was inhibited more robustly in NOTCH1$^{MUT}$ than in NOTCH1$^{WT}$ HNSCC (FIG. 19B). PI3K inhibition using three different drugs reduced PDK1 expression in only NOTCH1$^{MUT}$ lines (FIGS. 5A, 5B, and 20A). To assess PDK1's role in PI3K/mTOR inhibition-induced apoptosis in NOTCH1$^{MUT}$ HNSCC, PDK1's overexpression was induced in NOTCH1$^{MUT}$ HNSCC cells. Compared with parental lines, NOTCH1$^{MUT}$ cells overexpressing PDK1 had higher expression levels of p-AKT, p-S6, and p-4EBP1 (FIG. 5C), and they had decreased apoptosis after GSK2126458 treatment (FIGS. 5D and 5E). As expected, PDK1 overexpression did not inhibit the effect of GSK2126458 on phosphatidylinositol (3,4,5)-trisphosphate (PIPS)-dependent molecules such as p-AKT (T308) (FIG. 5E). In contrast, PDK1 overexpression did inhibit the effect of GSK2126458 on PIP$_3$-independent molecules such as c-Myc and p-TSC2 (FIG. 20B).

Figure 6C:
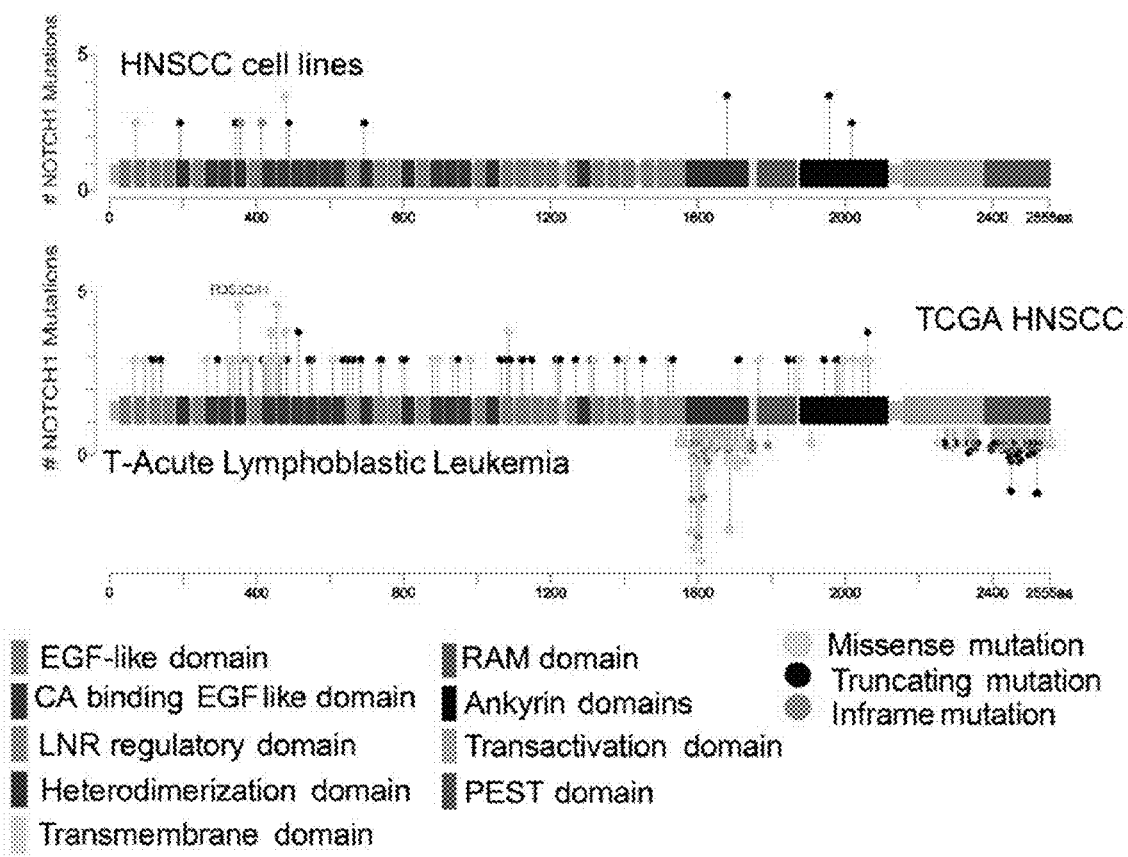
Figure 6D:
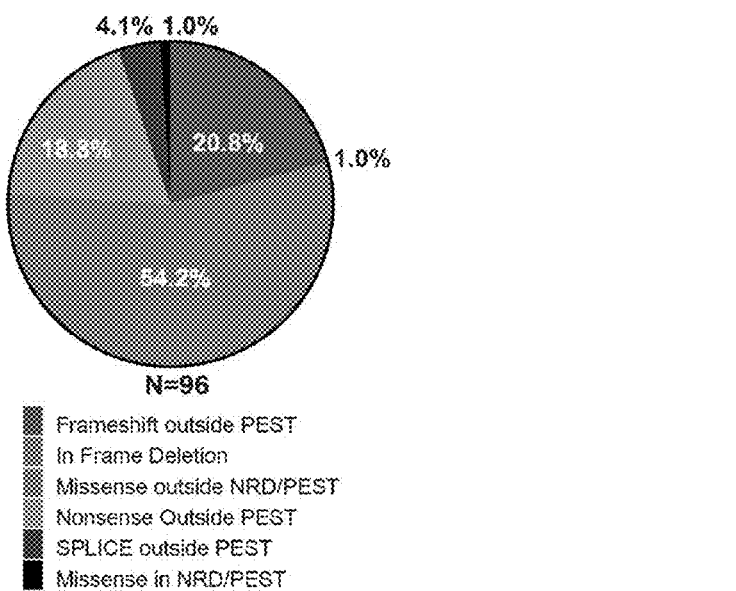
Figure 6F:
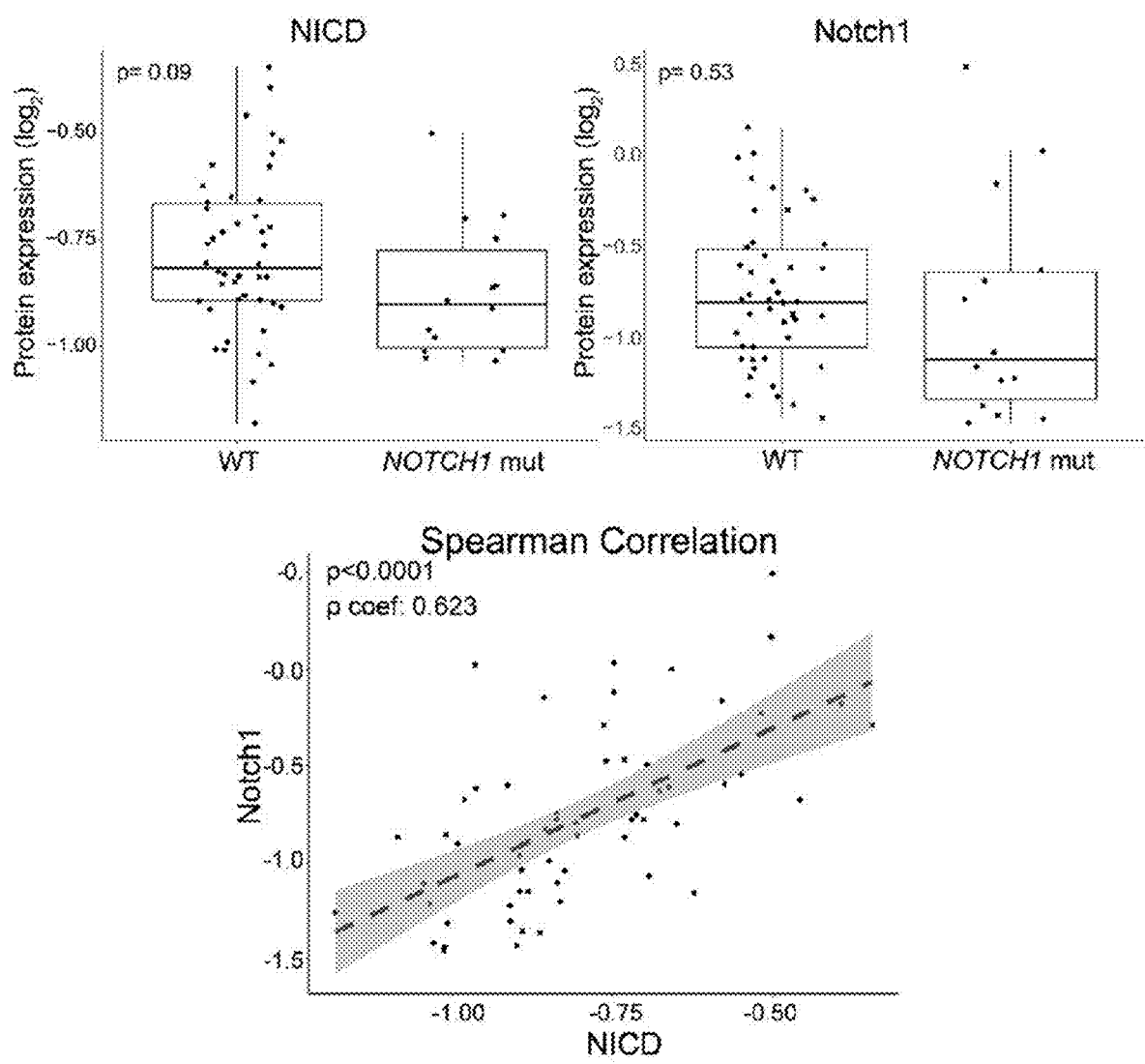
Figure 7A:
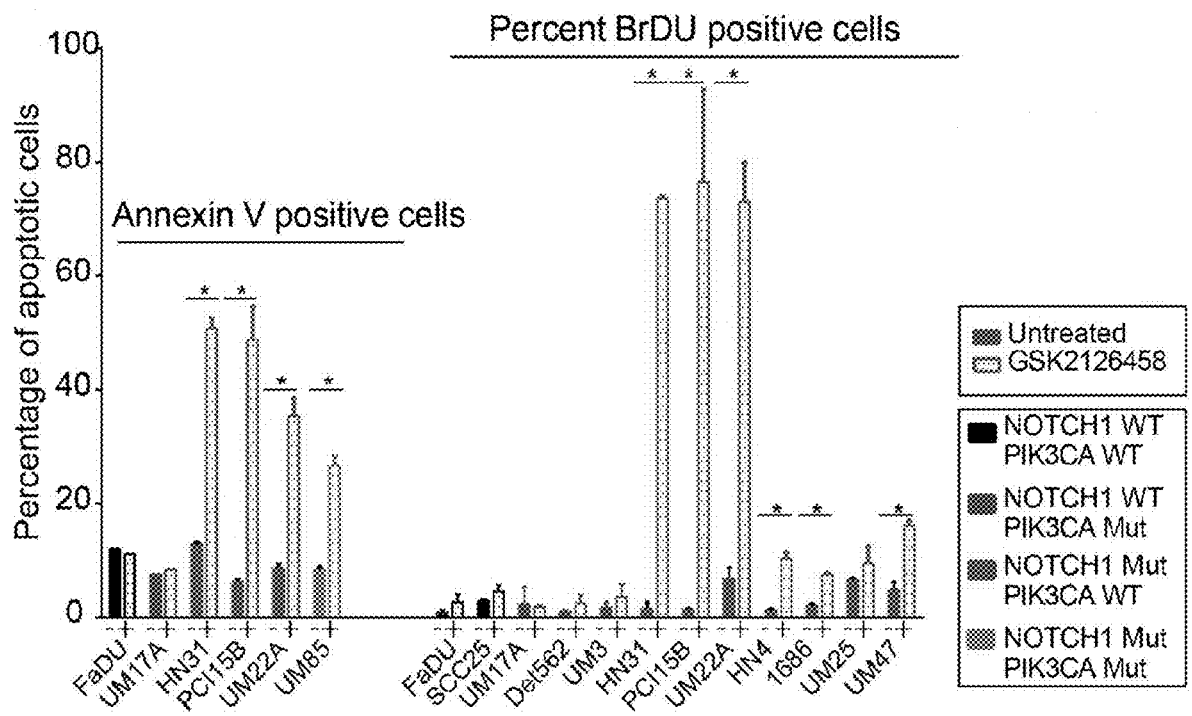
FIGS. 7A-7D: PI3K/mTOR signaling inhibition induces cell death in $NOTCH1^{MUT}$ but not $NOTCH1^{WT}$ head and neck squamous cell carcinoma (HNSCC) cell lines in vitro.
Figure 7B:
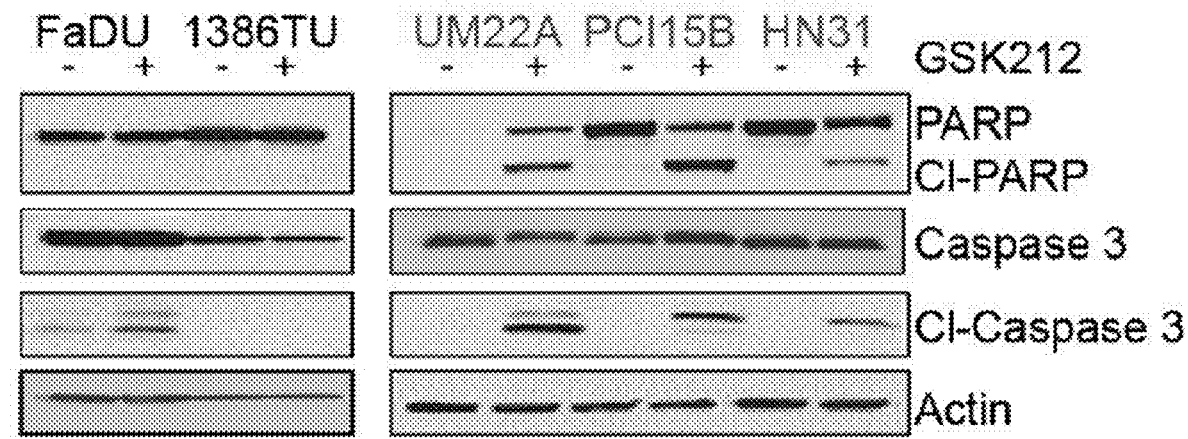
Figure 7C:
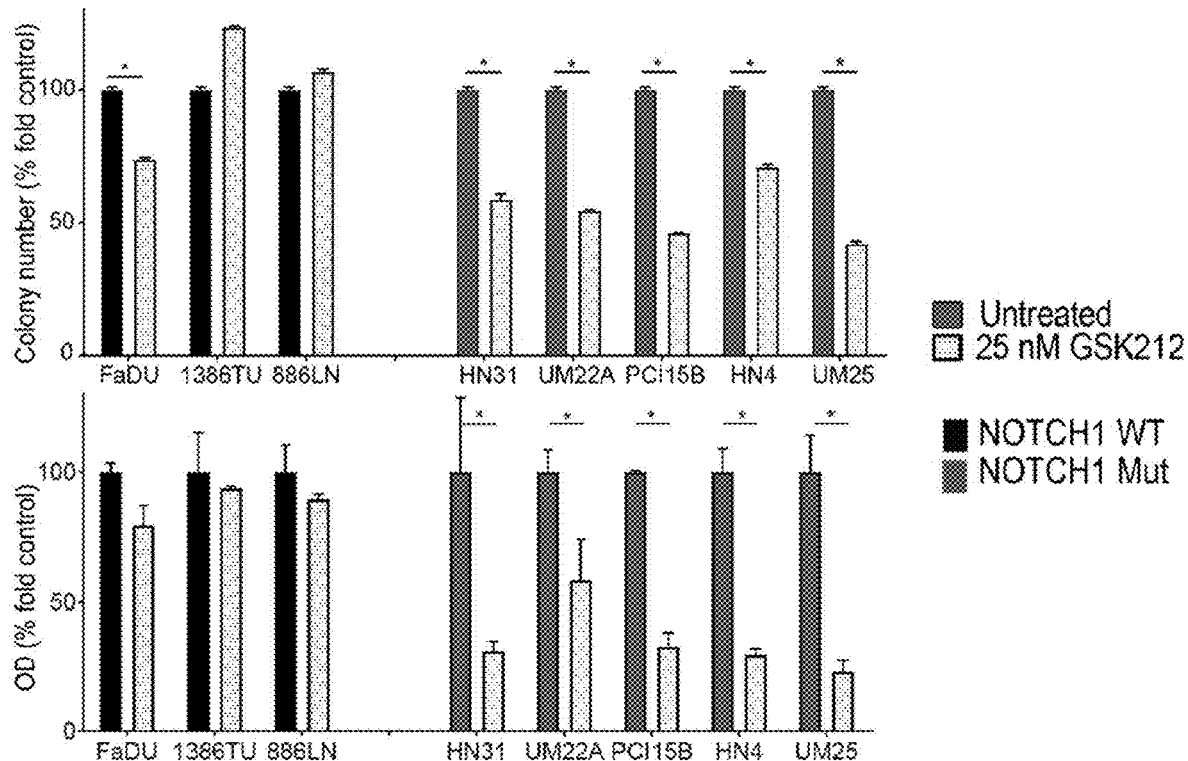
Figure 7D:
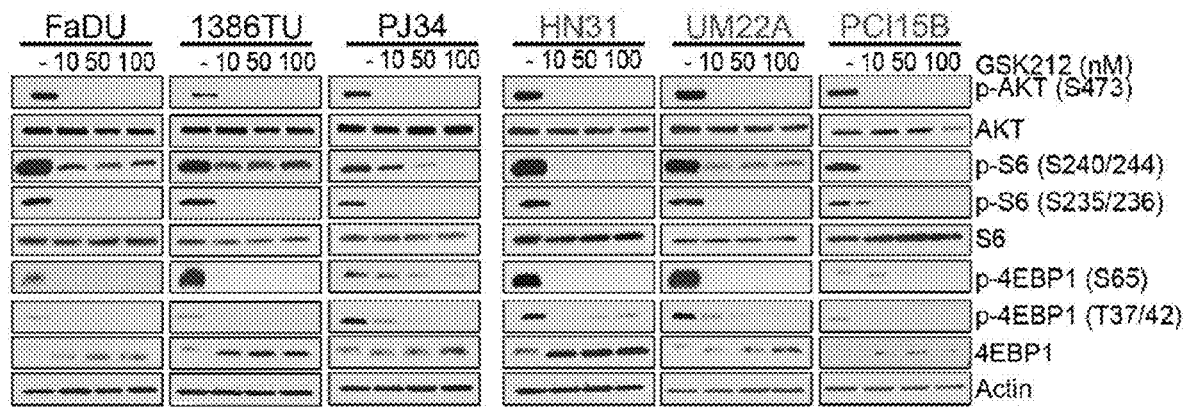
Figure 8A:
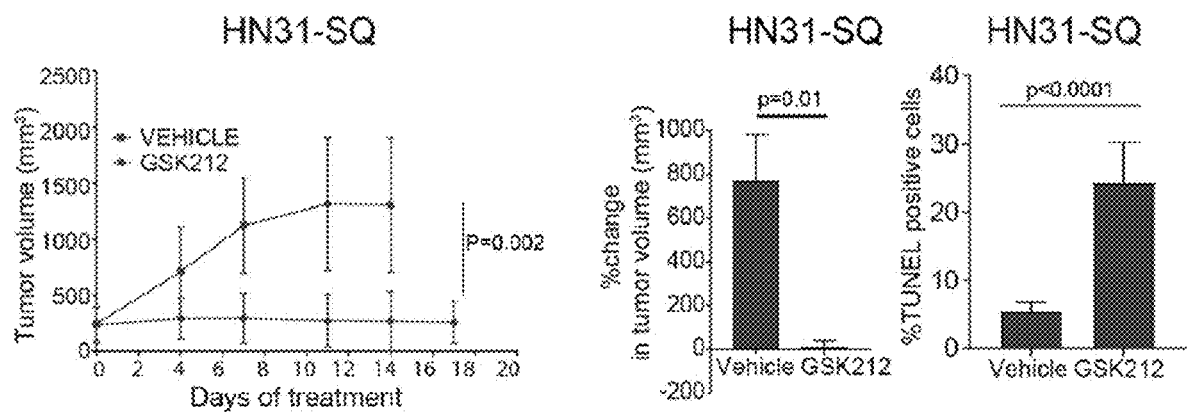
FIGS. 8A-8D: PI3K/mTOR pathway inhibitors cause apoptosis and reduce tumor size in $NOTCH1^{MUT}$ head and neck squamous cell carcinoma (HNSCC) in vivo.
Figure 8B:
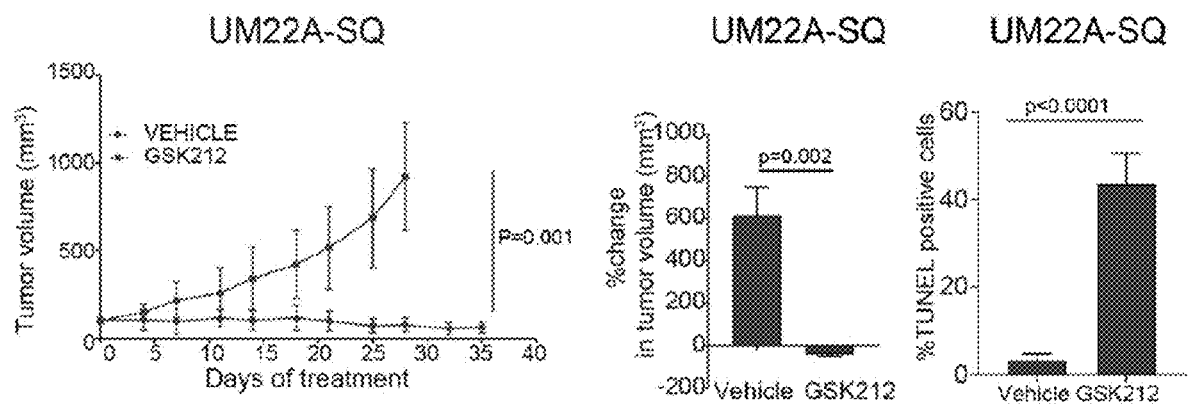
Figure 8C:
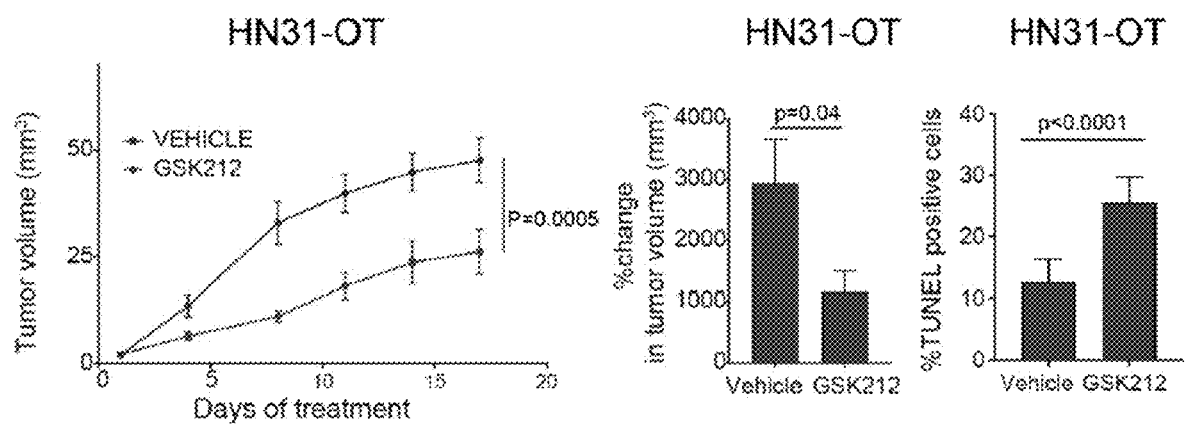
Figure 8D:
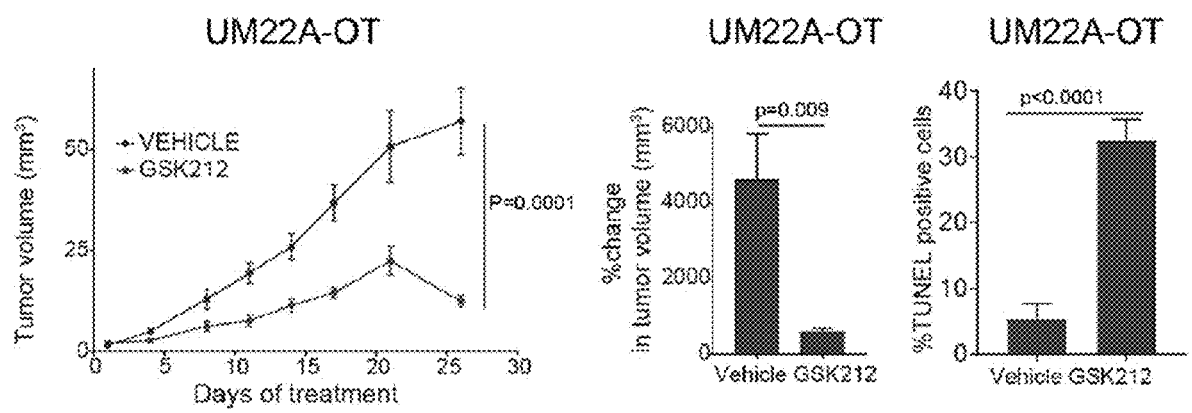
Figure 9A:
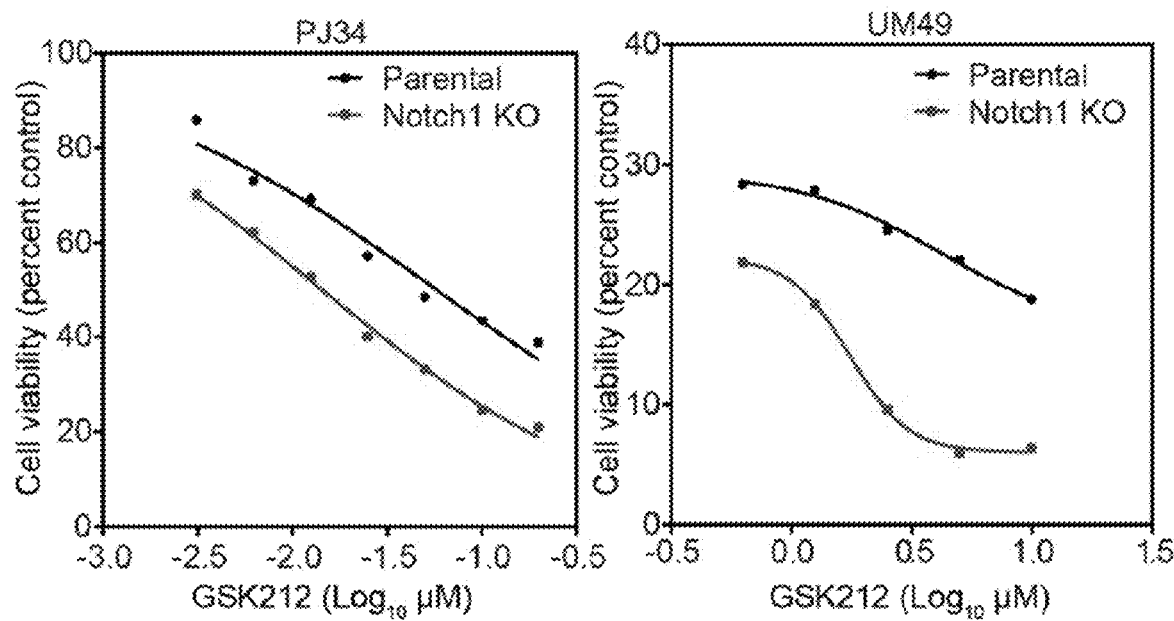
FIGS. 9A-9D: NOTCH1 knockout (KO) sensitizes two $NOTCH1^{WT}$ head and neck squamous cell carcinoma (HNSCC) cell lines to PI3K/mTOR pathway inhibition in vitro. Two $NOTCH1^{WT}$ HNSCC cell lines (PJ34 and UMSCC49 [UM49]), parental cell lines, and NOTCH1 KO cell lines were treated with PI3K/mTOR pathway inhibitors.
Figure 9B:
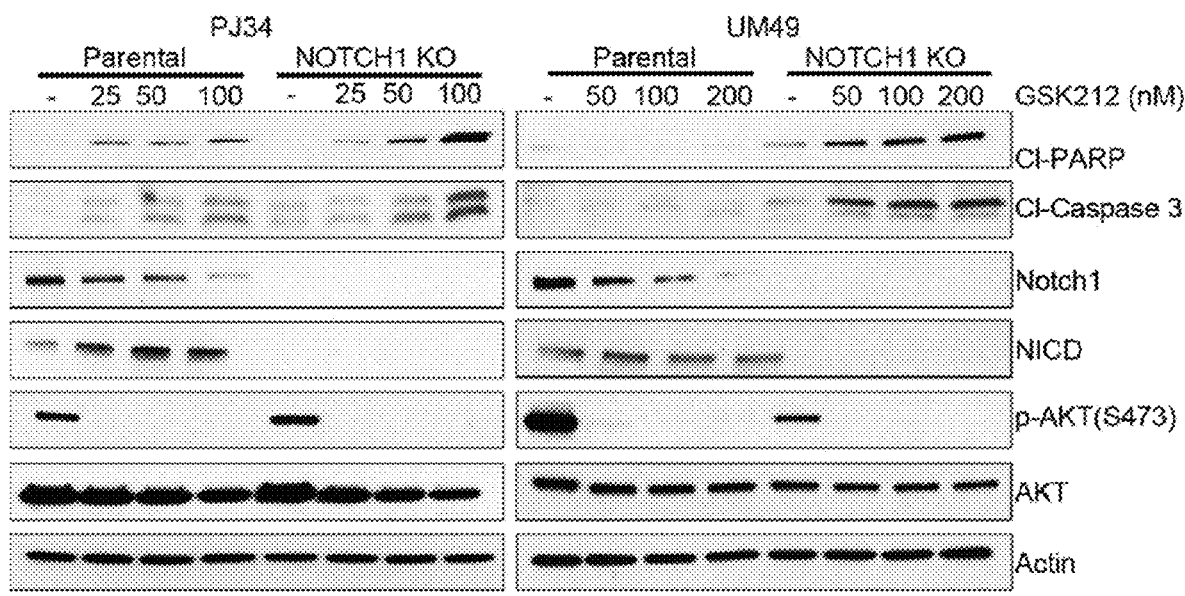
Figure 9C:
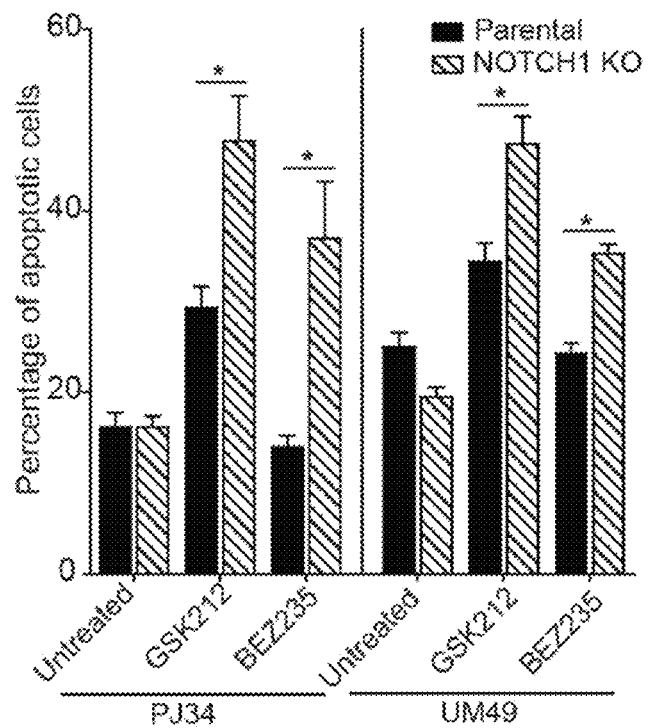
Figure 9D:
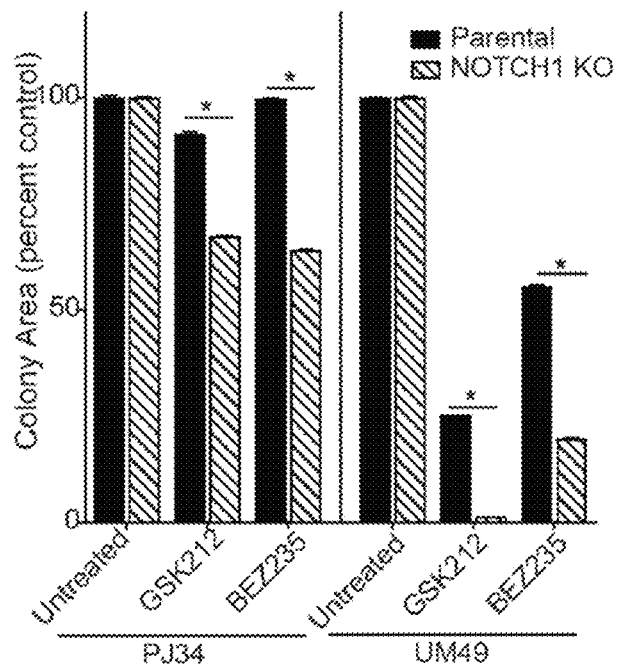
Figure 10A:
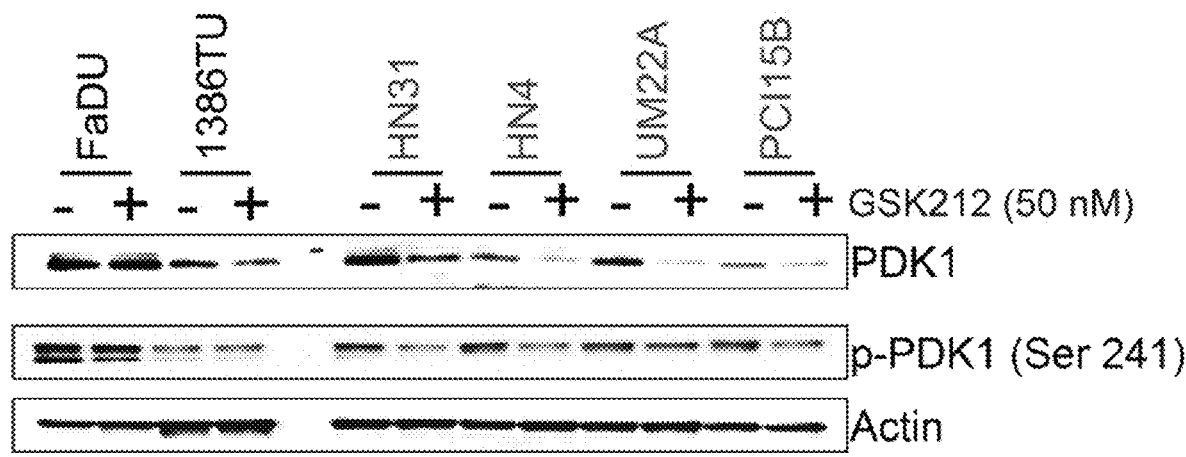
FIGS. 10A-10E: PDK1 mediates resistance to PI3K/mTOR pathway inhibition in NOTCH1$^{WT}$ head and neck squamous cell carcinoma (HNSCC) lines.
Figure 10B:
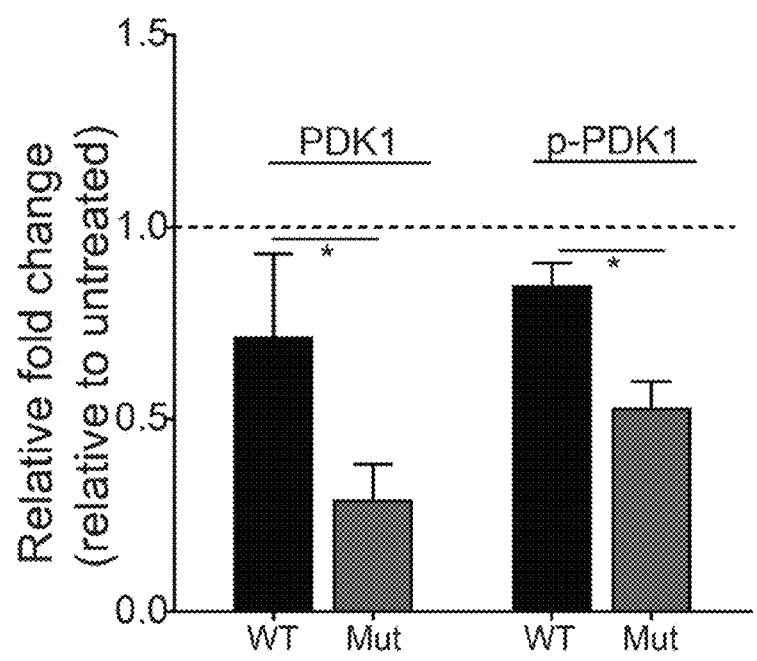
Figure 10C:
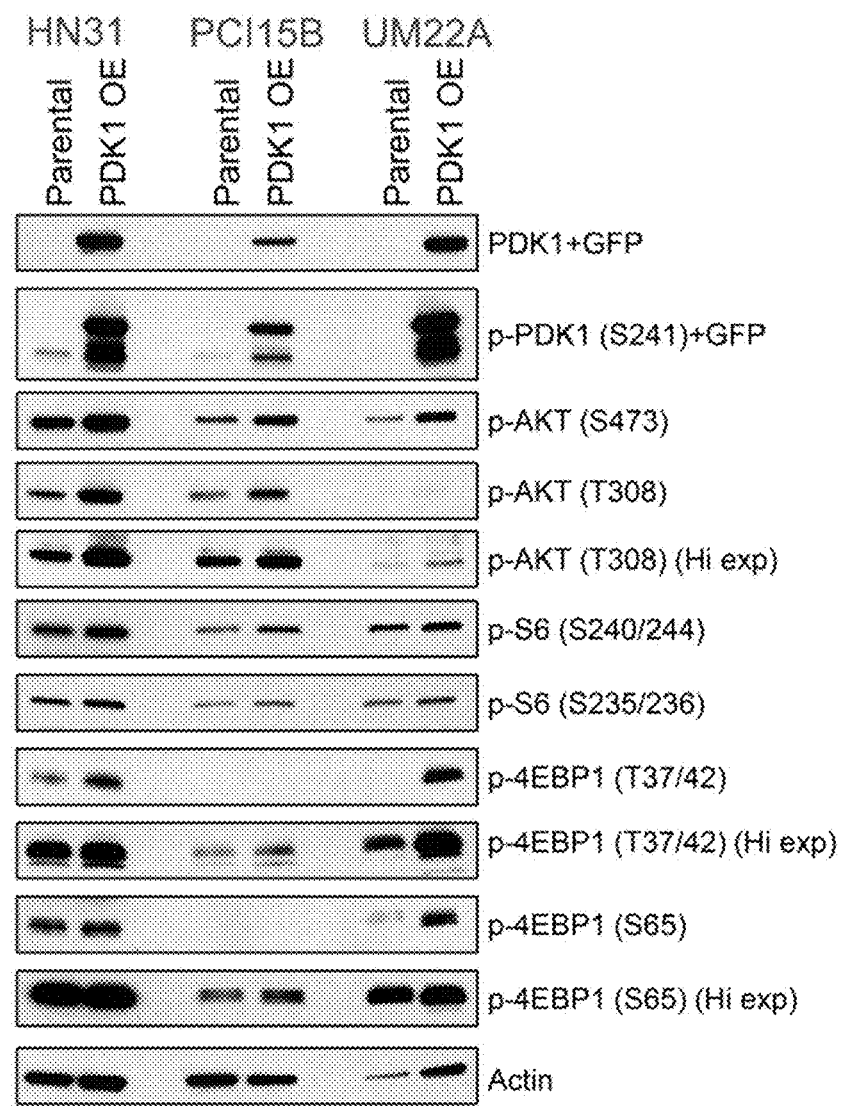
Figure 10D:
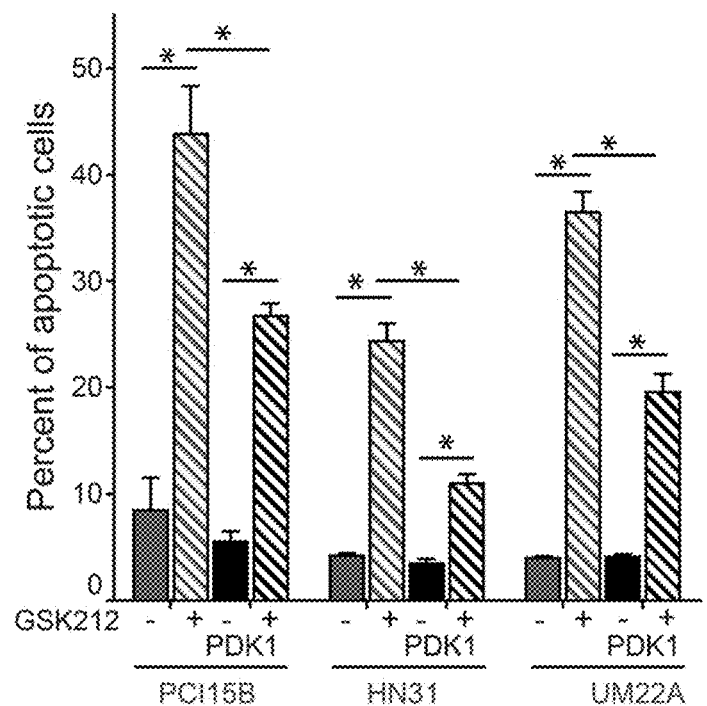
Figure 10E:
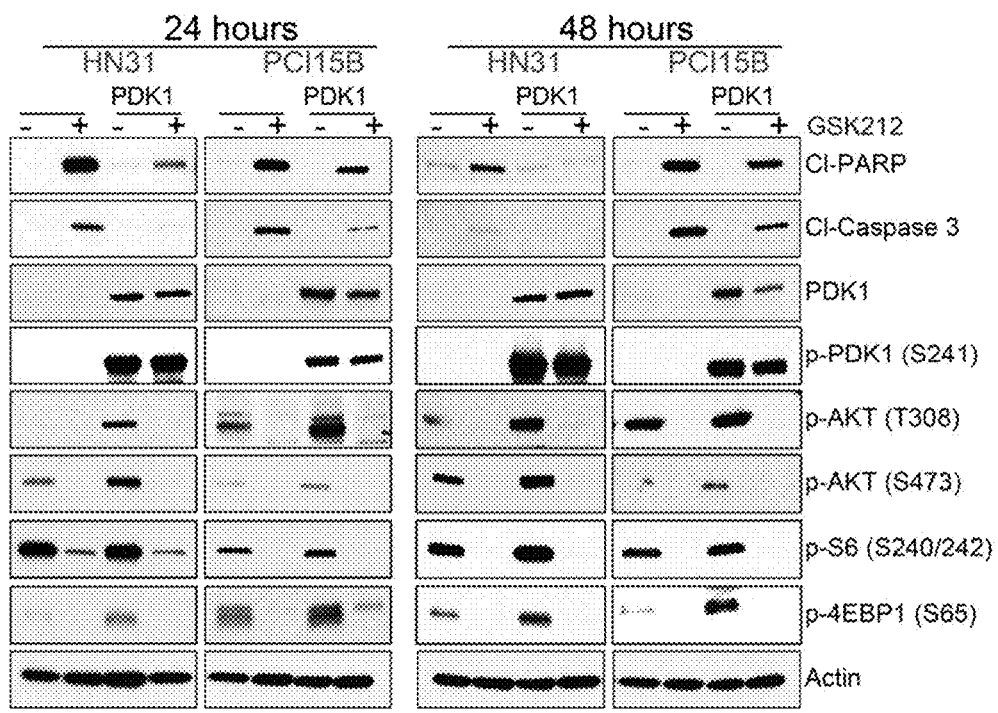
Figure 11A:
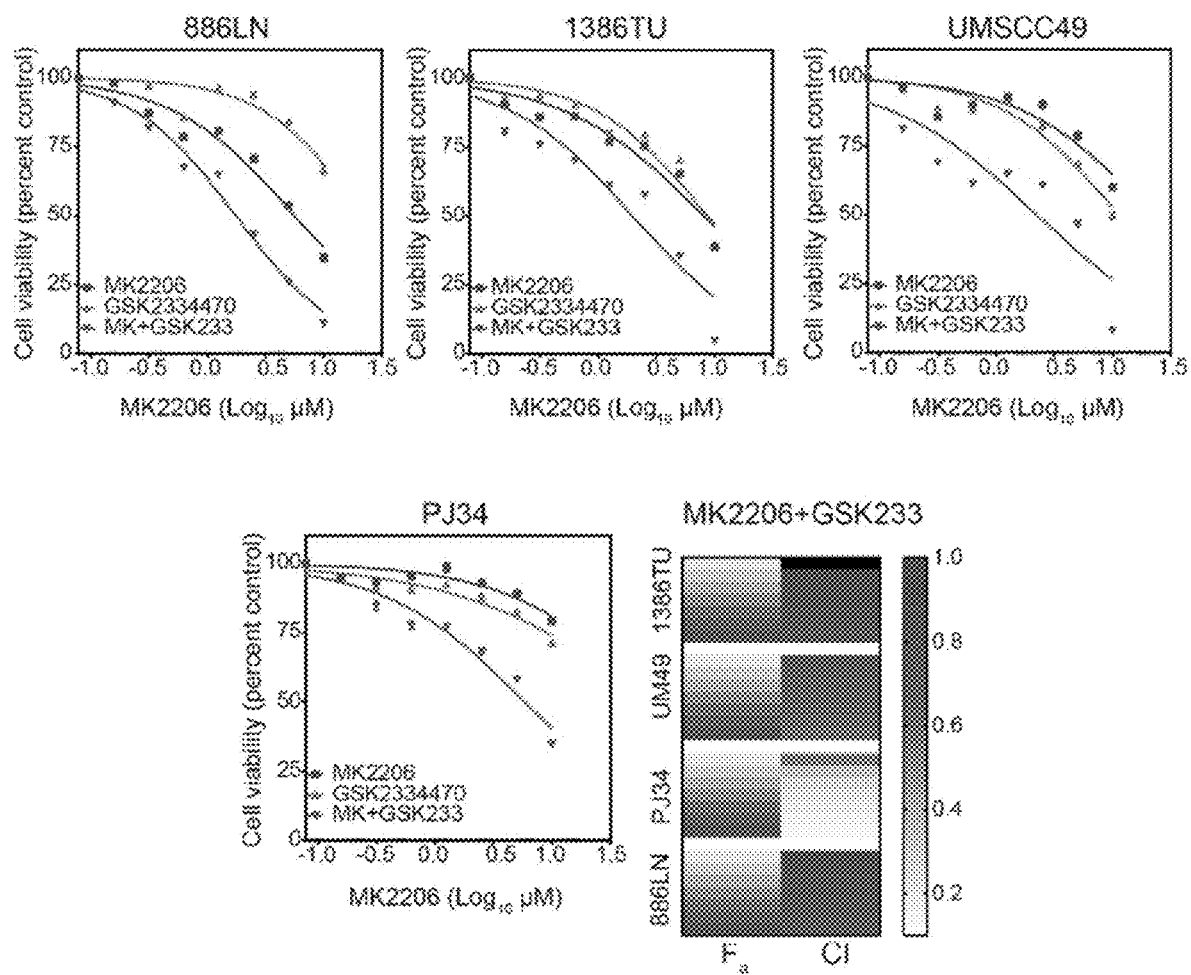
FIGS. 11A-11C: AKT inhibition and PDK1 inhibition synergistically induce apoptosis in NOTCH1$^{WT}$ head and neck squamous cell carcinoma (HNSCC) lines FIG. 11A. NOTCH1$^{WT}$ HNSCC cell lines were treated with increasing concentrations of MK2206, GSK2334470 (GSK233), or the MK2206-GSK233 combination at a fixed 1:1 ratio for 72 hours, and cell viability was measured with the CellTiter-Glo assay. The combination index (CI) values were calculated with CalcuSyn, and the fraction affected ($F_a$) and CI are plotted as heatmaps for all four cell lines.
Figure 11B:
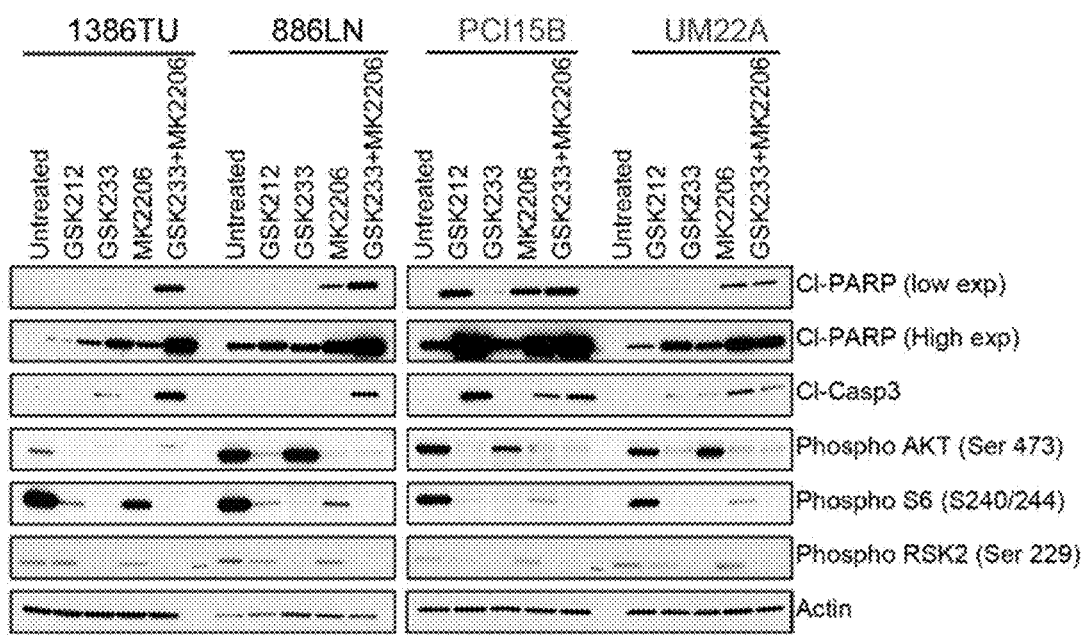
Figure 11C:
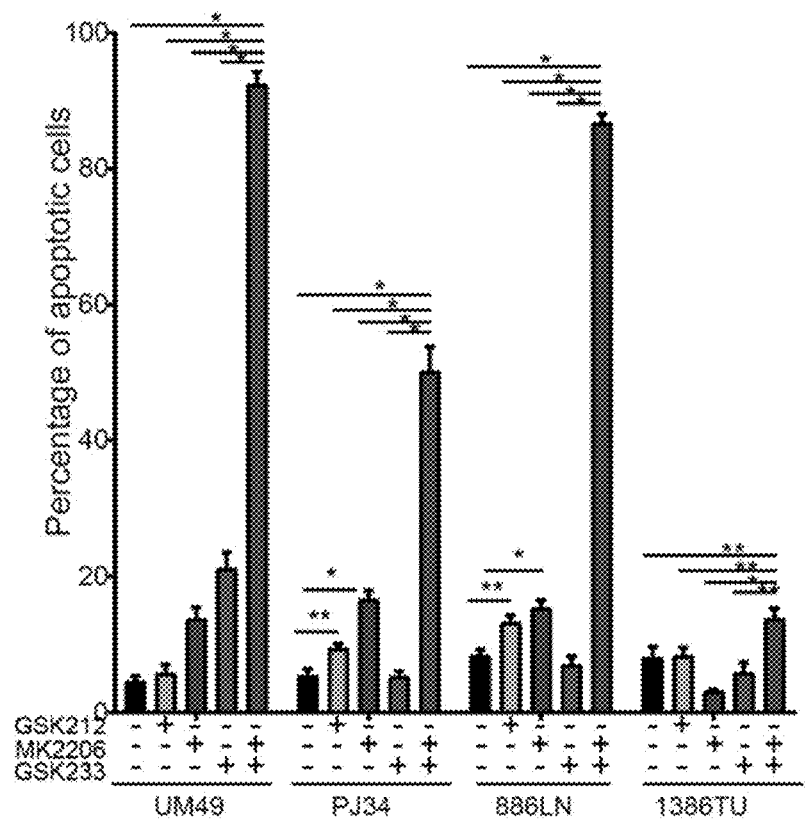
Figure 20C:
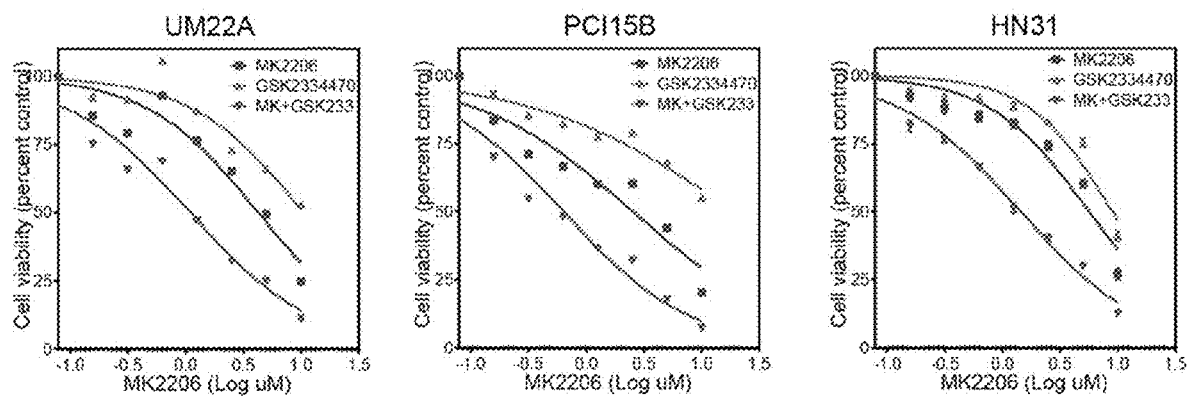
Figure 20D:
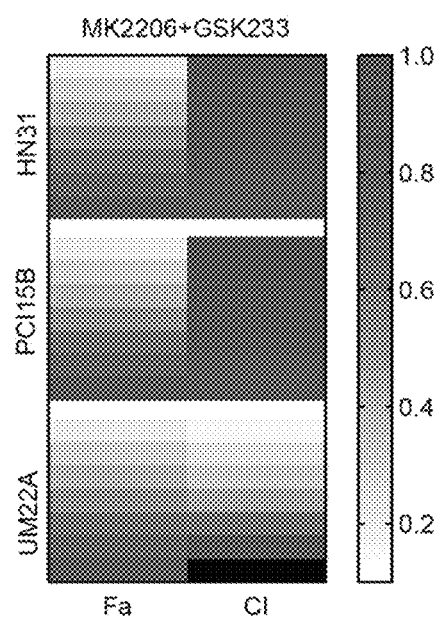

PDK1 inhibition with GSK2334470 alone had little effect on cell viability or apoptosis regardless of NOTCH1 status (FIGS. 6A-6C). Therefore, it was hypothesized that both AKT and PDK1 inhibition are necessary for apoptosis following PI3K inhibition. In all cell lines tested, AKT inhibition plus PDK1 inhibition decreased cell viability with combination indices consistent with a greater-than-additive effect (FIGS. 6A, 20C, and 20D). The combination also led to apoptosis in all cell lines tested (FIGS. 6B and 6C). In NOTCH1$^{MUT}$ lines, the effect of the combination was similar to that achieved with PI3K/mTOR inhibition alone (FIG. 6B).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abad et al., "Notch Inhibition Enhances Cardiac Reprogramming by Increasing MEF2C Transcriptional Activity," *Stem Cell Reports*, 8:548-560, 2017.

Agrawal et al., "Exome sequencing of head and neck squamous cell carcinoma reveals inactivating mutations in NOTCH1," *Science*, 333:1154-1157, 2011.

Agrawal et al., "Comparative genomic analysis of esophageal adenocarcinoma and squamous cell carcinoma," *Cancer Discovery*, 2(:899-905, 2012.

Akbani et al., "A pan-cancer proteomic perspective on The Cancer Genome Atlas," *Nat. Comm.*, 5: 3887, 2014.

Beaufils et al., "5-(4,6-Dimorpholino-1,3,5-triazin-2-yl)-4-(trifluoromethyl)pyridin-2-amine (PQR309), a Potent, Brain-Penetrant, Orally Bioavailable, Pan-Class I PI3K/mTOR Inhibitor as Clinical Candidate in Oncology," *Journal of Medicinal Chemistry*, 60:7524-7538, 2017.

Bendell et al., "Phase I, dose-escalation study of BKM120, an oral pan-Class I PI3K inhibitor, in patients with advanced solid tumors," *J. Clin. Oncol.*, 30:282-90, 2012.

Bendell et al., "A phase 1 study of the sachet formulation of the oral dual PI3K/mTOR inhibitor BEZ235 given twice daily (BID) in patients with advanced solid tumors," *Invest. New Drugs*, 33:463-471, 2015.

Bohnacker et al., "Deconvolution of Buparlisib's mechanism of action defines specific PI3K and tubulin inhibitors for therapeutic intervention," *Nat Comm.*, 8:14683, 2017.

Bornkamp et al., "Response-adaptive dose-finding under model uncertainty," *Ann. Appl. Stat.*, 5:1611-1631, 2011.

Byers et al., "An Epithelial-Mesenchymal Transition Gene Signature Predicts Resistance to EGFR and PI3K Inhibitors and Identifies Axl as a Therapeutic Target for Overcoming EGFR Inhibitor Resistance," *Clin. Cancer Res.*, 19:279-290, 2013.

Byers et al., "Proteomic profiling identifies dysregulated pathways in small cell lung cancer and novel therapeutic targets including PARP1," *Cancer Discov.*, 2:798-811, 2012.

Cai et al., "Dysregulations in the PI3K pathway and targeted therapies for head and neck squamous cell carcinoma," *Oncotarget*, 8:22203-22217, 2017.

Cancer Genome Atlas, "Comprehensive genomic characterization of head and neck squamous cell carcinomas," *Nature*, 517:576-582, 2015.

Castel et al., "PDK1-SGK1 Signaling Sustains AKT-Independent mTORC1 Activation and Confers Resistance to PI3Kalpha Inhibition," *Cancer Cell*, 30:229-242, 2016.

Cerami et al., "The cBio Cancer Genomics Portal: An Open Platform for Exploring Multidimensional Cancer Genomics Data," *Cancer Discovery*, 2:401-404, 2012.

Chandarlapaty et al., "AKT inhibition relieves feedback suppression of receptor tyrosine kinase expression and activity," *Cancer Cell*, 19:58-71, 2011.

Chiang M Y, Radojcic V, Maillard I. Oncogenic Notch signaling in T-cell and B-cell lymphoproliferative disorders. Current opinion in hematology 2016; 23: 362-370.

Courtney et al., "The PI3K pathway as drug target in human cancer," *J. Clin. Oncol.*, 28:1075-1083, 2010.

De Buck et al., "Population pharmacokinetics and pharmacodynamics of BYL719, a phosphoinositide 3-kinase antagonist, in adult patients with advanced solid malignancies," *Br. J. Clin. Pharmacol.*, 78:543-555, 2014.

Di Nicolantonio et al., "Deregulation of the PI3K and KRAS signaling pathways in human cancer cells determines their response to everolimus," *J. Clin. Invest.*, 120:2858-2866, 2010.

Di-Poi et al., "Antiapoptotic role of PPARbeta in keratinocytes via transcriptional control of the Akt1 signaling pathway," *Mol. Cell*, 10:721-733, 2002.

D'Souza et al., "The many facets of Notch ligands," *Oncogene*, 27:5148-5167, 2008.

Elkabets et al., "AXL mediates resistance to PI3Kalpha inhibition by activating the EGFR/PKC/mTOR axis in head and neck and esophageal squamous cell carcinomas," *Cancer Cell*, 27:533-546, 2015.

Ferlay et al., "Cancer incidence and mortality worldwide: Sources, methods and major patterns in GLOBOCAN 2012," *International Journal of Cancer*, 136:E359-E386, 2015.

Ferrando, "The role of NOTCH1 signaling in T-ALL," *Hematology Am. Soc. Hematol. Educ. Program*, 2009:353-361, 2009.

Ferrarotto et al., "Epithelial-Mesenchymal Transition Predicts Polo-Like Kinase 1 Inhibitor-Mediated Apoptosis in Non-Small Cell Lung Cancer," *Clin. Cancer Res.*, 22:1674-1686, 2016.

Ferrarotto et al., "Activating NOTCH1 mutations define a distinct subgroup of adenoid cystic carcinoma patients with poor prognosis, propensity to bone and liver metastasis, and potential responsiveness to Notch1 inhibitors," *J. Clin. Oncol.*, 35:352-360, 2017.

Ferrarotto R, Ho A L, Wirth L J, Dekel E, Walker R W, Vergara-Silva A L. ACCURACY: phase (P) 2 trial of AL101, a pan-Notch inhibitor, in patients (pts) with recurrent/metastatic (R/M) adenoid cystic carcinoma (ACC) with Notch activating mutations (Notchact mut). Journal of Clinical Oncology 2019; 37: TPS6098-TPS6098.

Fruman et al., "The PI3K Pathway in Human Disease," *Cell*, 170:605-635, 2017.

Fruman & Rommel, "PI3K and cancer: lessons, challenges and opportunities," *Nat. Rev. Drug Discov.*, 13:140-156, 2014.

Habets R A, de Bock C E, Serneels L, Lodewijckx I, Verbeke D, Nittner D et al. Safe targeting of T cell acute lymphoblastic leukemia by pathology-specific NOTCH inhibition. Science Translational Medicine 2019; 11: eaau6246.

Hales et al., "New insights into Notch1 regulation of the PI3K-AKT-mTOR1 signaling axis: targeted therapy of gamma-secretase inhibitor resistant T-cell acute lymphoblastic leukemia," *Cell Signal.*, 26:149-161, 2014.

Herzog et al., "PI3K/mTOR inhibitor PF-04691502 antitumor activity is enhanced with induction of wild-type TP53 in human xenograft and murine knockout models of head and neck cancer," *Clin. Cancer Res.*, 19:3808-3819, 2013.

Ho et al., "The Mutational Landscape of Adenoid Cystic Carcinoma," *Nature Genetics*, 45:791-798, 2013.

Iglesias-Bartolome et al., "Exploiting the Head and Neck Cancer Oncogenome: Widespread PI3K-mTOR Pathway Alterations and Novel Molecular Targets," *Cancer Discov.*, 3:722-725, 2013.

Janku et al., "PIK3CA Mutations in Patients with Advanced Cancers Treated with PI3K/AKT/mTOR Axis Inhibitors," *Molecular Cancer Therapeutics*, 10:558-565, 2011

Janku et al., "PI3K/AKT/mTOR inhibitors in patients with breast and gynecologic malignancies harboring PIK3CA mutations," *J. Clin. Oncol.*, 30:777-782, 2012.

Jimeno et al., "A randomized, phase 2 trial of docetaxel with or without PX-866, an irreversible oral phosphatidylinositol 3-kinase inhibitor, in patients with relapsed or metastatic head and neck squamous cell cancer," *Oral Oncol.*, 51:383-388, 2015.

Johnson et al., "Abstract 393: NOTCH1 inactivating mutation mediates sensitivity to PI3K/mTOR inhibitors in head and neck squamous cell carcinoma," *Cancer Research*, 76(14 Supplement):393-393, 2016.

Juric et al., "Convergent loss of PTEN leads to clinical resistance to a PI(3)Kalpha inhibitor," *Nature*, 518:240-244, 2015.

Kalu et al., "Genomic characterization of human papillomavirus-positive and -negative human squamous cell cancer cell lines," *Oncotarget*, 8:86369-86383, 2017.

Kalu et al., "Comprehensive pharmacogenomic profiling of human papillomavirus-positive and -negative squamous cell carcinoma identifies sensitivity to aurora kinase inhibition in KMT2D mutants," *Cancer Lett.*, 431:64-72, 2018.

Kelly et al., "Notch-induced T cell development requires phosphoinositide-dependent kinase 1," *EMBO J.*, 26:3441-3450, 2007.

Keysar et al., "A patient tumor transplant model of squamous cell cancer identifies PI3K inhibitors as candidate therapeutics in defined molecular bins," *Mol. Oncol.*, 7:776-790, 2013.

Kluk et al., "Gauging NOTCH1 Activation in Cancer Using Immunohistochemistry," *PLoS One*, 8(6):e67306, 2013.

Lee et al., "Vital roles of mTOR complex 2 in Notch-driven thymocyte differentiation and leukemia," *J. Exp. Med.*, 209:713-728, 2012.

Li et al., "Genomic analysis of head and neck squamous cell carcinoma cell lines and human tumors: a rational approach to preclinical model selection," *Mol. Cancer Res.,* 12:571-582, 2014.

Lui et al., "Frequent mutation of the PI3K pathway in head and neck cancer defines predictive biomarkers," *Cancer Discov.,* 3:761-769, 2013.

Liu et al., "BAY 80-6946 is a highly selective intravenous PI3K inhibitor with potent p110alpha and p110delta activities in tumor cell lines and xenograft models," *Mol. Cancer Ther.,* 12:2319-2330, 2013.

Liu et al., "LGR5 promotes epithelial ovarian cancer proliferation, metastasis, and epithelial-mesenchymal transition through the Notch1 signaling pathway," *Cancer Med.,* 7:3132-3142, 2018.

Maira, "PI3K inhibitors for cancer treatment: five years of preclinical and clinical research after BEZ235," *Mol. Cancer Ther.,* 10:2016, 2011.

Mao, "NOTCH Mutations: Multiple Faces in Human Malignancies," *Cancer Prevention Research,* 8:259-261, 2015.

Maxwell et al., "Practical guide for the comparison of two next-generation sequencing systems for solid tumour analysis in a universal healthcare system," *J Clin. Pathol.,* 72:225-231, 2019.

Mazumdar et al., "A Comprehensive Evaluation of Biomarkers Predictive of Response to PI3K Inhibitors and of Resistance Mechanisms in Head and Neck Squamous Cell Carcinoma," *Mol. Cancer Ther.,* 13:2738-2750, 2014.

Mohan et al., "MEK Inhibitor PD-0325901 Overcomes Resistance to PI3K/mTOR Inhibitor PF-5212384 and Potentiates Antitumor Effects in Human Head and Neck Squamous Cell Carcinoma," *Clin. Cancer Res.,* 21:3946-3956, 2015.

Muellner et al., "A chemical-genetic screen reveals a mechanism of resistance to PI3K inhibitors in cancer," *Nat. Chem. Biol.,* 7:787-793, 2011.

Munster et al., "First-in-Human Phase I Study of GSK2126458, an Oral Pan-Class I Phosphatidylinositol-3-Kinase Inhibitor, in Patients with Advanced Solid Tumor Malignancies," *Clin. Cancer Res.,* 22:1932-1939, 2016.

Myers et al., "An orthotopic nude mouse model of oral tongue squamous cell carcinoma," *Clin. Cancer Res.,* 8:293-298, 2002.

Nowell & Radtke, "Notch as a tumour suppressor," *Nat. Rev. Cancer.,* 17:145-159, 2017.

Pickering et al., "Integrative genomic characterization of oral squamous cell carcinoma identifies frequent somatic drivers," *Cancer Discov.,* 3:770-781, 2013.

Pickering et al., "Mutational landscape of aggressive cutaneous squamous cell carcinoma," *Clin. Cancer Research,* 20:6582-6592, 2014.

Pounds & Morris, "Estimating the occurrence of false positives and false negatives in microarray studies by approximating and partitioning the empirical distribution of p-values," *Bioinformatics,* 19:1236-1242, 2003.

Rettig et al., "Cleaved NOTCH1 expression pattern in head and neck squamous cell carcinoma is associated with NOTCH1 mutation, HPV status and high-risk features," *Cancer Prevention Research,* 8:287-295, 2015.

Ritz & Streibig, "Bioassay Analysis Using R," *Journal of Statistical Software;* 12:5, 2005. Rodon et al., "Development of PI3K inhibitors: lessons learned from early clinical trials," *Nat. Rev. Clin. Oncol.,* 10:143-153, 2013.

Rodon & Tabernero, "Improving the Armamentarium of PI3K Inhibitors with Isoform-Selective Agents: A New Light in the Darkness," *Cancer Discov.,* 7:666-669, 2017.

Salphati et al., "Preclinical assessment of the absorption and disposition of the phosphatidylinositol 3-kinase/mammalian target of rapamycin inhibitor GDC-0980 and prediction of its pharmacokinetics and efficacy in human," *Drug Metab. Dispos.,* 40:1785-1796, 2012.

Sambandam et al., "Abstract 2992: Identification of NOTCH1 inactivating mutation as a therapeutic vulnerability to PI3K/mTOR pathway inhibition in head and neck squamous cell carcinoma (HNSCC)," *Cancer Research,* 77(13 Supplement):2992-2992, 2017.

Song et al., "Notch1 deficiency decreases hepatic lipid accumulation by induction of fatty acid oxidation," *Scientific Reports,* 6:19377, 2016.

Soria et al., "Osimertinib in Untreated EGFR-Mutated Advanced Non-Small-Cell Lung Cancer," *N. Engl. J. Med.,* 378:113-125, 2018.

Stransky et al., "The mutational landscape of head and neck squamous cell carcinoma," *Science,* 333:1157-1160, 2011.

Tutt et al., "Oral poly(ADP-ribose) polymerase inhibitor olaparib in patients with BRCA1 or BRCA2 mutations and advanced breast cancer: a proof-of-concept trial," *Lancet,* 376:235-244, 2010.

Venkatesh et al., "Targeting Notch signalling pathway of cancer stem cells," *Stem Cell Investig.,* 5:5, 2018.

Wang et al., "mTOR co-targeting in cetuximab resistance in head and neck cancers harboring PIK3CA and RAS mutations," *J. Natl. Cancer Inst.,* 106(9):dju215, 2014.

Wang et al., "mTOR co-targeting strategies for head and neck cancer therapy," *Cancer Metastasis Rev.,* 36:491-502, 2017.

Wicki et al., "First-in human, phase1, dose-escalation pharmacokinetic and pharmacodynamic study of the oral dual PI3K and mTORC1/2 inhibitor PQR309 in patients with advanced solid tumors (SAKK 67/13)," *European Journal of Cancer,* 96:6-16, 2018.

Wu et al., "COL11A1 confers chemoresistance on ovarian cancer cells through the activation of Akt/c/EBPbeta pathway and PDK1 stabilization," *Oncotarget,* 6:23748-23763, 2015.

Yamaguchi et al., "A synthetic-lethality RNAi screen reveals an ERK-mTOR co-targeting pro-apoptotic switch in PIK3CA(+) oral cancers," *Oncotarget,* 7:10696-10709, 2016.

Zhang et al., "Does Notch play a tumor suppressor role across diverse squamous cell carcinomas?" *Cancer Med.,* 5:2048-2060, 2016.

Zhang et al., "Mutations of the LIM protein AJUBA mediate sensitivity of head and neck squamous cell carcinoma to treatment with cell-cycle inhibitors," *Cancer Lett.,* 392:71-82, 2017.

Zhao et al., "Assembly and initial characterization of a panel of 85 genomically validated cell lines from diverse head and neck tumor sites," *Clin. Cancer Res.,* 17:7248-7264, 2011.

Zumsteg et al., "Taselisib (GDC-0032), a Potent beta-Sparing Small Molecule Inhibitor of PI3K, Radiosensitizes Head and Neck Squamous Carcinomas Containing Activating PIK3CA Alterations," *Clin. Cancer Res.,* 22:2009-2019.

What is claimed is:

1. A method of treating a patient having a squamous cell carcinoma (SCC), the method comprising administering to the patient a therapeutically effective amount of a PI3K inhibitor, wherein the SCC has a NOTCH1 loss-of-function (LOF) mutation.

2. The method of claim 1, wherein the method comprises (a) determining or having determined whether the SCC has a NOTCH1 LOF mutation; (b) selecting or having selected the patient for treatment with a PI3K inhibitor when the SCC has NOTCH1 LOF mutation; and (c) administering or having administered to the selected patient a therapeutically effective amount of a PI3K inhibitor.

3. The method of claim 2, wherein step (a) comprises (i) obtaining or having obtained a biological sample from the SCC; and (ii) performing or having performed an assay on the biological sample to determine whether the SCC has one or more mutations in the NOTCH1 gene or a decreased protein level of cleaved NOTCH1 intracellular domain.

4. The method of claim 3, wherein the assay comprises sequencing the NOTCH1 gene in the SCC.

5. The method of claim 4, wherein the assay further comprises comparing the sequence of the NOTCH1 gene in the SCC to the sequence of the wild-type NOTCH1 gene.

6. The method of claim 5, wherein the wild-type NOTCH1 gene has the sequence of SEQ ID NO: 1.

7. The method of claim 5, wherein the wild-type NOTCH1 gene has a sequence determined by sequencing the NOTCH1 gene in a sample obtained from healthy or non-cancerous tissue in the patient.

8. The method of claim 5, wherein the one or more mutation(s) in the NOTCH1 gene is not a mutation in the TAD domain or in the PEST domain of the NOTCH1 gene, a missense or an in-frame mutation, or a mutation in the splice donor boundary (Exon 33) or the splice acceptor boundary (Exon 34) of the NOTCH1 gene.

9. The method of claim 8, wherein the mutation in the NOTCH1 gene is not within nucleotides 6477-7665 of SEQ ID NO:1.

10. The method of claim 8, wherein the mutation in the NOTCH1 gene is not within nucleotides 4326-5202 of SEQ ID NO:1.

11. The method of claim 8, wherein the mutation in the NOTCH1 gene is not within nucleotides 5639-6082 of SEQ ID NO:1.

12. The method of claim 3, wherein the assay comprises determining a protein level of cleaved NOTCH1 intracellular domain in the SCC.

13. The method of claim 12, wherein the protein level of cleaved NOTCH1 intracellular domain in the SCC is the protein level of cleaved NOTCH1 intracellular domain in the nuclei of the SCC cells.

14. The method of claim 12, wherein the assay further comprises comparing the protein level of cleaved NOTCH1 intracellular domain in the SCC to the level of cleaved NOTCH1 intracellular domain in a reference sample.

15. The method of claim 14, wherein the reference sample is non-cancerous tissue from the patient.

16. The method of claim 14, wherein the reference sample is obtained from a healthy subject.

17. The method of claim 14, wherein a decreased protein level of cleaved NOTCH1 intracellular domain in the SCC relative to the level of cleaved NOTCH1 intracellular domain in a reference sample indicates that the SCC has a NOTCH1 LOF mutation.

18. The method of claim 1, wherein the squamous cell carcinoma is a head and neck squamous cell carcinoma (HNSCC), a skin squamous cell carcinoma, an esophagus squamous cell carcinoma, or a lung squamous cell carcinoma.

19. The method of claim 1, wherein the squamous cell carcinoma is a head and neck squamous cell carcinoma (HNSCC).

* * * * *